United States Patent
Cushman et al.

(10) Patent No.: US 9,399,660 B2
(45) Date of Patent: *Jul. 26, 2016

(54) N-SUBSTITUTED INDENOISOQUINOLINES AND SYNTHESES THEREOF

(71) Applicants: Purdue Research Foundation, West Lafayette, IN (US); THE UNITED STATES OF AMERICA, AS REPRESENTED BY THE SECRETARY OF THE DEPARTMENT OF HEALTH AND HUMAN SERVICES, Washington, DC (US)

(72) Inventors: Mark S. Cushman, West Lafayette, IN (US); Yves George Pommier, Bethesda, MD (US); Peng-Cheng Lu, West Lafayette, IN (US); Christophe Marchand, Silver Spring, MD (US); Keli Agama, Bowie, MD (US)

(73) Assignees: Purdue Research Foundation, West Lafayette, IN (US); NATIONAL INSTITUTES OF HEALTH (NIH), Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/698,335

(22) Filed: Apr. 28, 2015

(65) Prior Publication Data
US 2015/0299246 A1   Oct. 22, 2015

Related U.S. Application Data

(63) Continuation-in-part of application No. 14/339,766, filed on Jul. 24, 2014, now Pat. No. 9,217,010, which is a continuation of application No. 13/317,153, filed on Oct. 11, 2011, now Pat. No. 8,829,022, which is a continuation of application No. 12/093,398, filed as application No. PCT/US2006/043933 on Nov. 13, 2006, now Pat. No. 8,053,443.

(60) Provisional application No. 60/736,471, filed on Nov. 14, 2005, provisional application No. 60/808,699, filed on May 26, 2006, provisional application No. 61/985,748, filed on Apr. 29, 2014.

(51) Int. Cl.
| | |
|---|---|
| *C07D 221/18* | (2006.01) |
| *A61K 31/473* | (2006.01) |
| *C07J 73/00* | (2006.01) |
| *A61K 31/4741* | (2006.01) |
| *C07J 75/00* | (2006.01) |

(52) U.S. Cl.
CPC ............. *C07J 73/005* (2013.01); *A61K 31/473* (2013.01); *A61K 31/4741* (2013.01); *C07D 221/18* (2013.01); *C07J 73/003* (2013.01); *C07J 75/005* (2013.01)

(58) Field of Classification Search
None
See application file for complete search history.

(56) References Cited

U.S. PATENT DOCUMENTS

| | | | | |
|---|---|---|---|---|
| 8,053,443 | B2 * | 11/2011 | Cushman | A61K 31/473 514/284 |
| 8,829,022 | B2 * | 9/2014 | Cushman | A61K 31/473 514/284 |

OTHER PUBLICATIONS

Cushman et al, Journal of Medicinal Chemistry, 2000, 43 (20), pp. 3688-3698.*
Nagarajan et al, Journal of Medicinal Chemistry (2004), 47(23), 5651-5661.*

* cited by examiner

*Primary Examiner* — Zinna Northington Davis
(74) *Attorney, Agent, or Firm* — Mark S. Cohen; Pearl Cohen; Zedek Latzer Baratz LLP

(57) ABSTRACT

N-Substituted indenoisoquinoline compounds, and pharmaceutical formulations of N-substituted indenoisoquinoline compounds are described. Also described are processes for preparing N-substituted indenoisoquinoline compounds. Also described are methods for treating cancer in mammals using the described N-substituted indenoisoquinoline compounds or pharmaceutical formulations thereof.

20 Claims, 3 Drawing Sheets

N-SUBSTITUTED INDENOISOQUINOLINES AND SYNTHESES THEREOF

CROSS REFERENCE TO RELATED APPLICATIONS

This application is a continuation-in-part application of U.S. application Ser. No. 14/339,766, filed Jul. 24, 2014, now U.S. Pat. No. 9,217,010, which is a continuation of U.S. application Ser. No. 13/317,153, filed Oct. 11, 2011, now U.S. Pat. No. 8,829,022, which is a continuation of U.S. application Ser. No. 12/093,398, filed May 12, 2008, now U.S. Pat. No. 8,053,443, which is a U.S. national stage application under 35 U.S.C. §371(b) of International Application No. PCT/US2006/043933, filed Nov. 13, 2006, which claims the benefit under 35 U.S.C. §119 (e) of U.S. Provisional Application Ser. No. 60/736,471, filed Nov. 14, 2005 and U.S. Provisional Application Ser. No. 60/808,699, filed May 26, 2006, and this application also claims the benefit of U.S. Provisional Application Ser. No. 61/985,748, filed Apr. 29, 2014, the disclosures of which are hereby incorporated herein by reference.

GOVERNMENT INTEREST STATEMENT

This invention was made with government support under CA089566 and CA009634 awarded by the National Institutes of Health. The government has certain rights in the invention.

TECHNICAL FIELD

The invention described herein pertains to N-substituted indenoisoquinoline compounds. The invention described herein also pertains to methods for treating cancer in mammals using indenoisoquinoline compounds.

BACKGROUND

The control and cure of cancer represents one of our most challenging health problems. The treatment of cancer can be approached by several modes of therapy including surgery, radiation, chemotherapy or a combination of any of these treatments. Chemotherapy continues to be an indispensable therapy for inoperable or metastatic forms of the disease. Thus, the discovery of compounds specifically targeting cancer cells, or the cellular mechanisms involved in the proliferation of cancer cells, can provide significant advancement the eradication or control of cancer.

The selection of compounds having effective anticancer activity is complicated by the still limited knowledge of cancer cell biology and biochemistry. Therefore, development of new effective anti-cancer agents remains heavily dependent on screening of new compounds for cytotoxic activity. Antineoplastic drug candidates exhibit enhanced cytotoxicity against cancer cells relative to normal cells. Methods of screening for anticancer activity have focused on several targets, (1) the ability of a compound to inhibit tumor growth and/or progression in animal studies; (2) inhibition of cell growth/proliferation in cell lines of cancerous origin; and (3) inhibition of intracellular processes necessary for the growth or propagation of cancer cells.

The mouse L1210 leukemia cell line was initially the preferred model system used for screening compounds for anticancer activity. However, the P388 murine leukemia system was found to be more sensitive and predictive than L1210 leukemia system; it has been used as a primary screen during the past decade. Systematic screening for compounds exhibiting toxicity to these two cell lines has resulted in the isolation of a large number of active natural products. However, the anticancer activities of these compounds were predominantly for leukemia, lymphoma and a few rare tumors. Low clinical efficacy, or the lack of clinical efficacy of known chemotherapeutics against slower growing solid tumors, is a serious concern.

Considering the diversity of cancer in terms of cell type, morphology, growth rate and other cellular characteristics, the U.S. National Cancer Institute (NCI) has developed a disease-oriented approach to anticancer activity screening (M. R. Boyd, in "Principle of Practice of Oncology" J. T. Devita, S. Hellman, S. A. Rosenberg (Eds.) Vol. 3, PPO Update, Nov. 10, 1989). This in vitro prescreening system is based on the measurement of anticancer cytotoxicity against human cancer cell line panels consisting of approximately 60 cell lines of major human cancers (including leukemia, and slower growing tumor cells such as lung, colon, breast, skin, kidney, etc.) and is referred hereinafter as "COMPARE" screening. An important advantage of the new in vitro screening panels is the opportunity to facilitate identification of compounds that are selectively more cytotoxic to cells of certain types of cancers, thus increasing the ability to select compounds for further study with respect to specific diseases.

Anticancer agents are known to act through a variety of mechanisms to destroy or inhibit the proliferation of cancer cells. For example, some agents are antimetabolites which act as false substrates in the biochemical processes of cancer cells. One compound which has this mechanism of action is methotrexate, an analog of folic acid, which functions in part by binding to dihydrofolate reductase, thereby preventing the formation of guanine and adenine from the folic acid precursor molecule. Thus, methotrexate inhibits the ability of cancer cells to construct DNA by inhibiting the proper metabolism of folic acid.

Other anticancer agents act by alkylating DNA strands, thereby producing defects in the normal double helical structure of the DNA molecule. This alkylation may cause the formation of breaks and inappropriate links between for within) strands of DNA. Such disruption of the DNA structure, if not repaired by intracellular repair mechanisms, impairs the cell's ability to replicate its DNA. Examples of alkylating anticancer agents are cyclophosphamide and chlorambucil.

Some anticancer agents target the intracellular mechanisms involved in replication of the DNA strand itself. Replication of a cell's genetic material requires a means to pull the DNA double helix apart into two strands. This separation is typically accomplished by the enzyme topoisomerase I. Disruption of the function of this enzyme results in DNA strand breaks in cells that are dividing, thereby causing the death of the dividing cell. Because cancer cells grow and reproduce at a much faster rate than normal cells, they are more vulnerable to topoisomerase I inhibition than are normal cells. Thus, agents that inhibit topoisomerase I are known to be potent anticancer agents. The drug camptothecin was shown to be an inhibitor of topoisomerase I and a potent anticancer agent. However, it has been observed that camptothecin may produce toxic side effects. In addition, the effectiveness of camptothecin is hampered by both the instability of the molecule itself, resulting in lactone ring opening, and the reversible nature of the inhibition, allowing impacted cells to recover. Therefore, the search for potent inhibitors of topoisomerase I continues.

SUMMARY OF THE INVENTION

Described herein are N-substituted indenoisoquinoline compounds, and more specifically, substituted 11H-indeno

[1,2-c]isoquinoline compounds, including dimers of such substituted 11H-indeno[1,2-c]isoquinoline compounds formed with a divalent linker. The compounds described herein may be useful for treating cancer. Also described herein are pharmaceutical compositions of such compounds, processes for preparing N-substituted indenoisoquinoline compounds, and methods for treating cancer by administering therapeutically effective amounts of such substituted indenoisoquinoline compounds alone or as pharmaceutical compositions.

In one illustrative embodiment, novel compounds of formula I are described

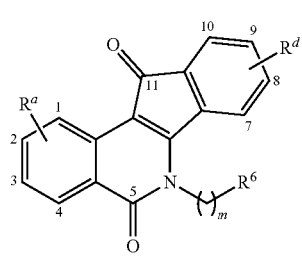

(I)

and pharmaceutically acceptable salts, hydrates, and solvates thereof, wherein:

m is an integer from 0 to about 6;

$R^6$ is selected from haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, hydroxyalkylamino, bis(hydroxyalkyl)amino, hydroxyalkylaminoalkylamino, heteroarylalkylaminoalkylamino, acylamino, hydroxylamino, alkoxylamino, acyloxylamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphoric acid and derivatives thereof; and $R^a$ and $R^d$ each independently represent hydrogen, or one or more optional and independently selected monovalent and divalent substituents.

In one aspect, $R^a$ represents 1-4 substituents each of which is independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another aspect, $R^d$ represents 1-4 substituents each of which is independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^d$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, m is the integer 0. In another embodiment, m is an integer from 1 to about 6, and $R^6$ is selected from halo, haloalkyl, halocycloalkyl, alkoxy, cycloalkoxy, haloalkoxy, halocycloalkoxy, optionally substituted heteroaryl, aryloxy, heteroaryloxy, and heteroarylamino, acyloxy, haloacyloxy, amino, dialkylamino, trialkylammonium, bis(hydroxyalkyl)amino, hydroxyalkylaminoalkylamino, heteroarylalkylaminoalkylamino, acylamino, hydroxylamino, alkoxylamino, acyloxylamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphoric acid and derivatives thereof.

In another illustrative embodiment, $R^6$ includes a water soluble or hydrophilic functional group. In one aspect, $R^6$ includes an optionally substituted aminoalkyl. In another aspect, $R^6$ includes an alkyl group substituted with optionally substituted heteroaryl, heteroaryloxy, or heteroarylamino, amino, dialkylamino, trialkylammonium, bis(hydroxyalkyl) amino, hydroxyalkylaminoalkylamino, heteroarylalkylaminoalkylamino, acylamino, hydroxylamino, alkoxylamino, acyloxylamino, heterocyclyl, heterocyclylamino, nitro, or azido.

In another illustrative embodiment, $R^a$ represents 1-4 substituents each of which is independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, $R^a$ represents 2-4 substituents where 2 of said substituents are adjacent substituents and are taken together with the attached carbons to form an optionally substituted heterocycle, and where any remaining substituents are each independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, $R^d$ represents 1-4 substituents each of which is independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, $R^d$ represents 2-4 substituents where 2 of said substituents are adjacent substituents and are taken together with the attached carbons to form an optionally substituted heterocycle, and where any remaining substituents are each independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, m is an integer from 0 to about 6, and $R^6$ is selected from the group consisting of haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, bis(hydroxyalkyl)amino, hydroxyalkylaminoalkylamino, heteroarylalkylaminoalkylamino, acylamino, hydroxyamino, alkoxylamino, acyloxylamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphonic acid and derivatives thereof; provided that when $R^6$ is hydroxy, alkylamino, or hydroxyalkylamino, m is the integer 0.

In another illustrative embodiment, novel compounds of formula II are described

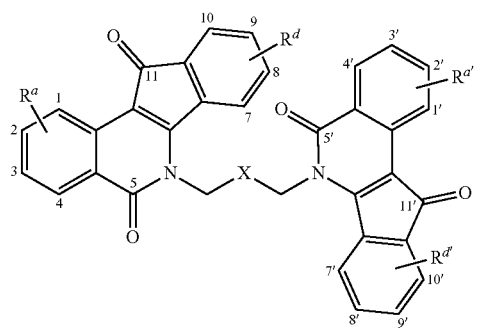

(II)

and pharmaceutically acceptable salts, hydrates, and solvates thereof, wherein:

$R^a$, $R^d$, $R^{a'}$, and $R^{d'}$ each independently represent 4 substituents, all of which are independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or where 2 of said substituents are adjacent substituents and are taken together with the attached carbons to form an optionally substituted heterocycle; and X is a divalent linker comprising one or more divalent radicals selected from $-(CR^1R^2)$, $-(NR^1)-$ and $-O-$, where $R^1$ and $R^2$ are independently selected in each occurrence from hydrogen, alkyl, and acyl, providing that the divalent linker does not include $-O-O-$. In one aspect, if present, each divalent $-(NR^1)-$ and $-O-$ is separated by at least one divalent radical $(-CR^1R^2)-$. In another aspect, each $R^1$ and $R^2$ is hydrogen.

In another illustrative embodiment, X is a group having the general structure $-(CH_2)_n-[(CH_2)_x-NR^1-(CH_2)_y]_z-(NR^2)_p-(CH_2)_q-$, where n is 0 or 1, x and y are integers independently ranging from 1 to about 4, z is an integer ranging from 1 to about 4, p is 0 or 1, q is 0 or an integer ranging from 1 to about 2, and where $R^1$ and $R^2$ are independently selected in each instance from hydrogen, methyl, t-butyloxycarbonyl, benzyloxycarbonyl, and fluorenylmethoxycabonyl, or $R^1$ and $R^2$ and any adjacent $R^2$ together with the attached nitrogens form a heterocycle.

In another illustrative embodiment, indenoisoquinoline compounds of formulae I and II described herein are useful for treating cancer or tumors. In one aspect, compounds described herein exhibit the activity of stabilizing DNA-topoisomerase 1 cleavage complexes through intercalation at the DNA cleavage site, resulting in inhibition of the religation reaction. See, for example, Kohlhagen, G; Paull, K.; Cushman, M.; Nagafuji, P.; Pommier, Y. Protein-Linked DNA Strand Breaks Induced by NSC 314622, a Novel Noncamptothecin Topoisomerase I Poison *Mol. Pharmacol.* 1998, 54, 50-58; Pommier, Y.; Pourquier, P.; Fan, Y.; Strumberg, D. Mechanism of Action of Eukaryotic DNA Topoisomerases and Drugs Targeted to the Enzyme *Biochem. Biophys. Acta.* 1998, 1400, 83-105; Staler, B. L.; Hjerrild, K.; Feese, M. D.; Behnke, C. A.; Burgin Jr., A. B.; Stewart, L. The Mechanism of Topoisomerase I Poisoning by a Camptothecin Analog *Proc. Natl. Acad. Sci. U.S.A.* 2002, 99, 15387-15392, the disclosures of each of which are incorporated herein by reference. As inhibitors of the DNA religation reaction occurring after DNA cleavage by topoisomerase 1, compounds described herein may be classified as "top1 poisons," and may exhibit biological and pharmacological activity similar to that observed with camptothecins. In another aspect, indenoisoquinoline compounds of formulae I and II described herein may be efficacious against various types of human cancers. In another aspect, indenoisoquinoline compounds of formulae I and II described herein may be chemically more stable than camptothecin. In yet another aspect, indenoisoquinoline compounds of formulae I and II described herein may have unique DNA binding site selectivities relative to camptothecin.

In another illustrative embodiment, methods for treating human cancers are described. In one aspect of the methods described herein, the cancers are attributable to abnormally fast cell growth, reproduction, and/or proliferation. In another aspect, the cancers treatable by compounds of formulae I and II are responsive to enzyme inhibition, such as inhibition of topoisomerase 1.

In another illustrative embodiment, processes for preparing indenoisoquinoline compounds of formula I and II are described. In one embodiment, the processes include preparing an intermediate benz[d]indeno[1,2-b]pyran-5,11-dione of the formula III

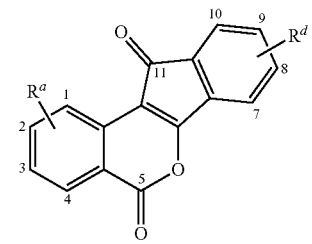

(III)

where the process comprises reacting a 2-carboxybenzaldehyde compound and a phthalide compound of respective formulae

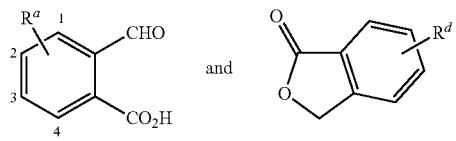

followed by acidic treatment in benzene under reflux or treatment with a suitable coupling reagent such as dicyclohexylcarbodiimide with dimethyaminopyridine, wherein $R^a$ and $R^d$ are as defined herein for compounds of formulae I and II.

In another illustrative embodiment, processes are described herein for preparing compounds of formulae I and II comprising the steps of (i) reacting an $R^a$-substituted hydroxy phthalide compound and an $R^d$-substituted phthalide compound of respective formulae

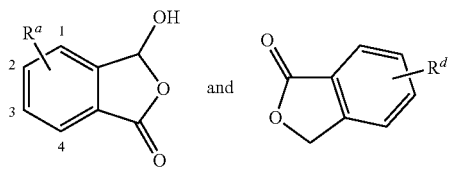

and in the presence of a base, then (ii) treating the mixture with an acid to prepare the intermediate benz[d]indeno[1,2-b]pyran-5,11-dione described above, wherein $R^a$ and $R^d$ are as defined herein for compounds of formulae I and II.

In another illustrative embodiment, processes are described herein for preparing compounds of formulae I and II comprising the steps of reacting a benz[d]indeno[1,2-b]pyran-5,11-dione of the formula

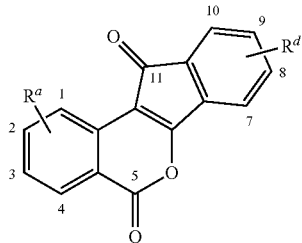

with a primary amine of the formula $R^6$—$(CH_2)_m$—$NH_2$, wherein $R^a$, $R^d$, m, and $R^6$ are as defined herein for compounds of formulae I and II. In one embodiment, the primary amine is illustratively 4-(2-aminoethyl)morpholine, 1-(3-aminopropyl)imidazole, N-(3-aminopropyl)-N,N-dimethylamine, 4-(hydroxy)butylamine, 3-(bromo)propylamine, a mono-Boc-protected diamine, and the like. It is appreciated that although chloroform at room temperature will suffice as the solvent for most primary amines, when a primary amine such as a mono-Boc-protected diamine, for example, is used to form the lactam from a benz[d]indeno[1,2-b]pyran-5,11-dione, chloroform at reflux may be used as the solvent. It is further appreciated that an indenoisoquinoline compound for which the integer m is not 0, and wherein $R^6$ is halo, azido, or cyano, for example, may be further elaborated through displacement of the halo, azido, or cyano functionality, respectively, with a variety of nucleophiles.

In another illustrative embodiment, processes are described herein for preparing compounds of formulae I and II comprising the steps of reacting an optionally substituted homophthalic anhydride and an optionally substituted Schiff base of respective formulae

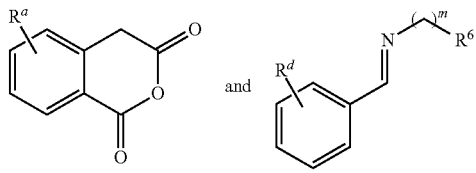

and followed by subjecting the resulting carboxylic acid to oxidative Friedel-Crafts ring closure with thionyl chloride and aluminum chloride, wherein $R^a$, $R^d$, m, and $R^6$ are as defined herein for compounds of formulae I and II.

In another illustrative embodiment, processes are described herein for preparing compounds of formulae I and II comprising the steps of reacting a benz[d]indeno[1,2-b]pyran-5,11-dione of the formula

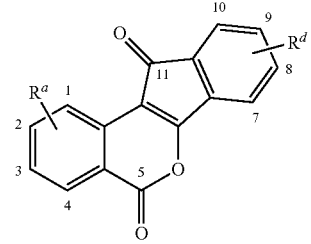

with a polyamine of the formula $NH_2$—$(CH_2)_n$—$[(CH_2)_x$—$NR^1$—$(CH_2)_y]_z$—$(NR^2)_p$—$(CH_2)_q$—$NH_2$, where $R^1$, $R^2$, n, x, y, z, p, q, $R^a$, and $R^d$ are as defined herein for compounds of formula II. In one embodiment, the polyamine is illustratively N,N-bis(2-aminoethyl)amine, N,N-bis(3-aminopropyl)amine, N-(2-aminoethyl)-N-(3-aminopropyl)-amine, N,N'-bis(2-aminoethyl)-1,3-propanediamine, N,N'-bis(3-aminopropyl)-1,3-propanediamine and the like.

It is to be understood that each of the aspects of the various illustrative embodiments described herein may be modified and/or combined as additional illustrative embodiments. For example, illustrative embodiments of the compounds of formula II may include those aspects wherein an unsubstituted, symmetrical bisindenoisoquinoline is present, as reflected in the use of a benz[d]indeno[1,2-b]pyran-5,11-dione where $R^a$ and $R^d$ are each hydrogen. Further, illustrative embodiments of the compounds of formula II may include those aspects wherein a substituted, symmetrical bisindenoisoquinoline is present, as reflected in the use of a benz[d]indeno[1,2-b]pyran-5,11-dione where, for example, $R^a$ is 2,3-dimethoxy and $R^d$ is hydrogen, or where, for example, $R^a$ is 3-nitro and $R^d$ is hydrogen. In addition, illustrative embodiments of the compounds of formula II may include those aspects wherein a substituted, unsymmetrical bisindenoisoquinoline is present, as reflected in the use of a mixture of two differentially substituted benz[d]indeno[1,2-b]pyran-5,11-diones to prepare a dimer such as

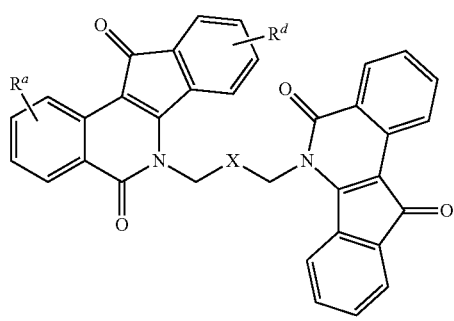

wherein Ra, Rd, and X are as defined herein for compounds of formula II, and wherein Ra≠H and/or Rd≠H.

In one illustrated embodiment, novel compounds of formula I are described

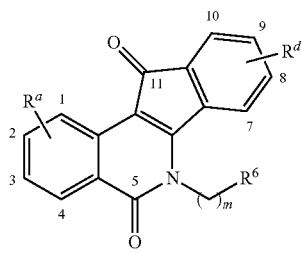

(I)

and pharmaceutically acceptable salts, hydrates, and solvates thereof,
wherein:
m is an integer from 0 to about 6;
$R^6$ is selected from the group consisting of haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, hydroxyalkylamino, bis(hydroxyalkyl)amino, hydroxyalkylaminoalkylamino, heteroarylalkylaminoalkylamino, acylamino, hydroxylamino, alkoxylamino, acyloxylamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphonic acid and derivatives thereof; provided that when $R^6$ is hydroxy, alkylamino, or hydroxyalkylamino, m is the integer 0;
$R^a$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; and
$R^d$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^d$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrated embodiment, $R^6$ is selected from the group consisting of amino, alkyl and dialkylamino, trialkylammonium, hydroxyalkylamino, bis(hydroxyalkyl)amino, hydroxyalkylaminoalkylamino, and azido.

In another illustrated embodiment, $R^6$ is selected from the group consisting of amino, alkyl and dialkylamino, trialkylammonium, bis(hydroxyalkyl)amino, hydroxyalkylaminoalkylamino, and azido.

In another illustrated embodiment, $R^6$ is selected from the group consisting of heteroaryl, heteroaryloxy, and heteroarylamino, heteroarylalkylaminoalkylamino, heterocyclyl, heterocyclylamino, each of which is optionally substituted.

In another illustrated embodiment, $R^6$ is optionally substituted heterocyclyl or optionally substituted heterocyclylamino. In one embodiment, $R^6$ is morpholin-4-yl. In another illustrated embodiment, $R^6$ is optionally substituted heteroaryl or optionally substituted heteroarylamino. In one embodiment, $R^6$ is imidazole-1-yl.

In another illustrated embodiment, $R^d$ includes an alkylenedioxy group. In another illustrated embodiment, $R^d$ includes one or more optionally substituted alkoxy.

In another illustrated embodiment, $R^a$ includes one or more alkoxy optionally substituted with hydroxy, alkoxy, alkylsulfonyl, alkenyl, alkynyl, halo, nitro, cyano, azido, amino, alkylamino, dialkylamino, hydroxyalkylamino, bis(hydroxyalkyl)amino, cycloalkyl, aryl, heterocyclyl, heteroaryl, alkylcarbonyl, alkoxycarbonyl, or hydrazinecarbonyl.

In another illustrated embodiment, $R^a$ includes one or more alkoxy optionally substituted with alkenyl, alkynyl, halo, nitro, cyano, azido, amino, alkylamino, dialkylamino, hydroxyalkylamino, bis(hydroxyalkyl)amino, cycloalkyl, aryl, heterocyclyl, heteroaryl, alkylcarbonyl, alkoxycarbonyl, or hydrazinecarbonyl. In one embodiment, the alkoxy is optionally substituted with amino, alkylamino, dialkylamino, hydroxyalkylamino, or bis(hydroxyalkyl)amino. In one embodiment, the alkoxy is optionally substituted with amino, alkylamino, or dialkylamino. In another embodiment, the alkoxy is optionally substituted with heterocyclyl. In certain embodiment, the heterocyclyl is morpholino, 4-methylpiperazinyl, piperidinyl, or pyrrodinyl. In another embodiment, the alkoxy is optionally substituted with alkylcarbonyl, alkoxycarbonyl, or hydrazinecarbonyl.

In another illustrated embodiment, $R^a$ includes one methoxy and one alkoxy substituted with alkenyl, alkynyl, halo, nitro, cyano, azido, amino, alkylamino, dialkylamino, cycloalkyl, aryl, hetereocyclyl, heteroaryl, alkylcarbonyl, alkoxycarbonyl, or hydrazinecarbonyl. In one embodiment, $R^a$ includes one optionally substituted alkoxy and one hydroxy.

In another illustrated embodiment, a pharmaceutical composition comprising a compound as described herein, or a pharmaceutically acceptable salt, hydrate, or solvate thereof, and one or more pharmaceutically acceptable carriers, diluents, and excipients.

DETAILED DESCRIPTION

Figure 1:
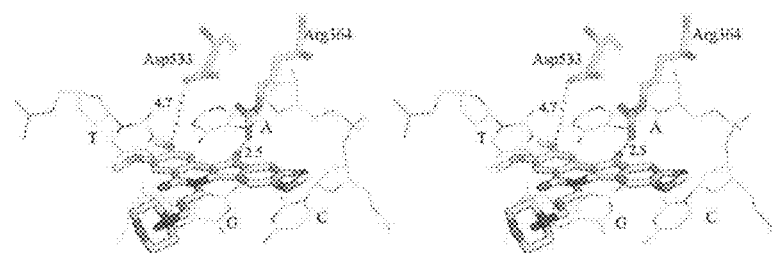
FIG. 1 depicts a hypothetical binding mode of compound 18 in ternary complex with DNA and Top1. All distances are measured from heavy atom to heavy atom. The diagram is programmed for wall-eyed (relaxed) viewing. Compound 18 is shown in sticks, and the base pairs are displayed in lines.

In one illustrative embodiment, novel compounds of formula I are described

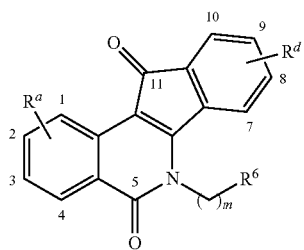

(I)

and pharmaceutically acceptable salts, hydrates, and solvates thereof, wherein:

m is an integer from 0 to about 6; and $R^6$ is selected from haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, hydroxyalkylamino, bis(hydroxyalkyl)amino, hydroxyalkylaminoalkylamino, heteroarylalkylaminoalkylamino, acylamino, hydroxyamino, alkoxyamino, acyloxylamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphoric acid and derivatives thereof;

$R^a$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; and $R^d$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^d$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

As used herein, the term "alkyl" refers to a saturated monovalent chain of carbon atoms, which may be optionally branched. It is understood that in embodiments that include alkyl, illustrative variations of those embodiments include lower alkyl, such as $C_1$-$C_6$, $C_1$-$C_4$ alkyl, methyl, ethyl, propyl, 3-methylpentyl, and the like.

As used herein, the term "cycloalkyl" refers to a monovalent chain of carbon atoms, a portion of which forms a ring. It is understood that in embodiments that include cycloalkyl, illustrative variations of those embodiments include lower cycloalkyl, such as $C_3$-$C_8$, $C_3$-$C_6$ cycloalkyl, cyclopropyl, cyclohexyl, 3-ethylcyclopentyl, and the like.

As used herein, the term "alkenyl" refers to an unsaturated monovalent chain of carbon atoms including at least one double bond, which may be optionally branched. It is understood that in embodiments that include alkenyl, illustrative variations of those embodiments include lower alkenyl, such as $C_2$-$C_6$, $C_2$-$C_4$ alkenyl.

As used herein, the term "cycloalkenyl" refers to an unsaturated monovalent chain of carbon atoms, a portion of which forms a ring. It is understood that in embodiments that include cycloalkenyl, illustrative variations of those embodiments include lower cycloalkenyl, such as $C_3$-$C_8$, $C_3$-$C_6$ cycloalkenyl.

As used herein, the term "alkylene" refers to a saturated bivalent chain of carbon atoms, which may be optionally branched. It is understood that in embodiments that include alkylene, illustrative variations of those embodiments include lower alkylene, such as $C_2$-$C_4$, alkylene, methylene, ethylene, propylene, 3-methylpentylene, and the like.

As used herein, the term "heterocycle" refers to a monovalent chain of carbon and heteroatoms, wherein the heteroatoms are selected from nitrogen, oxygen, and sulfur, a portion of which, including at least one heteroatom, form a ring, such as aziridine, pyrrolidine, oxazolidine, 3-methoxypyrrolidine, 3-methylpiperazine, and the like.

It is to be understood that each of alkyl, cycloalkyl, alkenyl, cycloalkenyl, alkylene, and heterocyclyl may be optionally substituted with independently selected groups such as alkyl, haloalkyl, hydroxyalkyl, aminoalkyl, carboxylic acid and derivatives thereof, including esters, amides, and nitriles, hydroxy, alkoxy, acyloxy, amino, alkyl and dialkylamino, acylamino, thio, and the like, and combinations thereof.

As used herein, the term "optionally substituted aryl" refers to an aromatic mono or polycyclic ring of carbon atoms, such as phenyl, naphthyl, and the like, which may be optionally substituted with one or more independently selected substituents, such as halo, hydroxy, amino, alkyl or dialkylamino, alkoxy, alkylsulfonyl, cyano, nitro, and the like.

As used herein, the term "optionally substituted heteroaryl" refers to an aromatic mono or polycyclic ring of carbon atoms and at least one heteroatom selected from nitrogen, oxygen, and sulfur, such as pyridinyl, pyrimidinyl, indolyl, benzoxazolyl, and the like, which may be optionally substituted with one or more independently selected substituents, such as halo, hydroxy, amino, alkyl or dialkylamino, alkoxy, alkylsulfonyl, cyano, nitro, and the like.

As used herein, the term "acyl" refers to hydrogen, alkyl, cycloalkyl, alkenyl, cycloalkenyl, heterocyclyl, optionally substituted aryl, optionally substituted arylalkyl, optionally substituted heteroaryl, and optionally substituted heteroarylalkyl attached as a substituent through a carbonyl (C=O) group, such as formyl, acetyl, pivalolyl, benzoyl, phenacetyl, and the like.

As used herein, "alkoxy" refers to an —O-alkyl group. Example alkoxy groups include methoxy, ethoxy, propoxy (e.g., n-propoxy and isopropoxy), t-butoxy, and the like.

As used herein, the terms "alkylamino," "dialkylamino," "dialkylammonium," and "trialkyammonium" refer to amino substituted with alkyl groups, where each alkyl group is independently selected, and illustratively includes dimethylamino, methylethylamino, diisopropylethylammonium, benzyldimethylammonium, benzyldiisopropylammonium, and the like.

As used herein, the terms "protected hydroxy" and "protected amino" refer to hydroxy and amino groups, respectively, that are protected with a protecting group. It is to be understood that such protecting groups are conventional and routinely selected to allow a synthetic or chemical transformation to be performed in a manner that the hydroxy group or amino group does not interfere with or is not changed by the synthetic or chemical transformation performed. Illustrative, but not exclusive, examples of such protecting groups may be found in Greene & Wuts "Protective Groups in Organic Synthesis," 2d Ed., John Wiley & Sons, New York, 1991, the disclosure of which is incorporated herein by reference. Further illustrative of such protecting groups are those particularly suited for protecting phenols and catechols, and analogs and derivatives thereof.

In one illustrative aspect of the compounds of formula I, $R^6$ is dialkylamino, including dimethylamino, azido, poly(hydroxyalkyl)amino, hydroxyalkylaminoalkylamino, polyhydroxyalkylaminoalkylamino, hydroxyalkyl(alkylamino), heteroaryl, or a combination thereof. In another aspect, $R^6$ is selected from the formulae

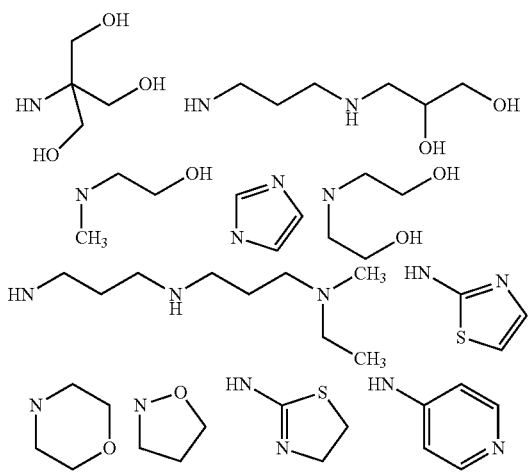

each of which may be optionally substituted. In another aspect, m is 2, 3, or 4.

In another aspect of the compounds of formula I, $R^6$ is alkyl substituted with amino, dialkylamino, trialkylammonium, poly(hydroxyalkyl)amino, hydroxyalkylaminoalkylamino, (polyhydroxy)alkylaminoalkylamino, heteroaryl, azido, hydroxyalkyl(alkylamino), and combinations thereof. In another aspect, $R^6$ is substituted $C_1$-$C_4$ alkyl. In another aspect, $R^6$ is substituted $C_3$ alkyl.

In another illustrative embodiment of the compounds of formula I, $R^a$ represents one or more substituents selected from optionally substituted alkoxy. In one aspect, $R^a$ represents at least two adjacent substituents taken together to form alkylenedioxy. In another embodiment, $R^a$ represents one or more substituents selected from halo, hydroxy, amino, alkyl and dialkylamino, nitroso, nitro, hydroxylamino, alkoxylamino, and cyano. In another embodiment of the compounds of formula I, $R^d$ represents one or more substituents selected from optionally substituted alkoxy. In one aspect, $R^d$ represents at least two adjacent substituents taken together to form alkylenedioxy. In another embodiment, $R^d$ represents one or more substituents selected from halo, amino, alkyl and dialkylamino, nitroso, nitro, and cyano.

In another illustrative embodiment of the compounds of formula I, $R^6$ is alkyl substituted with amino, dialkylamino, trialkylammonium, poly(hydroxyalkyl)amino, hydroxyalkylaminoalkylamino, (polyhydroxy)alkylaminoalkylamino, heteroaryl, azido, hydroxyalkyl(alkylamino), and combinations thereof. In another aspect, $R^6$ is substituted $C_1$-$C_4$ alkyl. In another aspect, $R^6$ is substituted $C_3$ alkyl. In another aspect, $R^a$ represents one or more substituents selected from optionally substituted alkoxy. In another aspect, $R^a$ represents at least two adjacent substituents taken together to form alkylenedioxy. In another aspect, $R^a$ represents one or more substituents selected from halo, hydroxy, amino, alkyl and dialkylamino, nitroso, nitro, hydroxylamino, alkoxylamino, and cyano. In another aspect, $R^d$ represents one or more substituents selected from optionally substituted alkoxy. In another aspect, $R^d$ represents at least two adjacent substituents taken together to form alkylenedioxy. In another aspect, $R^d$ represents one or more substituents selected from halo, amino, alkyl and dialkylamino, nitroso, nitro, and cyano.

In another illustrative embodiment, indenobenzopyran compounds of formula III are described, where $R^a$ and $R^d$ are as defined in the compounds of formulae I and II. These compounds may be used to prepare compounds of formulae I and II according to the processes described herein. In one embodiment, compounds 4a-4s are described, as shown in the following table. Compounds 4a-4s were prepared by the processes described herein comprising the steps of preparing and cyclizing the adduct of an optionally substituted 2-carboxybenzaldehyde and an optionally substituted phthalide as described herein.

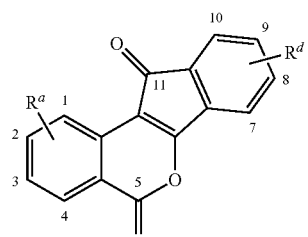

(III)

| Compound | $R^a$ | $R^a$ |
|---|---|---|
| 4a | 2,3-(MeO)$_2$ | H |
| 4b | 2,3-(OCH$_2$O) | H |

| Compound | $R^a$ | $R^a$ |
|---|---|---|
| 4c | 3-NO$_2$ | H |
| 4d | H | H |
| 4e | 2,3-(MeO)$_2$ | 8,9-(OCH$_2$O) |
| 4f | 2,3-(MeO)$_2$ | 8,9-(MeO)$_2$ |
| 4g | 2,3-(MeO)$_2$ | 7,8,9-(MeO)$_3$ |
| 4h | 2,3-(OCH$_2$O) | 8,9-(MeO)$_2$ |
| 4i | 2,3-(OCH$_2$O) | 8,9-(OCH$_2$O) |
| 4j | 2,3-(OCH$_2$O) | 7,8,9-(MeO)$_3$ |
| 4k | 1,2,3-(MeO)$_3$ | 8,9-(MeO)$_2$ |
| 4l | 1,2,3-(MeO)$_3$ | 8,9-(OCH$_2$O) |
| 4m | 1,2,3-(MeO)$_3$ | 7,8,9-(MeO)$_3$ |
| 4n | 1,4-(MeO)$_2$ | 8,9-(MeO)$_2$ |
| 4o | 1,4-(MeO)$_2$ | 8,9-(OCH$_2$O) |
| 4p | 1,4-(MeO)$_2$ | 7,8,9-(MeO)$_3$ |
| 4q | 2,3,4-(MeO)$_3$ | 8,9-(MeO)$_2$ |
| 4r | 2,3,4-(MeO)$_3$ | 8,9-(OCH$_2$O) |
| 4s | 2,3,4-(MeO)$_3$ | 7,8,9-(MeO)$_3$ |

In another illustrative embodiment, novel indenoisoquinoline compounds 5a-5z, 5aa-5az, and 5ba-5bs are described.

These compounds were prepared by the processes described herein comprising the steps of preparing the corresponding benz[d]indeno[1,2-b]pyran-5,11-dione and converting the lactone into the corresponding lactam with a suitable primary amine, or by condensing an optionally substituted homophthalic anhydride and an optionally substituted Schiff base, as described herein.

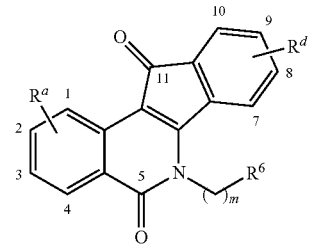

(I)

| Compound | $R^a$ | $R^d$ | m | $R^6$ |
|---|---|---|---|---|
| 5a | 2,3-(MeO)$_2$ | H | 3 | (Me)$_2$N |
| 5b | 2,3-(OCH$_2$O) | H | 3 | (Me)$_2$N |
| 5c | 3-NO$_2$ | H | 3 | (Me)$_2$N |
| 5d | H | H | 3 | (Me)$_2$N |
| 5e | 2,3-(MeO)$_2$ | H | 3 | imidazol-1-yl |
| 5f | 3-NO$_2$ | H | 3 | imidazol-1-yl |
| 5g | H | H | 3 | imidazol-1-yl |
| 5h | 2,3-(MeO)$_2$ | H | 2 | morpholin-4-yl |
| 5i | 3-NO$_2$ | H | 2 | morpholin-4-yl |
| 5j | H | H | 2 | morpholin-4-yl |
| 5k | 2,3-(MeO)$_2$ | 8,9-(OCH$_2$O) | 3 | CF$_3$CO$_2$ |
| 5l | 2,3-(MeO)$_2$ | 8,9-(OCH$_2$O) | 3 | imidazol-1-yl•2HCl |
| 5m | 2,3-(MeO)$_2$ | 8,9-(OCH$_2$O) | 3 | pyrazol-1-yl |
| 5n | 2,3-(MeO)$_2$ | 8,9-(OCH$_2$O) | 3 | triazol-1-yl•HCl |
| 5o | 2,3-(MeO)$_2$ | 8,9-(OCH$_2$O) | 3 | thiazol-2-ylamino•2HCl |
| 5p | 2,3-(MeO)$_2$ | 8,9-(OCH$_2$O) | 3 | piperazin-1-yl•2HCl |
| 5q | 2,3-(MeO)$_2$ | 8,9-(OCH$_2$O) | 3 | morpholin-4-yl |
| 5r | 2,3-(MeO)$_2$ | 8,9-(OCH$_2$O) | 3 | thomorpholin-4-yl |
| 5s | 2,3-(MeO)$_2$ | 8,9-(OCH$_2$O) | 3 | 3-hydroxypiperidin-1-yl•HCl |
| 5t | 2,3-(MeO)$_2$ | 8,9-(OCH$_2$O) | 3 | 1-methylpiperazin-1-yl•2HCl |
| 5u | 2,3-(MeO)$_2$ | 8,9-(OCH$_2$O) | 3 | 4-aminopiperidin-1-yl•2HCl |
| 5v | 2,3-(MeO)$_2$ | 8,9-(OCH$_2$O) | 3 | homopiperazin-1-yl•2HCl |
| 5w | 2,3-(MeO)$_2$ | 8,9-(OCH$_2$O) | 3 | 4-(hydroxyethyl)piperazin-1-y |
| 5x | 2,3-(MeO)$_2$ | 8,9-(OCH$_2$O) | 3 | morpholinylethylamino |
| 5y | 2,3-(MeO)$_2$ | 8,9-(OCH$_2$O) | 3 | bromo |
| 5z | H | H | 0 | —NH$_2$ |
| 5aa | H | H | 2 | —NHBoc |
| 5ab | H | H | 3 | —NHBoc |
| 5ac | H | H | 4 | —NHBoc |
| 5ad | H | H | 5 | —NH$_2$ |
| 5ae | H | H | 6 | —NH$_2$ |
| 5af | H | H | 7 | —NHBoc |
| 5ag | H | H | 8 | —NHBoc |
| 5ah | H | H | 9 | —NHBoc |
| 5ai | H | H | 10 | —NHBoc |
| 5aj | H | H | 11 | —NHBoc |
| 5ak | H | H | 12 | —NHBoc |
| 5al | H | H | 2 | —NH$_3^+$Cl$^-$ |
| 5am | H | H | 3 | —NH$_3^+$Cl$^-$ |
| 5an | H | H | 4 | —NH$_3^+$Cl$^-$ |
| 5ao | H | H | 5 | —NH$_3^+$Cl$^-$ |
| 5ap | H | H | 6 | —NH$_3^+$Cl$^-$ |
| 5aq | H | H | 7 | —NH$_3^+$Cl$^-$ |
| 5ar | H | H | 8 | —NH$_3^+$Cl$^-$ |
| 5as | H | H | 9 | —NH$_3^+$Cl$^-$ |
| 5at | H | H | 10 | —NH$_3^+$Cl$^-$ |
| 5au | H | H | 11 | —NH$_3^+$Cl$^-$ |
| 5av | H | H | 12 | —NH$_3^+$Cl$^-$ |
| 5aw | H | H | 1 | 2-pyridyl |
| 5ax | H | H | 1 | 3-pyridyl |
| 5ay | H | H | 2 | 2-pyridyl |

-continued

| Compound | $R^a$ | $R^d$ | m | $R^6$ |
|---|---|---|---|---|
| 5az | H | H | 2 | 3-pyridyl |
| 5ba | 3-$NO_2$ | 9-MeO | 3 | chloro |
| 5bb | 3-$NO_2$ | H | 3 | bromo |
| 5bc | H | 9-MeO | 3 | chloro |
| 5bd | 3-$NO_2$ | 9-MeO | 3 | iodo |
| 5be | H | 9-MeO | 3 | iodo |
| 5bf | H | 9-MeO | 3 | azido |
| 5bg | H | 9-MeO | 3 | —$NH_3^+Cl^-$ |
| 5bh | H | H | 3 | azido |
| 5bi | 3-$NO_2$ | H | 3 | morpholin-4-yl |
| 5bj | 3-$NO_2$ | 9-MeO | 3 | morpholin-4-yl |
| 5bk | H | 9-MeO | 3 | morpholin-4-yl |
| 5bl | 3-$NO_2$ | H | 3 | —NH—$CH_2$—$CH_2$—OH•HCl |
| 5bm | 3-$NO_2$ | 9-MeO | 3 | —NH—$CH_2$—$CH_2$—OH•HCl |
| 5bn | H | 9-MeO | 3 | —NH—$CH_2$—$CH_2$—OH•HCl |
| 5bo | H | H | 3 | —NH—$CH_2$—$CH_2$—OH•HCl |
| 5bp | 3-$NO_2$ | 9-MeO | 3 | $(Me)_2N$ |
| 5bq | H | 9-MeO | 3 | $(Me)_2N$ |
| 5br | 3-$NO_2$ | 9-MeO | 3 | imidazol-1-yl |
| 5bs | H | 9-MeO | 3 | imidazol-1-yl |

It is appreciated that compounds 5a-5z, 5aa-5az, and 5ba-5bs may be chemically more stable than camptothecin, owing, at least in part, to the absence of a lactone ring, such as is found in camptothecin. See, (a) Jaxel, C.; Kohn, K. W.; Wani, M. C.; Pommier. Y. Structure-Activity Study of the Actions of Camptothecin Derivatives on Mammalian Topoisomerase 1: Evidence for a Specific Receptor Site and a Relation to Antitumor Activity *Cancer. Rev.* 1989, 49, 1465-1469. (b) Minanri, H.; Beijnen, J. H.; Verweij, J.; Ratain, M. J. Limited Sampling Model for the Area under the Concentration Time Curve of Total Topotecan *Clin. Cancer Res.* 1996, 2, 43.46. (c) Danks, M. K.; Pawlik, C. A.; Whipple, D. O.; Wolverton, J. S. Intermittant Exposure of Medulloblastoma Cells to Topotecan Produces Growth Inhibition equivalent to Continuous Exposure *Curr. Topics Med. Chem.* 1997, 3, 1731-1738. (d) Haas. N. B.; LaCreta, F. P.; Walczak, J.; Hudes, G. R.; Brennan, J. M.; Ozols, R. F.; O'Dwyer, P. J. PhaseI/Pharmaco-kinetic Study of Topotecan by 24-Hour Continuous infusion Weekly *Cancer Res.* 1994, 54, 1220-1226, the disclosures of which are incorporated herein by reference. It is further appreciated that compounds 5a-5z, 5aa-5az, and 5ba-5bs may be efficacious against various types of human cancers. It is also appreciated that compounds 5a-5z, 5aa-5az, and 5ba-5bs may have unique DNA binding site selectivities relative to camptothecin.

In another illustrative embodiment, processes for preparing unsubstituted benz[d]indeno[1,2-b]pyran-5,11-dione 4d are described. In one aspect, indenobenzopyran 4d may be prepared as shown in Scheme 1, wherein condensation of 2-carboxybenzaldehyde 1d and phthalide 2d in methanol/ethyl acetate with sodium methoxide (step (a)) generates an intermediate 3d, which can be isolated and subsequently cyclized in acidified, refluxing benzene (step (b)) to provide indenobenzopyran 4d. See, Shapiro, S. L.; Geiger, K.; Youlus, J.; Freedman, L. Indandiones A Modified Dieckman Reaction *J. Org. Chem.* 1961, 26, 3580-3582. In another aspect, indenobenzopyran 4d was prepared by a novel, one-pot two-step method, without isolation of intermediate 3d, which resulted in an improved yield (86%) compared to the previously reported synthesis yield (31%). See, Palior. M.; Worther, H.; Meller, A. Some reactions of 2-aryl-1,3indandiones *Monatsh Chem,* 1961, 92, 1037-1047.

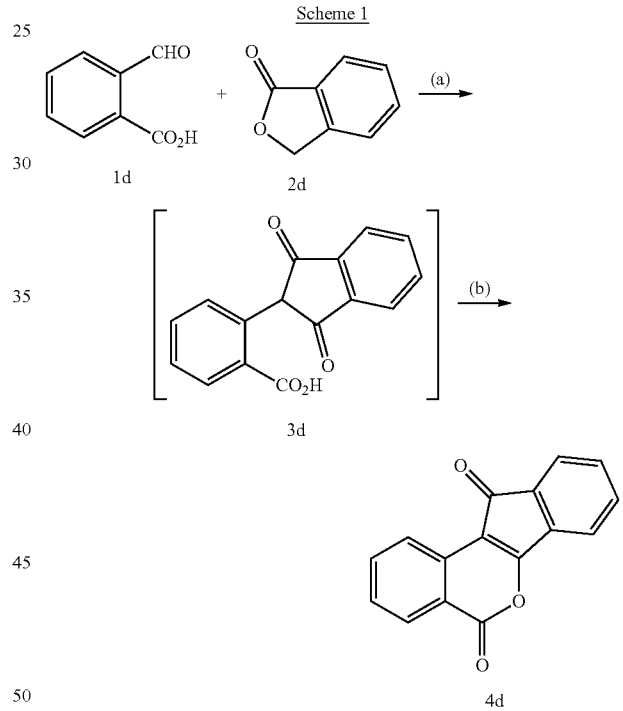

Scheme 1

In another illustrative embodiment, substituted benz[d]indeno[1,2-b]pyran-5,11-diones 4 are prepared as shown in Scheme 2. Treatment of optionally substituted phthalide 2 with N-bromosuccinimide in carbon tetrachloride/benzene under reflux (step (a)) affords brominated phthalide 2e. Treating brominated phthalide 2e with aqueous acidic conditions under reflux (step (b)) affords hydroxylated phthalide 2f. Condensation of hydroxylated phthalide 2f with optionally substituted phthalide 2 in a solution comprising methanol at room temperature, and an organic base, such as sodium methoxide (step (c)), followed by reflux under acidic conditions (step (d)) affords optionally substituted indenobenzopyrans 4, where $R^a$ and $R^d$ are as defined herein.

Scheme 2

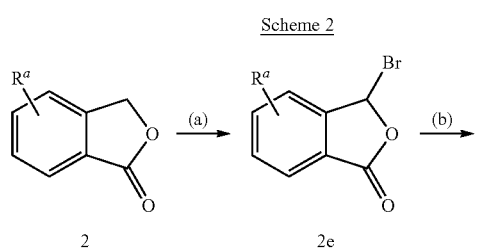

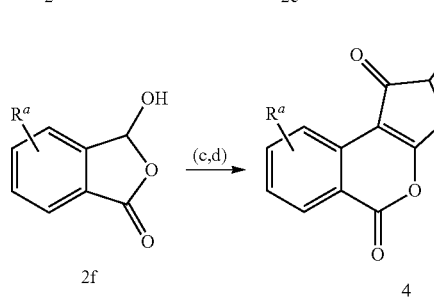

In another illustrative embodiment, a novel, one-pot two-step process for preparing substituted benz[d]indeno[1,2-b]pyran-5,11-diones 4 is described. As shown in Scheme 3, condensation of optionally substituted 2-carboxybenzaldehydes 1 and optionally substituted phthalides 2 in methanol/ethyl acetate with sodium methoxide (step (a)) generates intermediates 3, which are cyclized without isolation in acidified, refluxing benzene or via dicyclohexylcarbodiimide and dimethylaminopyridine (step (b)) to provide optionally substituted indenobenzopyrans 4, where $R^a$ and $R^d$ are as defined herein.

Scheme 3

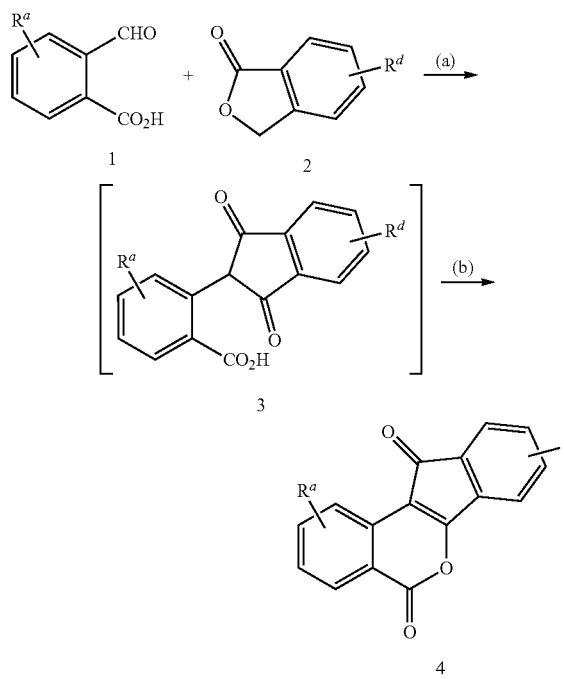

In another illustrative embodiment, indenoisoquinoline compounds of formula I are prepared as outlined in Scheme 4.

Treatment of the indenobenzopyrans 4 in chloroform with a primary amine of the formula $R^6$—$(CH_2)_m$—$NH_2$ (step (a)), where $R^6$ and m are as defined herein, results in the formation of the corresponding indenoisoquinolines 5, where $R^a$, $R^d$, m, and $R^6$ are as defined herein.

Scheme 4

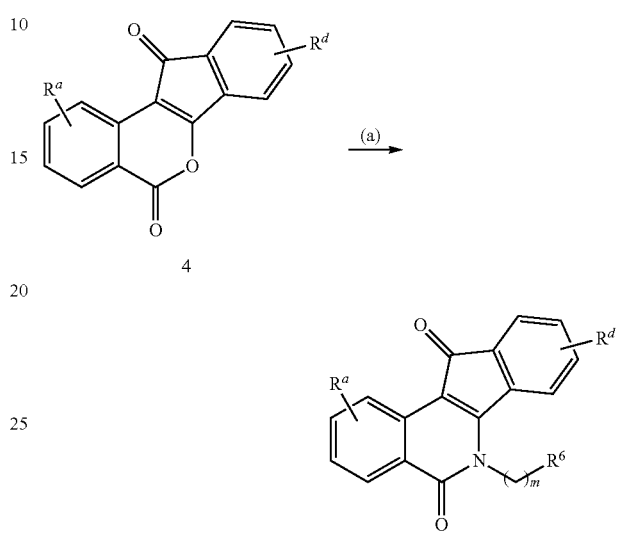

It is appreciated that although chloroform at room temperature will suffice as the solvent for most primary amines, when a primary amine such as a mono-Boc-protected diamine, for example, is used to form the lactam from a benz[d]indeno[1,2-b]pyran-5,11-dione 4, chloroform at reflux may be used as the solvent. It is further appreciated that an indenoisoquinoline compound 5 for which the integer m is not 0, and wherein $R^6$ is halo, azido, or cyano, for example, may be further elaborated through displacement of the halo, azido, or cyano functionality, respectively, with a variety of nucleophiles. Illustratively, treatment of indenobenzopyran 4 in chloroform with 3-(bromo)propylamine (step (a)), i.e., a primary amine where $R^6$ and m in the formula $R^6$—$(CH_2)_m$—$NH_2$ are bromo and 3, respectively, results in the formation of the corresponding N-(3-bromo-1-propyl)indenoisoquinoline 5, which compound can be treated with sodium azide or sodium cyanide in DMSO or with primary and secondary amines, such as ethanolamine, imidazole, N,N-dimethylamine, morpholine, piperazine, and the like, in refluxing dioxane, with concomitant displacement of bromide ion. An N-(3-cyano-1-propyl)indenoisoquinoline 5 may be converted to a variety of carboxylic acid derivatives, including, for example, esters, amides, acid chlorides, and the like.

In another illustrative embodiment, indenoisoquinoline compounds of formula I are prepared as outlined in Scheme 5. Condensation of optionally substituted homophthalic anhydrides 6 with optionally substituted. Schiff bases 7, where $R^a$, $R^d$, m, and $R^6$ are as defined herein, generates carboxylic acids 8 (step (a)), for which the indicated cis stereochemical relationship is based on the observed coupling constant of ~6 Hz for the two methine protons. (Carboxylic acids 9, with a trans stereochemical relationship, would be expected to display a coupling constant on the order of ~10-12 Hz for the two methine protons.) Subjecting carboxylic acids 8 to oxidative Friedel-Crafts ring closure with thionyl chloride and aluminum chloride (step (b)) provides indenoisoquinolines 5, where $R^a$, $R^d$, m, and $R^6$ are as defined herein.

Scheme 5

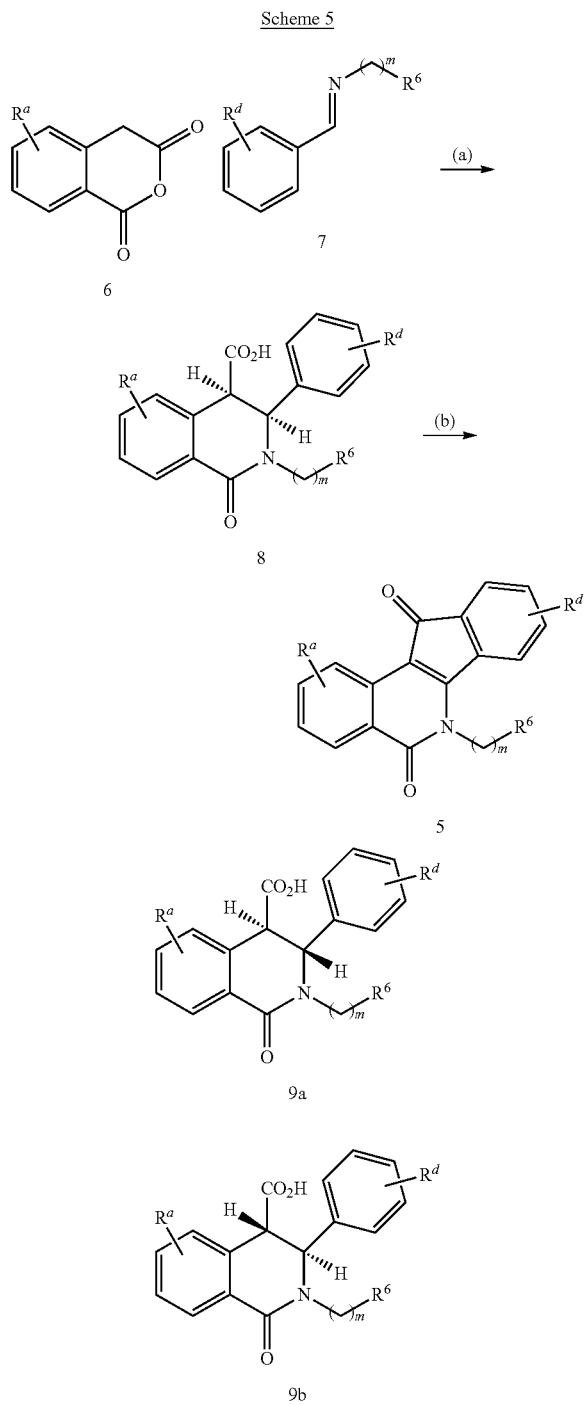

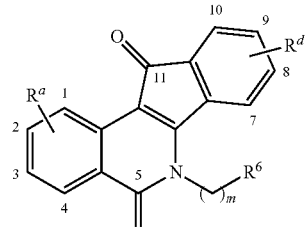

(I)

| Compound | $R^a$ | $R^d$ |
|---|---|---|
| 10a | 2,3-(MeO)$_2$ | 8,9-(MeO)$_2$ |
| 10b | 2,3-(MeO)$_2$ | 8,9-(OCH$_2$O) |
| 10c | 2,3-(MeO)$_2$ | 7,8,9-(MeO)$_3$ |
| 10d | 2,3-(OCH$_2$O) | 8,9-(MeO)$_2$ |
| 10e | 2,3-(OCH$_2$O) | 8,9-(OCH$_2$O) |
| 10f | 2,3-(OCH$_2$O) | 7,8,9-(MeO)$_3$ |
| 10g | 1,2,3-(MeO)$_3$ | 8,9-(MeO)$_2$ |
| 10h | 1,2,3-(MeO)$_3$ | 8,9-(OCH$_2$O) |
| 10i | 1,2,3-(MeO)$_3$ | 7,8,9-(MeO)$_3$ |
| 10j | 1,4-(MeO)$_2$ | 8,9-(MeO)$_2$ |
| 10k | 1,4-(MeO)$_2$ | 8,9-(OCH$_2$O) |
| 10l | 1,4-(MeO)$_2$ | 7,8,9-(MeO)$_3$ |
| 10m | 2,3,4-(MeO)$_3$ | 8,9-(MeO)$_2$ |
| 10n | 2,3,4-(MeO)$_3$ | 8,9-(OCH$_2$O) |
| 10o | 2,3,4-(MeO)$_3$ | 7,8,9-(MeO)$_3$ |

In another illustrative embodiment, novel compounds of formula II are described

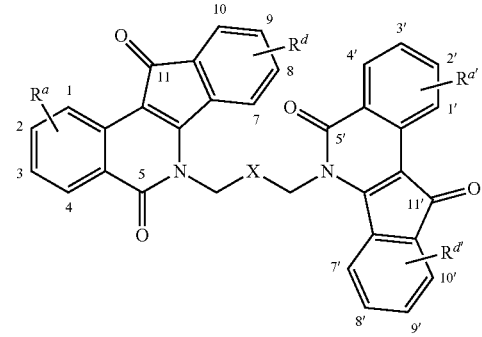

(II)

and pharmaceutically acceptable salts, hydrates, and solvates thereof, wherein:

$R^a$, $R^d$, $R^{a'}$, and $R^{d'}$ independently represent 4 substituents, all of which are independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or where 2 of said substituents are adjacent substituents and are taken together with the attached carbons to form an optionally substituted heterocycle; and In another illustrative embodiment, indenoisoquinoline compounds 10a-10o are described, where the various aspects and embodiments of m and $R^6$ are as described herein, and $R^a$ and $R^d$ are as indicated in the following table:

X is a divalent linker comprising one or more divalent radicals selected from —(CR$^1$R$^2$)—, —(NR$^1$)— and —O—, where $R^1$ and $R^2$ are independently selected in each occurrence from hydrogen, alkyl, and acyl, providing that the divalent linker does not include —O—O—. In one aspect, if present, each divalent —(NR$^1$)— and —O— is separated by at least one divalent radical (—CR$^1$R$^2$)—. In another aspect, each R$^1$ and R$^2$ is hydrogen.

In another illustrative embodiment, X is a group having the general structure —(CH$_2$)$_n$—[(CH$_2$)$_x$—NR$^1$—(CH$_2$)$_y$]$_z$—(NR$^2$)$_p$—(CH$_2$)$_q$—, where n is 0 or 1, x and y are integers independently ranging from 1 to about 4, z is an integer ranging from 1 to about 4, p is 0 or 1, q is 0 or an integer ranging from 1 to about 2, and where R$^1$ and R$^2$ are independently selected in each instance from hydrogen, methyl, t-butyloxycarbonyl, benzyloxycarbonyl, and fluorenylmethoxycabonyl, or R$^1$ and R$^2$ and any adjacent R$^2$ together with the attached nitrogens form a heterocycle.

In one illustrative embodiment of the compounds of formula II, R$^a$ and R$^{a'}$ independently represent one or more substituents selected from optionally substituted alkoxy. In one aspect, R$^a$ and R$^{a'}$ independently represent at least two adjacent substituents taken together to form alkylenedioxy. In another embodiment, R$^a$ and R$^{a'}$ independently represent one or more substituents selected from halo, hydroxy, amino, alkyl and dialkylamino, nitroso, nitro, hydroxylamino, alkoxylamino, and cyano. In another embodiment of the compounds of formula II, R$^d$ and R$^{d'}$ independently represent one or more substituents selected from optionally substituted alkoxy. In one aspect, R$^d$ and R$^{d'}$ independently represent at least two adjacent substituents taken together to form alkylenedioxy. In another embodiment, R$^d$ and R$^{d'}$ independently represent one or more substituents selected from halo, amino, alkyl and dialkylamino, nitroso, nitro, and cyano.

In another illustrative embodiment of the compounds of formula II, n, p, and q are 0, and z is 2, 3, or 4. In another aspect, n and p are 1, z is 1, and q is 2. In one aspect, R$^a$ and R$^{a'}$ independently represent one or more substituents selected from optionally substituted alkoxy. In another aspect, R$^a$ and R$^{a'}$ independently represent at least two adjacent substituents taken together to form alkylenedioxy. In another aspect, R$^a$ and R$^{a'}$ independently represent one or more substituents selected from halo, hydroxy, amino, alkyl and dialkylamino, nitroso, nitro, hydroxylamino, alkoxylamino, and cyano. In another aspect, R$^d$ and R$^{d'}$ independently represent one or more substituents selected from optionally substituted alkoxy. In another aspect, R$^d$ and R$^{d'}$ independently represent at least two adjacent substituents taken together to form alkylenedioxy. In another aspect, R$^d$ and R$^{d'}$ independently represent one or more substituents selected from halo, amino, alkyl and dialkylamino, nitroso, nitro, and cyano.

In another illustrative embodiment, bisindenoisoquinoline compounds 12-17 are described. These compounds were prepared by the processes described herein comprising the steps of preparing and aminolyzing, with a suitable polyamine, a benz[d]indeno[1,2-b]pyran-5,11-dione 4 as described herein.

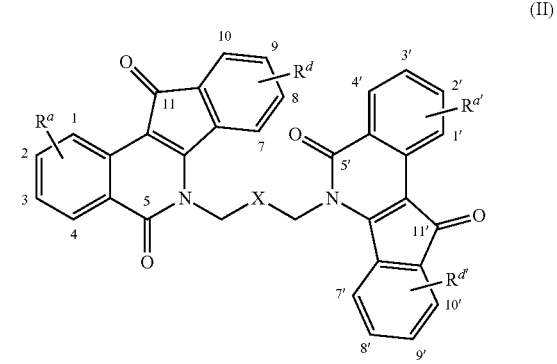

(II)

| Cpd | R$^a$ | R$^{a'}$ | R$^d$ | R$^{d'}$ | -X- |
|---|---|---|---|---|---|
| 12a | H | H | H | H | CH$_2$NHCH$_2$ |
| 12b | H | H | H | H | CH$_2$CH$_2$NHCH$_2$ |
| 12c | H | H | H | H | CH$_2$CH$_2$NHCH$_2$CH$_2$ |
| 12d | H | H | H | H | CH$_2$CH$_2$N(CH$_3$)CH$_2$CH$_2$ |
| 12e | H | H | H | H | CH$_2$CH$_2$NHCH$_2$CH$_2$CH$_2$ |
| 12f | H | H | H | H | CH$_2$NH(CH$_2$)$_2$NHCH$_2$ |
| 12g | H | H | H | H | CH$_2$NH(CH$_2$)$_3$NHCH$_2$ |
| 12h | H | H | H | H | CH$_2$CH$_2$NH(CH$_2$)$_2$NHCH$_2$CH$_2$ |
| 12i | H | H | H | H | CH$_2$CH$_2$N(CH$_2$CH$_2$)$_2$NCH$_2$CH$_2$ |
| 12j | H | H | H | H | CH$_2$CH$_2$NH(CH$_2$)$_3$NHCH$_2$CH$_2$ |
| 12k | H | H | H | H | CH$_2$CH$_2$NH(CH$_2$)$_4$NHCH$_2$CH$_2$ |
| 12l | H | H | H | H | CH$_2$NH(CH$_2$)$_2$NH(CH$_2$)$_2$NHCH$_2$ |
| 12m | H | H | H | H | CH$_2$NH(CH$_2$)$_2$NH(CH$_2$)$_2$NHCH$_2$NHCH$_2$ |
| 13a | H | H | H | H | CH$_2$NBoc(CH$_2$)$_3$NBocCH$_2$ |
| 13b | H | H | H | H | CH$_2$CH$_2$NBoc(CH$_2$)$_2$NBocCH$_2$CH$_2$ |
| 13c | H | H | H | H | CH$_2$CH$_2$NBoc(CH$_2$)$_3$NBocCH$_2$CH$_2$ |
| 13d | H | H | H | H | CH$_2$CH$_2$NBoc(CH$_2$)$_4$NBocCH$_2$CH$_2$ |
| 13e | H | H | H | H | CH$_2$NBoc(CH$_2$)$_2$NBoc(CH$_2$)$_2$NBocCH$_2$ |
| 13f | H | H | H | H | CH$_2$NBoc(CH$_2$)$_2$NBoc(CH$_2$)$_2$NBoc(CH$_2$)$_2$NBocCH$_2$ |
| 14a | H | H | H | H | CH$_2$CH$_2$NHCH$_2$•TFA |
| 14b | H | H | H | H | CH$_2$CH$_2$NHCH$_2$CH$_2$CH$_2$•HCl |
| 14c | H | H | H | H | CH$_2$NH(CH$_2$)$_2$NHCH$_2$•2 TFA |
| 14d | H | H | H | H | CH$_2$NH(CH$_2$)$_3$NHCH$_2$•2 TFA |
| 14e | H | H | H | H | CH$_2$CH$_2$NH(CH$_2$)$_2$NHCH$_2$CH$_2$•2 TFA |
| 14f | H | H | H | H | CH$_2$CH$_2$N(CH$_2$CH$_2$)$_2$NCH$_2$CH$_2$•2 TFA |
| 14g | H | H | H | H | CH$_2$CH$_2$NH(CH$_2$)$_3$NHCH$_2$CH$_2$•2 TFA |
| 14h | H | H | H | H | CH$_2$CH$_2$NH(CH$_2$)$_4$NHCH$_2$CH$_2$•2 TFA |
| 14i | H | H | H | H | CH$_2$NH(CH$_2$)$_2$NH(CH$_2$)$_2$NHCH$_2$•3 TFA |
| 14j | H | H | H | H | CH$_2$NH(CH$_2$)$_2$NH(CH$_2$)$_2$NHCH$_2$NHCH$_2$•4 TFA |
| 14k | 2,3-(MeO)$_2$ | 2,3-(MeO)$_2$ | H | H | CH$_2$NH(CH$_2$)$_3$NHCH$_2$•2 TFA |
| 14l | 2,3-(MeO)$_2$ | 2,3-(MeO)$_2$ | H | H | CH$_2$CH$_2$NH(CH$_2$)$_3$NHCH$_2$CH$_2$•2 TFA |
| 14m | 3-NO$_2$ | 3-NO$_2$ | H | H | CH$_2$NH(CH$_2$)$_3$NHCH$_2$•2 TFA |
| 14n | 3-NO$_2$ | 3-NO$_2$ | H | H | CH$_2$CH$_2$NH(CH$_2$)$_3$NHCH$_2$CH$_2$•2 TFA |

-continued

| Cpd | $R^a$ | $R^a$ | $R^d$ | $R^d$ | -X- |
|---|---|---|---|---|---|
| 15a | 2,3-(MeO)$_2$ | H | 8,9-OCH$_2$O | H | CH$_2$CH$_2$NH(CH$_2$)$_3$NHCH$_2$CH$_2$ |
| 16a | 2,3-(MeO)$_2$ | H | 8,9-OCH$_2$O | H | CH$_2$CH$_2$NBoc(CH$_2$)$_3$NBocCH$_2$CH$_2$ |
| 17a | 2,3-(MeO)$_2$ | H | 8,9-OCH$_2$O | H | CH$_2$CH$_2$NH(CH$_2$)$_3$NHCH$_2$CH$_2$·2 TFA |

It is appreciated that compounds 12-17 may be chemically more stable than camptothecin, owing, at least in part, to the absence of the lactone ring. See, (a) Jaxel, C.; Kohn, K. W.; Wani, M. C.; Pommier. Y. Structure-Activity Study of the Actions of Camptothecin Derivatives on Mammalian Topoisomerase 1: Evidence for a Specific Receptor Site and a Relation to Antitumor Activity *Cancer. Rev.* 1989, 49, 1465-1469. (b) Minanri, H.; Beijnen, J. H.; Verweij, J.; Ratain, M. J. Limited Sampling Model for the Area under the Concentration Time Curve of Total Topotecan *Clin. Cancer Res.* 1996, 2, 43.46. (c) Danks, M. K.; Pawlik, C. A.; Whipple, D, O.; Wolverton, J. S. Intermittant Exposure of Medulloblastoma Cells to Topotecan Produces Growth Inhibition equivalent to Continuous Exposure *Curr. Topics Med. Chem.* 1997, 3, 1731-1738. (d) Haas. N. B.; LaCreta, F. P.; Walczak, J.; Hudes, G. R.; Brennan, J. M.; Ozols, R. F.; O'Dwyer, P. J. PhaseI/Pharmaco-kinetic Study of Topotecan by 24-Hour Continuous Infusion Weekly *Cancer Res.* 1994, 54, 1220-1226, the disclosures of which are incorporated herein by reference. It is further appreciated that compounds 12-17 may be efficacious against various types of human cancers. It is also appreciated that compounds 12-17 may have unique DNA binding site selectivities relative to camptothecin.

In another illustrative embodiment, symmetrical bisindenoisoquinoline compounds of formula II are prepared as outlined in Scheme 6. Treatment of the indenobenzopyrans 4 in refluxing chloroform with a polyamine of the formula NH$_2$—(CH$_2$)$_n$—[(CH$_2$)$_x$—NR$^1$—(CH$_2$)$_y$]$_z$—(NR$^2$)$_p$—(CH$_2$)$_q$—NH$_2$ 11 (step (a)), where R$^1$, R$^2$, n, x, y, z, p, and q are as defined herein, results in the formation of the corresponding bisindenoisoquinolines 12, where R$^a$, R$^d$, R$^{a'}$, R$^{d'}$, and X are as defined herein. If necessary or desired, bisindenoisoquinolines 12 are converted to their respective t-butyloxycarbonyl (Boc-) derivatives 13 upon treatment with Boc anhydride and triethylamine (step (b)), then purified and treated with trifluoroacetic acid or hydrochloric acid (step (c)) to produce the corresponding TFA or HCl salt 14.

Scheme 6

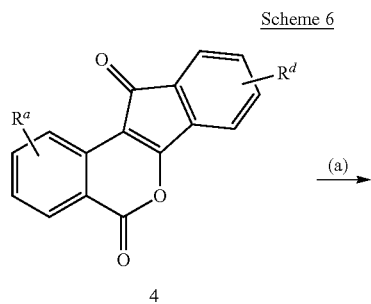

4

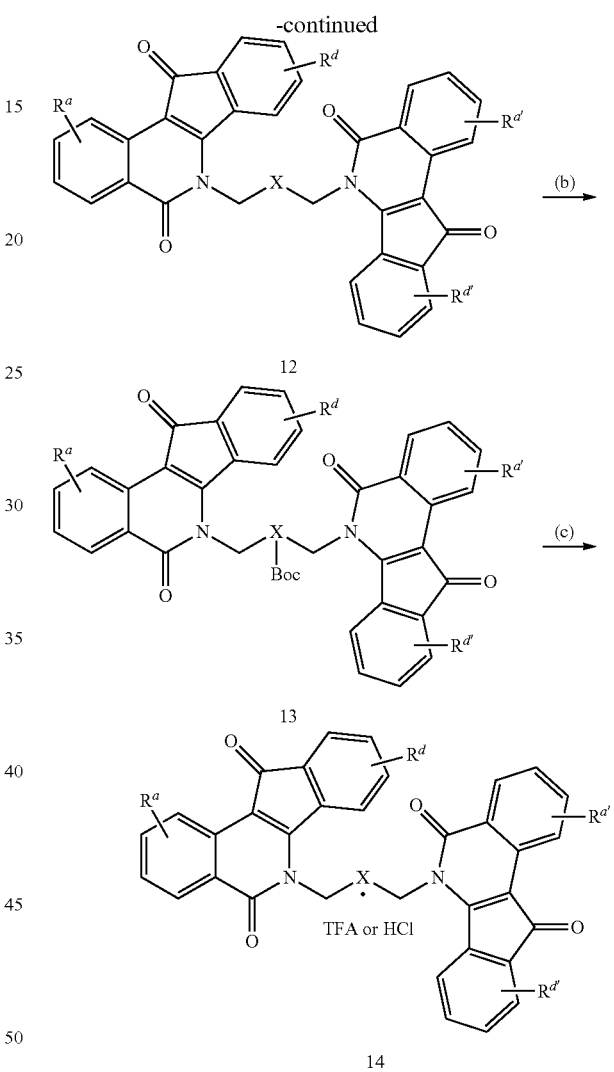

In another illustrative embodiment, unsymmetrical bisindenoisoquinolines of formula II are prepared as outlined in Scheme 7. Treatment of the indenobenzopyrans 4 with a polyamine of the formula NH$_2$—(CH$_2$)$_n$—[(CH$_2$)$_x$—NR$^1$—(CH$_2$)$_y$]$_z$—(NR$^2$)$_p$—(CH$_2$)$_q$—NH$_2$ 11 (step (a)), where R$^2$, n, x, y, z, p, and q are as defined herein, results in the formation of the corresponding polyaminoindenoisoquinoline A, where R$^a$, R$^d$, and X are as defined herein. Subsequent condensation of polyaminoindenoisoquinoline A with indenobenzopyran 4d (step (b)) results in the formation of the corresponding unsymmetrical bisindenoisoquinolines 15. If necessary or desired, unsymmetrical bisindenoisoquinolines 15 are converted to their respective t-butyloxycarbonyl (Boc-) derivatives 16 upon treatment with Boc anhydride and triethylamine (step (c)), then purified and treated with trifluoroacetic acid or hydrochloric acid (step (d)) to produce the corresponding TFA or HCl salt 17.

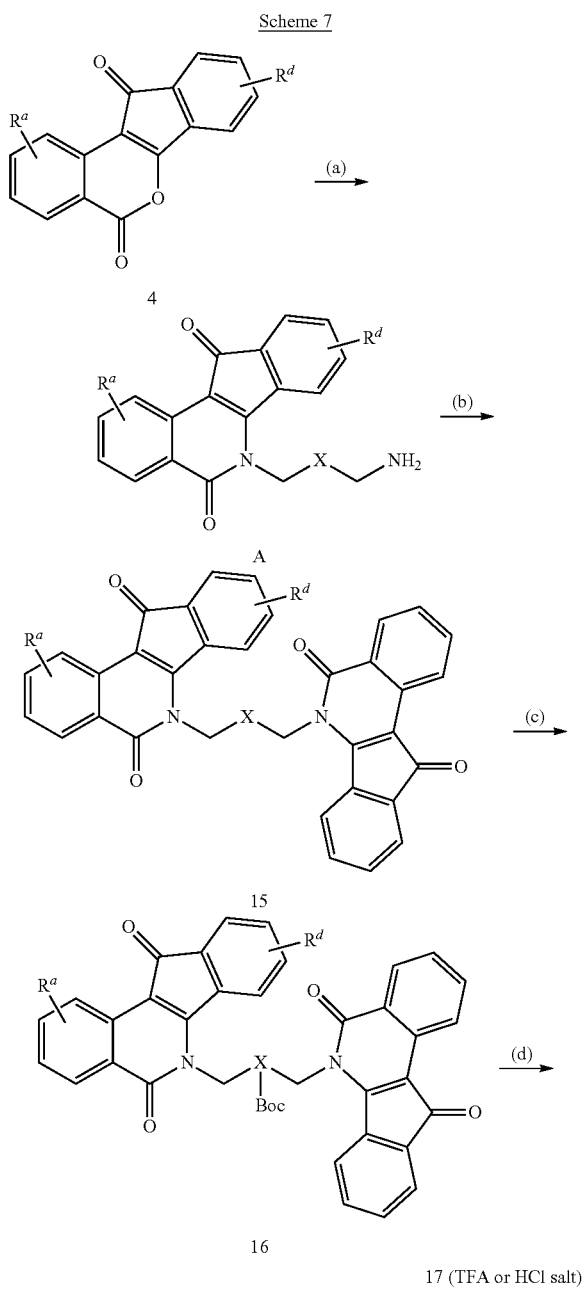

It is appreciated that bisindenoisoquinolines 12 and 15 may be converted to other acyl derivatives, including urethane derivatives such as, for example, benzyloxycarbonyl or fluorenylmethoxycarbonyl derivatives, then purified and deprotected via hydrogenolysis or treatment with piperidine, respectively.

In another illustrative embodiment, novel indenoisoquinoline compounds 18-31 are described. The synthesis of indenoisoquinoline 18 is performed according to a reported method with some modifications (Cinelli, et al. *J. Med. Chem.* 2012, 55, 10844-10862). Amine compound 22, which has a three-carbon side chain, is first prepared using the synthetic route shown in Scheme 8. Treatment of 18 with 1,3-dibromopropane in DMF in the presence of sodium hydride provides the alkylation product 19, accompanied by smaller amounts of the allyl compound 20 as a side product. Displacement of the bromide of compound 19 by sodium azide yields intermediate 21, which is converted to amine 22 by Staudinger reduction.

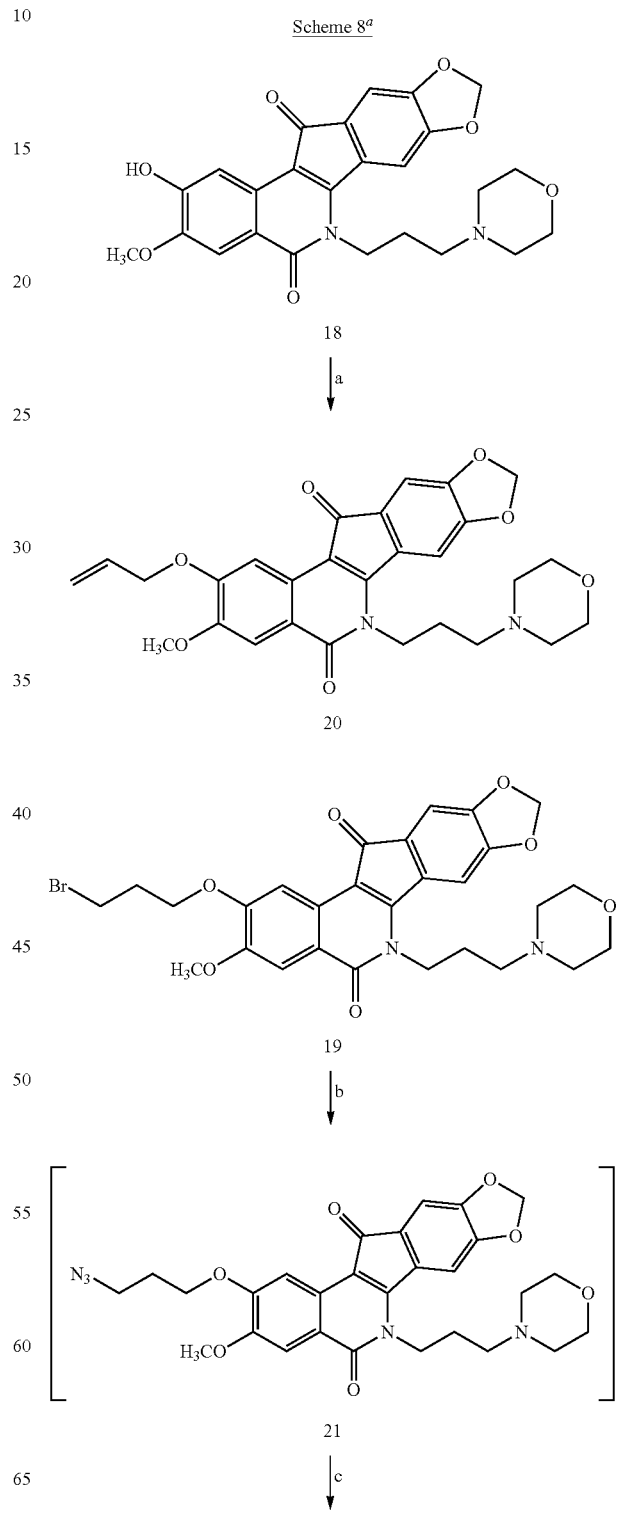

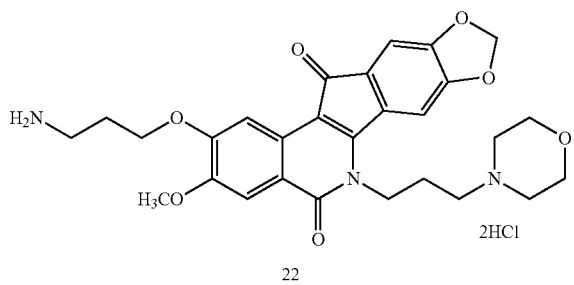

22

<sup>a</sup>Reagents and conditions: (a) NaI, 1,3-dibromopropane, DMF, rt, 3 h; (b) NaN3, DMSO, 100° C., 2 h; (c) (i) triethyl phosphite, benzene, reflux, 16 h, (ii) benzene, HCl in MeOH (2M), reflux, 3 h.

Subsequently, as shown in Scheme 9, the dimethylamino analogue 23 is synthesized by treatment of compound 19 with dimethylamine in the presence of sodium iodide. Similarly, compound 19 reacts with ethylamine in refluxing dioxane to afford compound 24. Treatment of compound 19 with morpholine and sodium iodide gives compound 25. Compound 26 is prepared by treatment of bromide compound 19 with N-methylpiperazine in the presence of sodium iodide. It is assumed that the C-2 terminal amine appendages would be protonated at physiological pH, and that the ammonium cations would form a salt bridge with the Asp533 carboxylate anion of topoisomerase I.

Scheme 9<sup>a</sup>

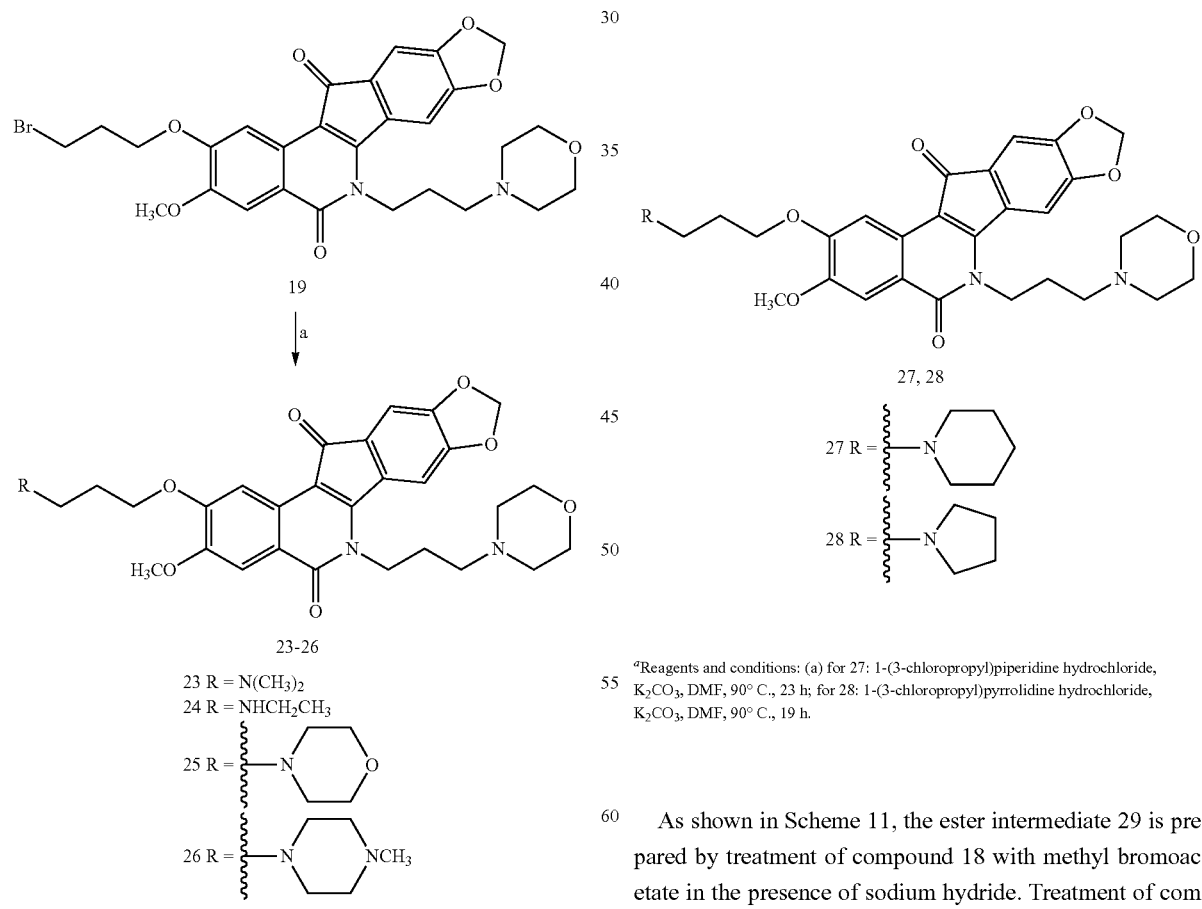

<sup>a</sup>Reagents and conditions: (a) for 23: NaI, dimethylamine, dioxane, reflux, 52 h; for 24: NaI, ethylamine, dioxane, reflux, 26 h; for 25: NaI, morpholine, dioxane, reflux, 24 h; for 26: NaI, N-methyl piperazine, dioxane, reflux, 24 h.

As illustrated in Scheme 10, a different synthetic route is employed for the synthesis of compounds 27 and 28. The 2-hydroxylated indenoisoquinoline 18 reacts with 1-(3-chloropropyl)piperidine hydrochloride in the presence of potassium carbonate to provide compound 27 directly. Similarly, compound 28 is made by treatment of the indenoisoquinoline 18 with 1-(3-chloropropyl)pyrrolidine hydrochloride in the presence of potassium carbonate (Scheme 10).

Scheme 10<sup>a</sup>

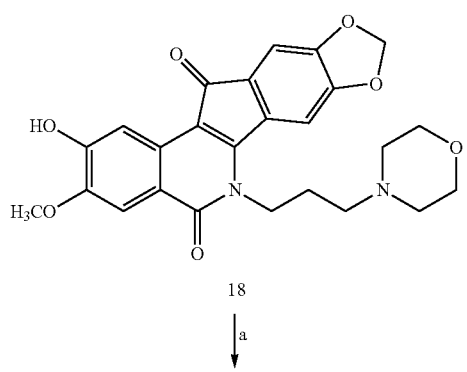

<sup>a</sup>Reagents and conditions: (a) for 27: 1-(3-chloropropyl)piperidine hydrochloride, K2CO3, DMF, 90° C., 23 h; for 28: 1-(3-chloropropyl)pyrrolidine hydrochloride, K2CO3, DMF, 90° C., 19 h.

As shown in Scheme 11, the ester intermediate 29 is prepared by treatment of compound 18 with methyl bromoacetate in the presence of sodium hydride. Treatment of compound 29 with hydrazine does not afford the expected compound 30, but unexpectedly yields the reduced 11-hydroxyl compound 31 instead (Scheme 11).

Scheme 11

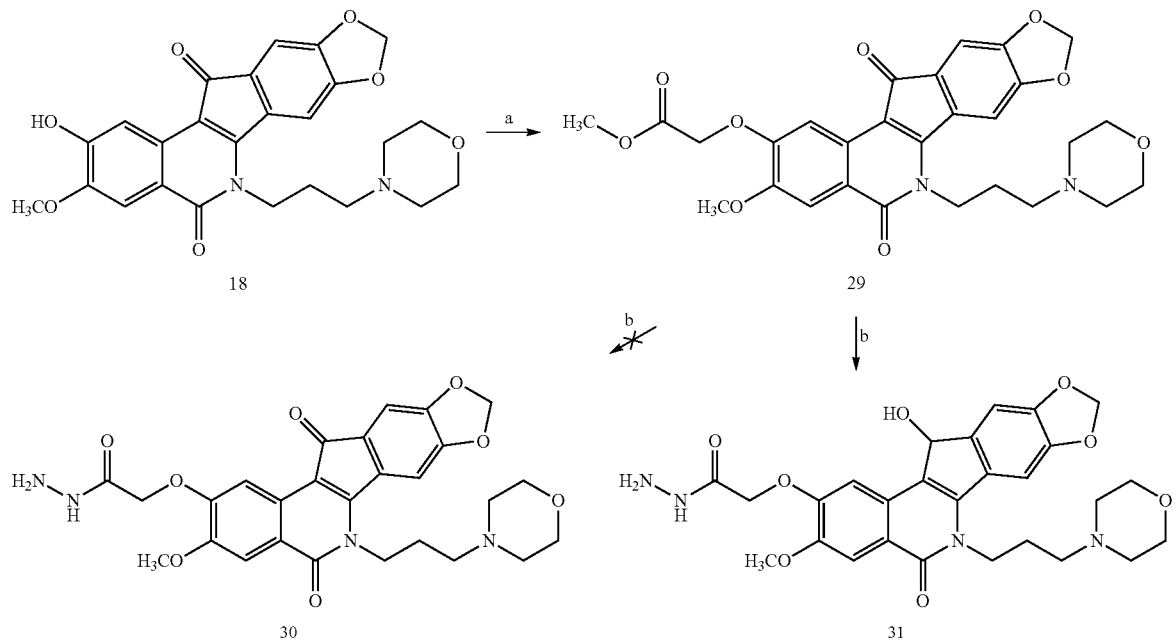

[a]Reagents and conditions: (a) NaH, methyl bromoacetate, DMF, rt, 25 h; (b) hydrazine, EtOH, reflux, 16 h.

The indenoisoquinoline and bisindenoisoquinoline compounds described herein may also form hydrates and solvates. Hydrates may be formed spontaneously upon exposure to ambient conditions where the humidity is sufficient to hydrate the compounds. In addition, hydrates may be formed with more specificity by exposing the compounds described herein to particular humidity conditions. Hydrates may also be formed with by dissolving or suspending the compounds in media containing a predetermined amount of water and evaporating, lyophilizing, or otherwise concentrating such solutions in a manner to give a hydrate form of the compounds described herein. Solvates of the indenoisoquinolinium and bisindenoisoquinolinium compounds described herein may also be formed by dissolving or suspending the compounds in a solvent that is capable of forming a complex with the compound, and subsequently evaporating or otherwise concentrating such solutions in a manner to give a solvate form of the compounds described herein. Solvents capable of forming solvates may include alcohols, such as ethanol, butanol, and the like. It is appreciated that both hydrates and solvates of the compounds described herein may have a predetermined stoichiometry. Such stoichiometry may be evaluated by conventional analytical techniques, including X-ray diffraction, melting analysis, and the like.

The indenoisoquinoline and bisindenoisoquinoline compounds described herein may form pharmaceutically acceptable salts. As used herein, the term "pharmaceutically acceptable salts" refers to derivatives of the disclosed indenoisoquinoline and bisindenoisoquinoline compounds wherein the parent compound is modified by converting an existing acid or base moiety to its salt form. Examples of pharmaceutically acceptable salts of indenoisoquinoline and bisindenoisoquinoline compounds described herein include, but are not limited to, mineral or organic acid salts of basic residues such as amines; alkali or organic salts of acidic residues such as carboxylic acids; and the like. The pharmaceutically acceptable salts include the non-toxic salts or the quaternary ammonium salts of the parent compound formed, for example, from non-toxic inorganic or organic acids. For example, such non-toxic salts include those derived from inorganic acids such as hydrochloric acid or any inorganic acids known in the art, or organic acids such as tartaric acid, lactic acid, or any organic acid known in the art. The pharmaceutically acceptable salts of indenoisoquinoline and bisindenoisoquinoline compounds described herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile, are preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds described herein show antineoplastic activity using the COMPARE screening methodology, demonstrating that they are antineoplastic agents useful in treating human cancers. The compounds described herein are inhibitors of topoisomerase I (top1), and in particular may be inhibitors of the top1-catalyzed DNA religation reaction. Such inhibition may account for the antiproliferative activity against cancer cells that compounds described herein show in vitro. The compounds described herein may form ternary complexes consisting of the compound, DNA, and the top1 enzyme. Without being bound by theory, it is believed that the compounds described herein may be operating as top1 poisons, which inhibit the top1 enzyme catalyzed DNA religation reaction. It is further appreciated that the compounds described herein may have longer in vitro and in vivo activity than conventional treatments if the formation of the ternary complexes is not reversible or rapidly reversible.

Therefore, some of the growth inhibition demonstrated through COMPARE testing may occur through that mechanism of action, inhibition of topoisomerase I. However, it is appreciated that compounds showing surprisingly potent cell growth inhibition, even though their inhibitory effects on topoisomerase I are relatively small in comparison to other agents tested, may cause inhibition of cell growth, at least in part, through another mechanism of action in addition to or instead of inhibition of topoisomerase I.

Also described herein are pharmaceutical compositions and formulations comprising a therapeutically effective amount of one or more indenoisoquinoline or bisindenoisoquinoline compounds for treating a patient having cancer. It is appreciated that mixtures of certain indenoisoquinoline or bisindenoisoquinoline compounds may be administered. Such pharmaceutical compositions may also include one or more diluents, carriers, and/or excipients. As used herein, an effective amount of the indenoisoquinoline or bisindenoisoquinoline compound is defined as the amount of the compound which, upon administration to a patient, inhibits growth of cancer cells, kills malignant cells, reduces the volume or size of the tumors, and/or eliminates the tumor entirely in the treated patient. It is to be understood that treated patients include humans and other mammals.

As used herein, the term "therapeutically effective amount" refers to the amount to be administered to a patient, and may be based on body surface area, patient weight, and/or patient condition. In addition, it is appreciated that there is an interrelationship of dosages determined for humans and those dosages determined for animals, including test animals (illustratively based on milligrams per meter squared of body surface) as described by Freireich, E. J., et al., *Cancer Chemother. Rep.* 1966, 50 (4), 219, the disclosure of which is incorporated herein by reference. Body surface area may be approximately determined from patient height and weight (see, e.g., Scientific Tables, Geigy Pharmaceuticals, Ardley, N.Y., pages 537-538 (1970)). A therapeutically effective amount of the indenoisoquinoline and bisindenoisoquinoline compounds described herein may be defined as any amount useful for inhibiting the growth of (or killing) a population of malignant cells or cancer cells, such as may be found in a patient in need of relief from such cancer or malignancy. Such effective amounts range from about 5 mg/kg to about 500 mg/kg, from about 5 mg/kg to about 250 mg/kg, and/or from about 5 mg/kg to about 150 mg/kg of indenoisoquinoline compounds per patient body weight. In some embodiments, a dose in a human is approximately 10-100 mg per meter of surface area squared ($mg/m^2$), for example, from about 10 $mg/m^2$ to about 75 $mg/m^2$, or from about 10 $mg/m^2$ to about 50 $mg/m^2$, or from about 10 $mg/m^2$ to about 25 $mg/m^2$, or from 25 $mg/m^2$ to about 100 $mg/m^2$, or from 25 $mg/m^2$ to about 75 $mg/m^2$, or from 25 $mg/m^2$ to about 50 $mg/m^2$, or from 50 $mg/m^2$ to about 100 $mg/m^2$, or from 50 $mg/m^2$ to about 75 $mg/m^2$. It is appreciated that effective doses may also vary depending on the route of administration, optional excipient usage, and the possibility of co-usage of the indenoisoquinoline compounds with other conventional and non-conventional therapeutic treatments, including other anti-tumor agents, radiation therapy, and the like.

The indenoisoquinoline and bisindenoisoquinoline compounds may be administered in a variety of pharmaceutical formulations, including conventional pharmaceutical formulations. The indenoisoquinoline compounds, and formulated variants thereof, may also be delivered by a variety of administration routes, including conventional delivery routes. In one embodiment, the indenoisoquinoline compounds, and formulated variants thereof, are delivered via a parenteral route, including subcutaneously, intraperitoneally, intramuscularly, and intravenously. Examples of parenteral dosage forms and formulations include aqueous solutions of the indenoisoquinoline compounds in isotonic saline, 5% glucose or other conventional pharmaceutically acceptable liquid carrier. In one aspect, the one or more indenoisoquinoline compounds are dissolved in a saline solution containing 5% dimethyl sulfoxide and 10% Cremphor EL (Sigma Chemical Company). Additional solubilizing agents such as cyclodextrins, which can form specific, more soluble complexes with the indenoisoquinoline compounds described herein, or other conventional solubilizing agents can be included as pharmaceutical excipients for delivery of the compounds.

In another embodiment, the indenoisoquinoline compounds, bisindenoisoquinoline compounds, and formulated variants thereof, are delivered via oral administration, such as in a capsule, a gel seal, a tablet, and the like. Capsules may comprise any conventional pharmaceutically acceptable material including gelatin and/or cellulose derivatives. Tablets may be formulated by conventional procedures, including by compressing mixtures of the indenoisoquinoline compounds, solid carriers, lubricants, disintegrants and other conventional ingredients for solid dosage forms, such as starches, sugars, bentonite, and the like. The compounds described herein may also be administered in a form of a hard shell tablet or capsule containing, for example, lactose or mannitol as a binder, and conventional fillers and tableting agents. Solid dosage forms described herein and useful for delivering the indenoisoquinoline compounds also include sustained release formulations, such as tablets, caplets, pills, capsules, and the like that include an enteric coating that may delay the release of the indenoisoquinoline compounds until the formulation has passed into the intestinal tract.

The following exemplary embodiments are included herein to further illustrate the invention. These exemplary embodiments are not intended and should not be interpreted to limit the scope of the invention in any way. It is to be understood that numerous variations of the exemplary embodiments are contemplated herein.

Compound Examples

Melting points were determined in capillary tubes and are uncorrected. Infrared spectra were obtained using $CHCl_3$ as the solvent unless otherwise specified. Except where noted, 300 MHz $^1H$ NMR spectra were obtained using $CDCl_3$ as solvent and the solvent peak as internal standard. Mass spectra were determined by electrospray mass spectrometry. Microanalyses were performed at the Purdue University Microanalysis Laboratory. Reactions were generally monitored by analytical thin-layer chromatography using Bakerflex silica gel IB2-F plates or flexible sheets, visualized with short wavelength UV light. Silica gel flash chromatography was performed using 230-400 mesh silica gel.

A representative procedure for the one-pot synthesis of an indenobenzopyran 4 is described herein for benz[d]indeno[1,2-b]pyran-5,11-dione 4d. It is understood that other indenobenzopyrans, including compounds 4a-4s, may be prepared according to this representative example. In addition, a representative procedure for the synthesis of an indenoisoquinoline 5 from indenobenzopyran 4 and a primary amine is described herein for 5,6-dihydro-6-(2-morpholin-4-yl-1- ethyl)-3-nitro-5,11-dioxo-11H-indeno[1,2-c]isoquinoline 5i. It is understood that other indenoisoquinolines, including compounds 5a-5k, may be prepared from this representative example. A representative procedure for the synthesis of an indenoisoquinoline 5 by aminolysis of 6-(3-bromo-1-propyl)-5,6-dihydro-2,3-dimethoxy-8,9-methylenedioxy-5,11-dioxo-11H-indeno[1,2-c]isoquinoline 5y is also described herein, by which procedure indenoisoquinolines 5l, and 5o-5x were prepared. In addition, a representative procedure for the synthesis of an indenoisoquinoline 5 from indenobenzopyran 4d and a mono-Boc-protected primary amine is described herein, by which procedure mono-Boc-protected indenoisoquinolines 5aa-5ac, and 5af-5ak were prepared for generation of the corresponding HCl salts 5al-5an and 5aq-5ay. Syntheses of indenoisoquinolines 5aw-5az from indenobenzopyran 4d and a series of aminopyridine derivatives are also described herein. In addition, a representative procedure is described herein for the synthesis of an indenoisoquinoline 5 by i) condensing substituted homophthalic anhydrides 6 with Schiff bases 7 and ii) subjecting the resulting carboxylic acids 8 to oxidative Friedel-Crafts ring closure, by which procedure indenoisoquinolines 5bb-5bc were prepared. It is understood that other indenoisoquinolines, including compounds 5ba, 5bd, and 5be, may be prepared according to this representative example. Indenoisoquinolines 5bf-5bs were prepared from N-haloalkylindenoisoquinolines 5bb, 5bd and 5be by the aminolysis procedure described herein. Also described herein are syntheses of bisindenoisoquinolines 12-17 from indenobenzopyrans 4 and a variety of polyamines 11.

Benz[d]indeno[1,2-b]pyran-5,11-dione (4d). Sodium methoxide (40 mL of a 4 M methanolic solution) was added to a solution of 2-carboxybenzaldehyde 1d (1.000 g, 7.455 mmol) and phthalide 2d (1.119 g, 7.455 mmol) in ethyl acetate (20 mL). The solution was heated at 65° C. for 18 h, concentrated, and acidified with coned HCl. The resulting mixture was diluted with benzene (125 mL), TsOH (100 mg) was added, and the solution was heated for 7 h at reflux in a flask affixed with a Dean-Stark trap. The solution was cooled to room temperature, concentrated, diluted with CHCl$_3$ (150 mL), and washed with sat NaHCO$_3$ (3×50 mL) and sat NaCl (50 mL). The organic layer was dried over sodium sulfate and concentrated to provide indenobenzopyran 4d as an orange solid (1.583 g, 86%): mp 258-259° C. (published mp 257° C.). $^1$H NMR (CDCl$_3$) δ 8.40 (d, J=8.56 Hz, 1H), 8.32 (d, J=7.93 Hz, 1H), 7.84-7.79 (m, 1H), 7.61-7.39 (m, 5H). Additional details regarding the synthesis of compound 8 are found in Pailer et al., *Monatsh Chem.*, 92:1037-47 (1961), the synthetic disclosure of which is incorporated herein by reference.

5,6-Dihydro-6-(2-morpholin-4-yl-1-ethyl)-3-nitro-5,11-dioxo-11H-indeno[1,2-c]isoquinoline (5i). 4-(2-Aminoethyl)morpholine (0.133 g, 1.023 mmol) was added to a solution of 3-nitrobenz[d]indeno[1,2-b]pyran-5,11-dione 4c (0.100 g, 0.341 mmol) in CHCl$_3$ (30 mL). The solution was allowed to stir at room temperature for 16 h, diluted with CHCl$_3$ (110 mL) and washed with H$_2$O (3×30 mL) and sat NaCl (30 mL). The organic layer was dried over sodium sulfate, filtered, and concentrated to provide indenoisoquinoline 9i as a crude solid. The solid was purified by flash column chromatography (SiO$_2$/CHCl$_3$ to 7% MeOH/CHCl$_3$) to provide indenoisoquinoline 5i as an orange solid (0.138 g, 100%): mp 257-259° C. IR (film) 1670, 1613, 1505, 1330, and 1078 cm$^{-1}$; $^1$H NMR (CDCl$_3$) δ 9.20 (s, I H), 8.89 (d, J=Hz, I H), 8.52 (d, J=Hz, 1H), 7.80-7.72 (m, 2H), 7.54 (m, 2H), 4.73 (m, 2H), 3.72 (bs, 4H), 2.83 (m, 2H), 2.62 (bs, 4H); ESIMS m/z (rel intensity) 406 (MH$^+$, 100). Anal. Calcd for C$_{22}$H$_{19}$N$_3$O$_5$: C, 65.18; H, 4.72; N, 10.37. Found: C, 65.27; H, 4.74; N, 10.20.

General Procedure for the Synthesis of Indenoisoquinolines 5l and 5o-5x from 6-(3-bromo-1-propyl)-5,6-dihydro-2,3-dimethoxy-8,9-methylenedioxy-5,11-dioxo-11H-indeno[1,2-c]isoquinoline (5y). A mixture of 6-(3-bromo-1-propyl)-5,6-dihydro-2,3-dimethoxy-8,9-methylenedioxy-5,11-dioxo-11H-indeno[1,2-c]isoquinoline (5y) (0.500 g, 1.06 mmol), amine (2.11 mmol), and anhydrous K$_2$CO$_3$ (0.584 g, 4.23 mmol) in anhydrous 1,4-dioxane (30 mL) was heated at 100° C. for 4 h. The reaction mixture was cooled and then concentrated. The residue was diluted with water (50 mL), extracted with CHCl$_3$ (2×50 mL), washed with 1% aq HCl (50 mL), water (50 mL), sat NaCl (50 mL), and dried over Na$_2$SO$_4$. The crude product was purified by flash column chromatography (SiO$_2$), eluting with a 0-5% gradient of methanol in chloroform, to provide the pure indenoisoquinoline.

3-(Imidazolyl-1-propyl)-5,6-dihydro-2,3-dimethoxy-8,9-methylenedioxy-5,11-dioxo-11H-indeno[1,2-c]isoquinoline Hydrochloride (5l). The desired analogue was obtained as a dark purple solid (245 mg, 63%); mp 316-318° C., $^1$H NMR (CDCl$_3$) δ 8.01 (s, 1H), 7.63 (s, 1H), 7.60 (s, 1H), 7.14 (s, 1H), 7.04 (s, 2H), 6.40 (s, 1H), 6.07 (s, 2H), 4.45 (t, J=5.8 Hz, 2H), 4.20 (t, J=6.6 Hz, 2H), 4.03 (s, 3H), 3.98 (s, 3H), 2.33 (t, J=6.9 Hz, 2H); ESIMS m/z (rel intensity) 460 (MH$^+$, 100). Anal. (C$_{25}$H$_{21}$N$_3$O$_6$.0.2H$_2$O) C, H, N. The hydrochloride salt was formed by dissolving the product in chloroform (50 mL) and an anhydrous solution of 2 M HCl in diethyl ether (15 mL, 30.0 mmol) was added at 0° C. The reaction mixture was stirred at room temperature for 6 h and the precipitated product was filtered and washed with chloroform (50 mL), methanol (20 mL), and dried over P$_2$O$_5$ for 24 h to afford the product as a dark purple solid (170 mg, 79%): mp 270-272° C. $^1$H NMR (DMSO-d$_6$-CD$_3$OD, 2:1) δ 9.07 (s, 1H), 7.78 (s, 2H), 7.60 (s, 1H), 7.42 (s, 1H), 7.14 (s, 1H), 6.96 (s, 1H), 6.13 (s, 2H), 4.41 (t, J=6.6 Hz, 2H), 4.36 (t, J=7.3 Hz, 2H), 3.86 (s, 3H), 3.82 (s, 3H), 2.35 (t, J=6.1 Hz, 2H); ESIMS m/z (rel intensity) 494 (MH$^+$, 100). Anal. (C$_{25}$H$_{22}$N$_3$O$_6$Cl) C, H, N.

6-[3-Pyrazolyl-1-propyl]-5,6-dihydro-2,3-dimethoxy-8,9-methylenedioxy-5,11-dioxo-11H-indeno[1,2-c]isoquinoline (5m). 6-(3-Bromo-1-propyl)-5,6-dihydro-2,3-dimethoxy-8,9-methylenedioxy-5,11-dioxo-11H-indeno[1,2-c]isoquinoline (5y) (0.2113 g, 0.448 mmol) was added to sodium hydride (86.8 mg of a 60% suspension in mineral oil, 2.17 mmol) and pyrazole (0.1749 g, 2.57 mmol) in DMF (50 mL) and the reaction mixture was heated at 60° C. for 4 h. The reaction mixture was diluted with water (200 mL) and extracted with chloroform (200 mL). The organic layer was washed with water (7×200 mL) and concentrated. Benzene was added (2×30 mL) and the mixture was concentrated again. The residue was dissolved in chloroform (4 mL) and diethyl ether (50 mL) was added. The precipitate was washed with diethyl ether (100 mL) and a dark red solid (118.5 mg, 57.6%) was obtained: mp 262-264° C. (dec). IR (film) 3462, 3104, 2918, 1693, 1640, 1557, 1495, 1488, 1430, 1394, 1308, 1284, 1251, 1205, 868, 785, 769 cm$^{-1}$; $^1$H NMR (DMSO-d$_6$) δ 7.97 (s, 1H), 7.65 (d, J=1.5 Hz, 1H), 7.61 (s, 1H), 6.57 (s, 1H), 6.97 (s, 1H), 6.68 (s, 1H), 6.33 (s, 1H), 6.05 (s, 2H), 4.40 (m, 4H), 4.01 (s, 3H), 3.96 (s, 3H), 2.45 (m, 2H); ESIMS m/z (rel intensity) 460 (MH$^+$, 100). Anal. (C$_{25}$H$_{21}$N$_3$O$_6$.0.75H$_2$O) C, H, N.

6-{3-[2-(1,2,4)]-Triazolyl-1-propyl}-5,6-dihydro-2,3-dimethoxy-8,9-methylenedioxy-5,11-dioxo-11H-indeno[1,2-c]isoquinoline Hydrochloride (5n). 6-(3-Bromo-1-propyl)-5,6-dihydro-2,3-dimethoxy-8,9-methylenedioxy-5,11- dioxo-11H-indeno[1,2-c]isoquinoline (5y) (0.2538 g, 0.538 mmol) was added to sodium hydride (124.8 mg of a 60% suspension in mineral oil, 3.12 mmol) and 1,2,4-triazole (0.2673 g, 0.566 mol) in DMF (50 mL) and the reaction mixture was heated at 60° C. for 3 h. The reaction mixture was diluted with water (200 mL) and the precipitate was separated by filtration and washed with water (50 mL). The precipitate was partially dissolved in methanol-chloroform 1:1 (200 mL). Diethyl ether (100 mL) was added and the precipitate was separated by filtration and washed with additional diethyl ether (100 mL) to provide the product as the free base. The residue was dissolved in trifluoroacetic acid (2 mL) and hydrochloric acid (4 mL of a 2 M solution in diethyl ether) was added, followed by more diethyl ether (30 mL). The product was collected as a dark red solid (159.5 mg, 57%): mp>240° C. IR (KBr) 3429, 1694, 1647, 1553, 1500, 1487, 1431, 1394, 1311, 1254, 1207, 1032, 928, 873, 800, 786, 722, 617 cm$^{-1}$; $^1$H NMR (DMSO-d$_6$) δ 8.56 (s, 1H), 7.99 (s, 1H), 7.90 (s, 1H), 7.52 (s, 1H), 7.15 (s, 1H), 7.10 (s, 1H), 6.19 (s, 2H), 4.44-4.38 (m, 4H), 3.90 (s, 3H), 3.86 (s, 3H), 2.25 (m, 2H); ESIMS m/z (rel intensity) 461 (MH$^+$, 53), 392 (MH$^+$-C$_2$N$_3$H$_3$, 100). High resolution ESIMS m/z (rel intensity) 461.1464 (100, MH$^+$) (calculated mass 461.1461).

6-(3-Thiazolylamino-1-propyl)-5,6-dihydro-2,3-dimethoxy-8,9-methylenedioxy-5,11-dioxo-11H-indeno[1,2-c]isoquinoline Dihydrochloride (5o). The product (213 mg, 41%) was dissolved in chloroform (50 mL) and treated with an anhydrous solution of 2 M HCl in diethyl ether (15 mL, 30.0 mmol) at 0° C. The reaction mixture was stirred at room temperature for 6 h and the precipitated product was filtered and washed with chloroform (50 mL), methanol (10 mL), and dried over P$_2$O$_5$ to provide the desired analogue as a pale purple solid (140 mg, 61%): mp 298-300° C. (dec). $^1$H NMR (DMSO-d$_6$) δ 7.82 (s, 1H), 7.44 (s, 1H), 7.38 (s, 1H), 7.04 (s, 1H), 6.18 (s, 2H), 4.42 (bs, 2H), 4.07 (bs, 2H), 3.88 (s, 3H), 3.83 (s, 3H), 3.76 (bs, 4H), 2.07 (bs, 2H); ESIMS m/z (rel intensity) 494 (MH$^+$, 100). Anal. (C$_{25}$H$_{25}$N$_3$O$_6$SCl$_2$.0.6CHCl$_3$) C, H, N.

6-(3-Piperazinyl-1-propyl)-5,6-dihydro-2,3-dimethoxy-8,9-methylenedioxy-5,11-dioxo-11H-indeno[1,2-c]isoquinoline Dihydrochloride (5p). The product (350 mg, 72%) was dissolved in chloroform and treated with 2 M HCl in diethyl ether (9.0 mL, 18.2 mmol) at room temperature to afford the desired analogue as a pale purple solid (280 mg, 84%): mp 276-278° C. (dec). $^1$H NMR (D$_2$O) δ 6.63 (bs, 1H), 6.53 (s, 1H), 6.47 (bs, 1H), 6.18 (s, 1H), 5.91 (s, 2H), 3.90 (bs, 2H), 3.51 (s, 3H), 3.46 (bs, 11H), 3.20 (bs, 2H), 2.02 (bs, 2H); ESIMS m/z (rel intensity) 478 (MH$^+$, 100). Anal. (C$_{26}$H$_{29}$Cl$_2$N$_3$O$_6$. 2.3H$_2$O) C, H, N.

6-[3-(Morpholin-4-yl)-1-propyl]-5,6-dihydro-2,3-dimethoxy-8,9-methylenedioxy-5,11-dioxo-11H-indeno[1,2-c]isoquinoline (5q). The product was isolated as a dark purple solid (0.220 g, 72%): mp 290-292° C. $^1$H NMR (CDCl$_3$) δ 7.98 (s, 1H), 7.59 (s, 1H), 7.36 (s, 1H), 7.02 (s, 1H), 6.07 (s, 2H), 4.48 (t, J=7.39 Hz, 2H), 4.02 (s, 3H), 3.95 (s, 3H), 3.76 (bs, 4H), 2.54 (bs, 6H), 2.01 (bs, 2H); ESIMS m/z (rel intensity) 479 (MH$^+$, 100). Anal. (C$_{26}$H$_{26}$N$_2$O$_7$.0.2H$_2$O) C, H, N.

6-[3-(Thiomorpholin-4-yl)-1-propyl]-5,6-dihydro-2,3-dimethoxy-8,9-methylenedioxy-5,11-dioxo-11H-indeno[1,2-c]isoquinoline (5r). The product was isolated as a dark purple solid (275 mg, 53%): mp 306-308° C. $^1$H NMR (CDCl$_3$) δ 7.80 (s, 1H), 7.60 (s, 1H), 7.33 (s, 1H), 7.04 (s, 1H), 6.08 (s, 2H), 4.48 (t, J=6.4 Hz, 2H), 4.02 (s, 3H), 3.96 (s, 3H), 2.84-2.78 (bs, 8H), 2.67 (bs, 2H), 2.09 (bs, 2H); ESIMS m/z (rel intensity) 495 (MH$^+$, 100). Anal. (C$_{26}$H$_{26}$N$_2$O$_6$S.0.3H$_2$O) C, H, N.

6-[3-(3-Hydroxypiperidinyl)-1-propyl]-5,6-dihydro-2,3-dimethoxy-8,9-methylenedioxy-5,11-dioxo-11H-indeno[1,2-c]isoquinoline Hydrochloride (5s). The product (220 mg, 0.45 mmol, 70%) was treated with 2 M HCl in diethyl ether (4.0 mL, 6.69 mmol) in chloroform at room temperature to afford the desired analogue as a purple solid (210 mg, 89%): mp 288-290° C., $^1$H NMR (D$_2$O) δ 6.54 (bs, 1H), 6.41 (s, 1H), 6.29 (bs, 1H), 6.06 (s, 1H), 5.88 (s, 2H), 3.82 (bs, 2H), 3.45 (s, 3H), 3.37 (bs, 7H), 3.15 (bs, 3H), 1.99 (bs, 4H), 1.68 (bs, 2H); ESIMS m/z (rel intensity) 493 (MH$^+$, 100). Anal. (C$_{27}$H$_{29}$ClN$_2$O$_7$.1.4H$_2$O) C, H, N.

3-[(1-Methylpiperazinyl)-1-propyl]-5,6-dihydro-2,3-dimethoxy-8,9-methylenedioxy-5,11-dioxo-11H-indeno[1,2-c]isoquinoline (5t). The desired analogue was isolated as a dark purple solid (160 mg, 51%): mp 254-256° C. $^1$H NMR (CDCl$_3$) δ 7.99 (s, 1H), 7.60 (s, 1H), 7.30 (s, 1H), 7.03 (s, 1H), 6.08 (s, 2H), 4.47 (t, J=6.0 Hz, 2H), 4.02 (s, 3H), 3.96 (s, 3H), 2.55 (bs, 10H), 2.30 (s, 3H), 1.99 (bs, 2H); ESIMS m/z (rel intensity) 492 (MH$^+$, 100). Anal. (C$_{27}$H$_{29}$N$_3$O$_6$.0.5CHCl$_3$) C, H, N.

6-[3-(4-Aminopiperidinyl)-1-propyl]-5,6-dihydro-2,3-dimethoxy-8,9-methylenedioxy-5,11-dioxo-11H-indeno[1,2-c]isoquinoline Dihydrochloride (5u). The product (205 mg, 66%) was dissolved in chloroform (30 mL) and treated with 2 M HCl in diethyl ether (5.2 mL, 10.40 mmol) at room temperature for 8 h. The precipitate was filtered and washed with chloroform (30 mL) to provide the desired analogue as a dark purple solid (165 mg, 85%): mp 262-264° C. (dec). $^1$H NMR (D$_2$O) δ 6.62 (s, 1H), 6.50 (s, 1H), 6.44 (s, 1H), 6.17 (s, 1H), 5.92 (s, 2H), 3.92 (bs, 2H), 3.64 (bs, 2H), 3.50 (s, 4H), 3.45 (s, 3H), 3.23 (bs, 2H), 3.08 (bs, 2H), 2.25 (m, 2H), 2.06 (bs, 2H), 1.90 (m, 2H); ESIMS m/z (rel intensity) 492 (MH$^+$, 70).

6-(3-Homopiperazinyl-1-propyl)-5,6-dihydro-2,3-dimethoxy-8,9-methylenedioxy-5,11-dioxo-11H-indeno[1,2-c]isoquinoline Dihydrochloride (5v). The obtained product (390 mg, 0.66 mmol, 69%) was dissolved in chloroform and treated with 2 M HCl in diethyl ether (10.0 mL, 19.8 mmol) to afford the desired analogue as a purple solid (305 mg, 82%): mp 264-266° C. (dec). $^1$H NMR (D$_2$O) δ 6.71 (bs, 1H), 6.56 (bs, 2H), 6.21 (bs, 1H), 5.92 (s, 2H), 3.98 (bs, 2H), 163-3.57 (bs, 6H), 3.55 (s, 3H), 3.50 (s, 3H), 3.36-3.25 (bs, 4H), 2.19 (bs, 2H), 2.09 (bs, 2H); ESIMS m/z (rel intensity) 492 (MH$^+$, 100). Anal. (C$_{27}$H$_{31}$Cl$_2$N$_3$O$_6$.0.7H$_2$O) C, H, N.

3-[(1-Hydroxyethyl-piperazine)-1-propyl]-5,6-dihydro-2,3-dimethoxy-8,9-methylenedioxy-5,11-dioxo-11H-indeno[1,2-c]isoquinoline (5w). The desired analogue was isolated as a dark brown solid (258 mg, 47%): mp 262-264° C. $^1$H NMR (CDCl$_3$) δ 8.00 (s, 1H), 7.60 (s, 1H), 7.32 (s, 1H), 7.04 (s, 1H), 6.06 (s, 2H), 4.52 (bs, 2H), 4.03 (s, 3H), 3.96 (s, 3H), 3.22 (bs, 4H), 3.13 (bs, 6H), 2.84 (bs, 2H), 2.68 (bs, 2H), 1.73 (bs, 4H), 1.63 (bs, 4H), 1.43 (s, 18H), 1.41 (s, 9H); ESIMS m/z (rel intensity) 522 (MH$^+$, 100). Anal. (C$_{28}$H$_{31}$N$_3$O$_7$.0.8H$_2$O) C, H, N.

6-[3-Morpholylethylamino)-1-propyl]-5,6-dihydro-2,3-dimethoxy-8,9-methylenedioxy-5,11-dioxo-11H-indeno[1,2-c]isoquinoline (5x). The desired analogue was isolated as a pale purple solid (245 mg, 59%): mp 215-217° C. $^1$H NMR (CDCl$_3$) δ 8.01 (s, 1H), 7.62 (s, 1H), 7.42 (s, 1H), 7.05 (s, 1H), 6.06 (s, 2H), 4.52 (bs, 2H), 4.03 (s, 3H), 3.97 (s, 3H), 3.70 (bs, 4H), 2.81 (bs, 2H), 2.73 (bs, 2H), 2.53 (bs, 2H), 2.46 (bs, 4H), 2.02 (bs, 2H); ESIMS m/z (rel intensity) 522 (MH$^+$, 100). Anal. (C$_{28}$H$_{31}$N$_3$O$_7$.1.0H$_2$O) C, H, N.

General Procedure for the Preparation of Mono-Boc-Protected Diamines. Boc$_2$O (0.500 g, 2.291 mmol) was dissolved in CHCl$_3$ (10 mL) and the solution was added dropwise to a solution of diamine (11.45 mmol) in CHCl$_3$ (50 mL). The reaction mixture was allowed to stir at room temperature for 24 h, concentrated, and purified by flash column chromatography (SiO$_2$), eluting with a solution of 1% Et$_3$N/10% MeOH in CHCl$_3$, to provide the mono-Boc protected diamine. (Mono-Boc-1-diaminoethane, mono-Boc-1,3-diaminopropane, and mono-Boc-1,4-diaminobutane were also prepared as described below.)

Mono-Boc-1,7-diaminoheptane The general procedure provided the desired compound as a colorless semisolid (0.473 g, 90%). $^1$H NMR (CDCl$_3$) δ 4.52 (bs, 1H), 3.12 (q, J=6.2 Hz, 2H), 2.70 (t, J=6.8 Hz, 2H), 1.43-1.23 (m, 19H).

Mono-Boc-1,8-diaminooctane The general procedure provided the desired compound as a colorless semisolid (0.492 g, 88%). $^1$H NMR (CDCl$_3$) δ 4.51 (bs, 1H), 3.12 (q, J=6.5 Hz, 2H), 2.69 (t, J=6.8 Hz, 2H), 1.43-1.23 (m, 21H).

Mono-Boc-1,9-diaminononane. The general procedure provided the desired compound as a colorless semisolid (0.125 g, 21%). $^1$H NMR (CDCl$_3$) δ 4.50 (bs, 1H), 3.12 (q, J=6.5 Hz, 2H), 2.70 (t, J=6.8 Hz, 2H), 1.44-1.22 (m, 23H).

Mono-Boc-1,10-diaminodecane. The general procedure provided the desired compound as a colorless semisolid (0.192 g, 31%). $^1$H NMR (CDCl$_3$) δ $^1$H NMR (CDCl$_3$) δ 4.50 (bs, 1H), 3.13 (q, J=6.3 Hz, 2H), 2.71 (t, J=6.9 Hz, 2H), 1.44-1.18 (m, 27H).

Mono-Boc-1,11-diaminoundecane. The general procedure provided the desired compound as a colorless solid (0.555 g, 85%): mp 30-34° C. IR (film) 3370, 2919, 2851, 1687, and 1522 cm$^{-1}$; $^1$H NMR (CDCl$_3$) δ 4.49 (bs, 1H), 3.11 (q, J=6.5 Hz, 2H), 2.71 (t, J=6.8 Hz, 2H), 1.44-1.27 (m, 29H); ESIMS m/z (rel intensity) 287 (MH$^{30}$, 100). Anal. (C$_{16}$H$_{34}$N$_2$O$_2$) C, H, N.

Mono-Boc-1,12-diaminododecane. The general procedure provided the desired compound as a colorless semisolid (0.191 g, 28%). $^1$H NMR (CDCl$_3$) δ 4.48 (bs, 1H), 3.11 (q, J=6.2 Hz, 2H), 2.76 (t, J=6.9 Hz, 2H), 1.44-1.26 (m, 31H).

6-Amino-5,6-dihydro-5,11-diketo-11H-indeno[1,2-c]isoquinoline (5z). Benz[d]indeno[1,2-b]pyran-5,11-dione (4d) (0.150 g, 0.604 mmol) was treated with hydrazine (0.255 g, 7.964 mmol) in CHCl$_3$ (50 mL) and the reaction mixture was heated at reflux for 16 h. The reaction mixture was allowed to cool to room temperature, diluted with CHCl$_3$ (150 mL), and washed with sat NaHCO$_3$ (2×50 mL). The solution was dried over sodium sulfate and concentrated to provide a red-orange solid (0.120 g, 76%): mp 272-274° C. IR (film) 3448, 3305, 1686, 1663, 1610, 1507, 1312, 762 cm$^{-1}$; $^1$H NMR (CDCl$_3$) δ 8.54 (d, J=7.8 Hz, 1H), 8.51 (d, J=7.2 Hz, 1H), 8.24 (d, J=7.4 Hz, 1H), 7.85 (m, 1H), 7.60-7.45 (m, 4H), 6.19 (s, 2H); EIMS m/z (rel intensity) 262 (M$^+$, 100). Anal. (C$_{16}$H$_{10}$N$_2$O$_2$·0.25H$_2$O) C, H, N.

General Procedure for the Preparation of Mono-Boc-Protected Indenoisoquinolines. Mono-Boc protected diamine (2.054 mmol) was added to a solution of benz[d]indeno[1,2-b]pyran-5,11-dione (4d) (0.255 g, 1.027 mmol) in CHCl$_3$ (100 mL). The reaction mixture was heated at reflux for 24 h, concentrated, and purified by flash column chromatography (SiO$_2$), eluting with CHCl$_3$, to provide the mono-Boc-protected indenoisoquinoline, (Mono-boc-protected indenoisoquinolines 5aa, 5ab, and 5ac were also prepared as described below.)

6-(7'-tert-BOC-Aminoheptyl)-5,6-dihydro-5,11-dioxo-11H-indeno[1,2-c]isoquinoline (5af). The general procedure provided the desired compound as a yellow-orange solid (0.451 g, 95%): mp 112-116° C. IR (film) 3369, 1697, 1664, 1503, and 1172 cm$^{-1}$; $^1$H NMR (DMSO-d$_6$) δ 8.58 (d, J=8.1 Hz, 1H), 8.23 (d, J=8.2 Hz, 1H), 7.84-7.79 (m, 1H), 7.71 (d, J=7.7 Hz, 1H), 7.63-7.50 (m, 4H), 6.76 (m, 1H), 4.50 (t, J=7.4 Hz, 2H), 2.90 (q, J=6.2 Hz, 2H), 1.77 (m, 2H), 1.46-1.28 (m, 17H); ESIMS m/z (rel intensity) 483 (MNa$^+$, 100). Anal. (C$_{28}$H$_{32}$N$_2$O$_4$) C, H, N.

6-(8'-tert-BOC-Aminooctyl)-5,6-dihydro-5,11-dioxo-11H-indeno[1,2-c]isoquinoline (5ag). The general procedure provided the desired compound as a yellow-orange solid (0.466 g, 97%); mp 140-143° C. IR (film) 3368, 2929, 1698, 1665, 1504, and 1172 cm$^{-1}$; $^1$H NMR (DMSO-d$_6$) δ 8.58 (d, J=7.9 Hz, 1H), 8.23 (d, J=8.1 Hz, 1H), 7.84-7.78 (m, 1H), 7.71 (d, J=7.5 Hz, 1H), 7.63-7.47 (m, 4H), 6.75 (m, 1H), 4.50 (t, J=7.4 Hz, 2H), 2.91 (q, J=6.6 Hz, 2H), 1.78 (m, 2H), 1.46-1.26 (m, 19H); ESIMS m/z (rel intensity) 497 (MNa$^+$, 100). Anal. (C$_{29}$H$_{34}$N$_2$O$_4$) C, H, N.

6-(9'-tert-BOC-Aminononyl)-5,6-dihydro-5,11-dioxo-11H-indeno[1,2-c]isoquinoline (5ah). The general procedure provided the desired compound as an orange solid (0.145 g, 77%): mp 91-95° C. IR (film) 3371, 2928, 1698, 1666, 1504, and 1172 cm$^{-1}$; $^1$H NMR (DMSO-d$_6$) δ 8.58 (d, J=8.0 Hz, 1H), 8.23 (d, J=7.4 Hz, 1H), 7.84-7.79 (m, 1H), 7.71 (d, J=7.4 Hz, 1H), 7.63-7.50 (m, 4H), 6.74 (m, 1H), 4.50 (t, J=7.3 Hz, 2H), 2.91 (q, J=6.6 Hz, 2H), 1.78 (m, 2H), 1.47-1.24 (m, 21H); ESIMS m/z (rel intensity) 511 (MNa$^+$, 100). Anal. (C$_{30}$H$_{36}$N$_2$O$_4$) C, H, N.

6-(10'-tert-BOC-Aminodecyl)-5,6-dihydro-5,11-dioxo-11H-indeno[1,2-c]isoquinoline (5ai). The general procedure provided the desired compound as a yellow-orange solid (0.220 g, 78%): mp 135-137° C. IR (film) 3368, 2927, 1698, 1666, 1504, and 1172 cm$^{-1}$; $^1$H NMR (DMSO-d$_6$) δ 8.58 (d, J=7.9 Hz, 1H), 8.23 (dd, J=8.1 Hz and 0.7 Hz, 1H), 7.84 (dt, J=7.2 Hz and 1.4 Hz, 1H), 7.71 (d, J=7.5 Hz, 1H), 7.63-747 (m, 4H), 6.76 (m, 1H), 4.50 (t, J=7.4 Hz, 2H), 2.90 (q, J=6.5 Hz, 2H), 1.77 (m, 2H), 1.46-1.23 (m, 23H); ESIMS m/z (rel intensity) 525 (MNa$^+$, 100). Anal. (C$_{31}$H$_{38}$N$_2$O$_4$) C, H, N.

6-(11'-tert-BOC-Aminoundecyl)-5,6-dihydro-5,11-dioxo-11H-indeno[1,2-c]isoquinoline (5aj). The general procedure provided the desired compound as a yellow-orange solid (0.445 g, 86%): mp 111-114° C. IR (KBr) 3364, 2918, 2850, 1678, 1660, 1534, 1505, and 758 cm$^{-1}$; $^1$H NMR (DMSO-d$_6$) δ 8.58 (d, J=8.1 Hz, 1H), 8.23 (d, J=7.4 Hz, 1H), 7.84-7.79 (m, 1H), 7.71 (d, J=7.5 Hz, 1H), 7.62-7.50 (m, 4H), 6.74 (m, 1H), 4.50 (t, J=7.4 Hz, 2H), 2.90 (q, J=6.5 Hz, 2H), 1.78 (m, 2H), 1.46-1.22 (m, 25H); ESIMS m/z (rel intensity) 539 (MNa$^+$, 100). Anal. (C$_{32}$H$_{40}$N$_2$O$_4$) C, H, N.

6-(12'-tert-BOC-Aminododecyl)-5,6-dihydro-5,11-dioxo-11H-indeno[1,2-c]isoquinoline (5ak). The general procedure provided the desired compound as a yellow-orange solid (0.177 g, 66%): mp 129-134° C. IR (film) 3369, 2926, 1698, 1666, 1504, and 1172 cm$^{-1}$; $^1$H NMR (DMSO-d$_6$) δ 8.58 (d, J=8.0 Hz, 1H), 8.22 (d, J=7.4 Hz, 1H), 7.84-7.78 (m, 1H), 7.71 (d, J=7.5 Hz, 1H), 7.62-7.50 (m, 4H), 6.74 (m, 1H), 4.50 (t, J=7.3 Hz, 2H), 2.90 (q, J=6.6 Hz, 2H), 1.77 (m, 2H), 1.46-1.22 (m, 27H); ESIMS m/z (rel intensity) 553 (MNa$^+$, 100). Anal. (C$_{33}$H$_{42}$N$_2$O$_4$) C, H, N.

6-(5-Aminopentyl)-5,6-dihydro-5,11-diketo-11H-indeno[1,2-c]isoquinoline Hydrochloride (5ao). Benz[d]indeno[1,2-b]pyran-5,11-dione (4d) (0.100 g, 0.403 mmol) was treated with 1,5-diaminopentane (0.206 g, 2.014 mmol) in CHCl$_3$ (40 mL) and the reaction mixture was heated at reflux for 16 h. The reaction mixture was allowed to cool to room temperature and washed with water (3×15 mL). The solution was dried over sodium sulfate, filtered, and treated with 2 M HCl in Et$_2$O (5 mL). After 30 film, the reaction mixture was filtered and the filter pad was washed with CHCl$_3$ (50 mL) and hexanes (50 mL) to provide an orange solid (0.122 g, 82%): mp 265-268° C. IR (film) 3432, 3077, 2856, 1707, 1635, 1611, 1549, and 1504 cm$^{-1}$; $^1$H NMR (CDCl$_3$) δ 8.59 (d, J=8.1 Hz, 1H), 8.23 (d, J=8.1 Hz, 1H), 7.85-7.80 (m, 3H), 7.74 (d, J=7.4 Hz, 1H), 7.63-7.51 (m, 4H), 4.52 (t, J=7.3 Hz, 2H), 2.81 (m, 2H), 1.83 (m, 2H) 1.65-1.52 (m, 4H); ESIMS m/z (rel intensity) 333 (MH$^+$, 100). Anal. ($C_{21}H_{21}ClN_2O_2 \cdot 0.75H_2O$) C, H, N.

6-(6-Aminohexyl)-5,6-dihydro-5,11-diketo-11H-indeno[1,2-c]isoquinoline Hydrochloride (5ap). Benz[d]indeno[1,2-b]pyran-5,11-dione (4d) (0.100 g, 0.403 mmol) was treated with 1,6-diaminohexane (0.234 g, 2.014 mmol) in CHCl$_3$ (40 mL) and the reaction mixture was heated at reflux for 16 h. The reaction mixture was allowed to cool to room temperature and washed with water (3×25 mL). The solution was dried over sodium sulfate, filtered, and treated with 2 M in Et$_2$O (5 mL). After 30 min, the reaction mixture was filtered and the filter pad was washed with CHCl$_3$ (50 mL) and hexanes (50 mL) to provide an orange solid (0.125 g, 81%): mp 195° C. (dec). IR (film) 3435, 1660, 1630, 1610, and 1504 cm$^{-1}$; $^1$H NMR (CDCl$_3$) δ 8.59 (d, J=7.8 Hz, 1H), 8.23 (d, J=8.1 Hz, 1H), 7.85-7.71 (m, 4H), 7.61-7.51 (m, 4H), 4.52 (t, J=7.3 Hz, 2H), 2.78 (m, 2H), 1.79 (m, 2H), 1.59-1.39 (m, 6H); ESIMS m/z (rel intensity) 347 (MH$^+$, 100). Anal. ($C_{22}H_{23}ClN_2O_2 \cdot 0.5H_2O$) C, H, N.

General Procedure for the Preparation of indenoisoquinoline Hydrochloride Salts. 3 M HCl in MeOH (10 mL) was slowly added to a solution of mono-Boc protected indenoisoquinoline (0.100 g, 0.188-0.217 mmol) in CHCl$_3$ (50 mL) at room temperature. After 2 h, the reaction mixture was concentrated and the residue was triturated with Et$_2$O. Filtration of the obtained solid provided the indenoisoquinoline as a hydrochloride salt. (Indenoisoquinoline hydrochloride salts 5al, 5am, and 5an were also prepared as described below.)

6-(7-Aminoheptyl)-5,6-dihydro-5,11-dioxo-11H-indeno[1,2-c]isoquinoline Hydrochloride (5aq). The general procedure provided the desired compound as a yellow-orange solid (0.085 g, 99%): mp 228-231° C. IR (KBr) 3436, 2931, 1702, 1650, 1611, 1549, 1504, and 759 cm$^{-1}$; $^1$H NMR (DMSO-d$_6$) δ 8.60 (d, J=8.1 Hz, 1H), 8.24 (d, J=8.2 Hz, 1H), 7.85-7.80 (m, 1H), 7.73 (d, J=7.4 Hz, 1H), 7.63-7.49 (m, 6H), 4.53 (t, J=7.0 Hz, 2H), 2.78 (t, J=7.1 Hz, 2H), 1.80 (m, 2H), 1.55-1.35 (m, 8H); ESIMS m/z (rel intensity) 361 (MH$^+$, 100). Anal. ($C_{23}H_{25}ClN_2O_2 \cdot 0.5H_2O$) C, H, N.

6-(8-Aminooctyl)-5,6-dihydro-5,11-dioxo-11H-indeno[1,2-c]isoquinoline Hydrochloride (5ar). The general procedure provided the desired compound as an orange solid (0.083 g, 95%): mp 182-185° C. IR (KBr) 3436, 2930, 1661, 1505, and 761 cm$^{-1}$; $^1$H NMR (DMSO-d$_6$) δ 8.60 (d, J=8.5 Hz, 1H), 8.24 (d, J=7.0 Hz, 1H), 7.86-7.81 (m, 1H), 7.73 (d, J=7.6 Hz, 1H), 7.63-7.52 (m, 6H), 4.52 (t, J=7.9 Hz, 2H), 2.78 (t, J=7.3 Hz, 2H), 1.79 (m, 2H), 1.50 (m, 4H), 1.31 (m, 6H); ESIMS m/z (rel intensity) 375 (MH$^+$, 100). Anal. ($C_{24}H_{27}ClN_2O_2 \cdot 0.75H_2O$) C, H, N.

6-(9-Aminononyl)-5,6-dihydro-5,11-dioxo-11H-indeno[1,2-c]isoquinoline Hydrochloride (5as). The general procedure provided the desired compound as an orange solid (0.082 g, 94%): mp 204-207° C. (KBr) 3435, 2927, 1702, 1662, 1610, 1549, 1504, 1427, and 759 cm$^{-1}$; $^1$H NMR (DMSO-d$_6$) δ 8.60 (d, J=8.3 Hz, 1H), 8.24 (d, J=9.3 Hz, 1H), 7.83-7.81 (m, 1H), 7.73 (d, J=7.8 Hz, 1H), 7.63-7.51 (m, 6H), 4.52 (t, J=8.3 Hz, 2H), 2.78 (t, J=7.3 Hz, 2H), 1.79 (m, 2H), 1.51 (m, 4H), 1.28 (m, 8H); ESIMS m/z (rel intensity) 389 (MH$^+$, 100). Anal. ($C_{25}H_{29}ClN_2O_2 \cdot 0.75H_2O$) C, H, N.

6-(10-Aminodecyl)-5,6-dihydro-5,11-dioxo-11H-indeno[1,2-c]isoquinoline Hydrochloride (5at). The general procedure provided the desired compound as an orange solid (0.087 g, 91%): mp 189-192° C. IR (KBr) 3443, 2925, 2851, 1705, 1646, 1611, 1550, 1504, 1467, and 759 cm$^{-1}$; $^1$H NMR (DMSO-d$_6$) δ 8.60 (d, J=7.9 Hz, 1H), 8.23 (d, J=7.5 Hz, 1H), 7.83 (m, 1H), 7.73 (d, J=8.0 Hz, 1H), 7.63-7.51 (m, 6H), 4.52 (t, J=7.4 Hz, 2H), 2.76 (m, 2H), 1.79 (m, 2H), 1.49 (m, 4H), 1.27 (m, 10H); ESIMS m/z (rel intensity) 403 (MH$^+$, 100). Anal. ($C_{26}H_{31}ClN_2O_2 \cdot 0.5H_2O$) C, H, N.

6-(11-Aminoundecyl)-5,6-dihydro-5,11-dioxo-11H-indeno[1,2-c]isoquinoline Hydrochloride (5au). The general procedure provided the desired compound as an orange solid (0.085 g, 88%): mp 125-129° C. IR (KBr) 3436, 2922, 2851, 1662, 1610, 1549, 1504, 1426, and 758 cm$^{-1}$; $^1$H NMR (DMSO-d$_6$) δ 8.60 (d, J=8.0 Hz, 1H), 8.23 (d, J=7.5 Hz, 1H), 7.85 (m, 1H), 7.72 (d, J=7.5 Hz, 1H), 7.63-7.51 (m, 6H), 4.51 (t, J=8.0 Hz, 2H), 2.77 (t, J=7.6 Hz, 2H), 1.78 (m, 2H), 1.48 (m, 4H), 1.25 (m, 12H); ESIMS m/z (rel intensity) 417 (MH$^+$, 100). Anal. ($C_{26}H_{31}ClN_2O_2 \cdot 1H_2O$) C, H, N.

6-(12-Aminododecyl)-5,6-dihydro-5,11-dioxo-11H-indeno[1,2-c]isoquinoline Hydrochloride (5ay). The general procedure provided the desired compound as a yellow solid (0.087 g, 91%): mp 175-178° C. IR (KBr) 3435, 2927, 2850, 1704, 1644, 1506, 1466, and 762 cm$^{-1}$; $^1$H NMR (DMSO-d$_6$) δ 8.59 (d, J=7.8 Hz, 1H), 8.23 (d, J=7.5 Hz, 1H), 7.83 (m, 1H), 7.72 (d, J=7.8 Hz, 1H), 7.63-7.51 (m, 6H), 4.51 (t, J=7.5 Hz, 2H), 2.76 (m, 2H), 1.78 (m, 2H), 1.51 (m, 4H), 1.24 (m, 14H); ESIMS m/z (rel intensity) 431 (MH$^+$, 100). Anal. ($C_{28}H_{35}ClN_2O_2 \cdot 1.25H_2O$) C, H, N.

5,6-Dihydro-5,11-dioxo-6-(2-pyridylmethyl)-11H-indeno[1,2-c]isoquinoline (5aw). 2-(Aminomethyl)pyridine (0.054 g, 0.504 mmol) was added to a solution of benz[d]indeno[1,2-b]pyran-5,11-dione (4d) (0.100 g, 0.403 mmol) in CHCl$_3$ (50 mL) and the reaction mixture was heated at reflux for 16 h. The reaction mixture was allowed to cool to room temperature, washed with H$_2$O (3×25 mL), sat NaCl (25 mL), dried over sodium sulfate, and concentrated. The residue was washed with EtOAc, hexanes, and dried to provide a yellow solid (0.110 g, 81%): mp 240-242° C. IR (KBr) 1698, 1655, 1618, 1501, 1427, and 755 cm$^{-1}$; $^1$H NMR (DMSO-d$_6$) δ 8.62 (d, J=8.0 Hz, 1H), 8.56 (d, J=4.9 Hz, 1H), 8.22 (d, J=8.1 Hz, 1H), 7.97 (dt, J=7.8 Hz and 1.7 Hz, 1H), 7.89 (m, 1H), 7.61-7.37 (m, 7H), 5.91 (s, 2H); ESIMS m/z (rel intensity) 339 (MH$^+$, 100). Anal. ($C_{22}H_{14}N_2O_2$) C, H, N.

5,6-Dihydro-5,11-dioxo-6-(3-pyridylmethyl)-11H-indeno[1,2-c]isoquinoline Hydrochloride (5ax). 3-(Aminomethyl)pyridine (0.054 g, 0.504 mmol) was added to a solution of benz[d]indeno[1,2-b]pyran-5,11-dione (4d) (0.100 g, 0.403 mmol) in CHCl$_3$ (50 mL) and the reaction mixture was heated at reflux for 16 h. The reaction mixture was allowed to cool to room temperature, washed with H$_2$O (3×25 mL), sat NaCl (25 mL), dried over sodium sulfate, and concentrated. The residue was diluted with CHCl$_3$ (40 mL), 3 M HCl in MeOH (10 mL) was added, and the reaction mixture was allowed to stir at room temperature for 2 h. The reaction mixture was concentrated, and the residue was washed with CHCl$_3$ to provide a pink solid (0.146 g, 97%): mp 274° C.; (dec). IR (KBr) 2343, 2106, 1695, 1655, 1610, 1551, 1501, and 754 cm$^{-1}$; $^1$H NMR (DMSO-d$_6$) δ 8.98 (s, 1H), 8.78 (d, J=5.2 Hz, 1H), 8.64 (d, J=8.1 Hz, 1H), 8.36 (d, J=9.1 Hz, 1H), 8.23 (d, J=7.5 Hz, 1H), 7.90 (m, 2H), 7.59-7.39 (m, 5H), 5.89 (s, 2H); ESIMS m/z (rel intensity) 339 (MH$^+$, 100). Anal. ($C_{22}H_{15}ClN_2O_2$) C, H, N.

5,6-Dihydro-5,11-dioxo-6-(2-pyridylethyl)-11H-indeno[1,2-c]isoquinoline Hydrochloride (5ay). 2-(2-Aminoethyl)pyridine (0.098 g, 0806 mmol) was added to a solution of benz[d]indeno[1,2-b]pyran-5,11-dione (4d) (0.100 g, 0.403 mmol) in CHCl$_3$ (50 mL) and the reaction mixture was heated at reflux for 16 h. The reaction mixture was allowed to cool to room temperature, washed with H$_2$O (3×25 mL), sat NaCl (25 mL), dried over sodium sulfate, and concentrated. The residue was diluted with CHCl$_3$ (40 mL), 3 M HCl MeOH (10 mL) was added, and the reaction mixture was allowed to stir at room temperature for 2 h. The reaction mixture was concentrated, and the residue was washed with CHCl$_3$ to provide a yellow solid (0.146 g, 93%): mp 240° C. (dec). IR (KBr) 2307, 1698, 1659, 1610, 1548, 1504, 1429, and 760 cm$^{-1}$; $^1$H NMR (DMSO-d$_6$) δ 8.78 (d, J=5.5 Hz, 1H), 8.57 (d, J=8.0 Hz, 1H), 8.33 (m, 1H), 8.02 (d, J=8.0 Hz, 1H), 7.97 (d, J=8.0 Hz, 1H), 7.90 (d, J=8.0 Hz, 1H), 7.80 (m, 2H), 7.61-7.44 (m, 4H), 4.92 (t, J=6.5 Hz, 2H), 3.59 (t, J=6.3 Hz, 2H); ESIMS m/z (rel intensity) 353 (MH$^+$, 100). Anal. (C$_{23}$H$_{17}$ClN$_2$O$_2$) C, H, N.

5,6-Dihydro-5,11-dioxo-6-(3-pyridylethyl)-11H-indeno[1,2-c]isoquinoline (5az). 3-(2-Aminoethyl)pyridine (0.172 g, 0.604 mmol) was added to a solution of benz[d]indeno[1,2-b]pyran-5,11-dione (4d) (0.100 g, 0.403 mmol) in CHCl$_3$ (50 mL). Triethylamine (0.224 mL, 1.612 mmol) was added and the reaction mixture was heated at reflux for 16 h. The reaction mixture was allowed to cool to room temperature, washed with H$_2$O (3×25 mL), sat NaCl (25 mL), dried over sodium sulfate, and concentrated. The obtained precipitate was washed with EtOAc, hexanes, and dried to provide an orange solid (0.140 g, 99%): mp 220° C. (dec), IR (KBr) 1691, 1660, 1609, 1549, 1504, 1424, and 765 cm$^{-1}$; $^1$H NMR (DMSO-d$_6$) δ 8.90 (s, 1H), 8.73 (d, J=5.6 Hz, 1H), 8.59 (d, J=8.1 Hz, 1H), 8.44 (d, J=7.9 Hz, 1H), 8.10 (d, J=8.1 Hz, 1H), 7.88 (m, 3H), 7.61-7.48 (m, 4H), 4.87 (t, J=6.7 Hz, 2H), 3.37 (t, J=6.3 Hz, 2H); ESIMS m/z (rel intensity) 353 (MH$^+$, 100). Anal. (C$_{23}$H$_{16}$N$_2$O$_2$·0.55H$_2$O) C, H, N.

cis-4-Carboxy-N-(3-chloropropyl)-3,4-dihydro-3-(4-methoxyphenyl)-1(2H)isoquinolone (8a). Homophthalic anhydride (6a) (3.065 g, 18.90 mmol) was added to a chloroform (125 mL) solution of 4-methoxybenzylidene-(3-chloro-1-propylamine) (7a) (4.000 g, 18.90 mmol) and the reaction mixture was allowed to stir at room temperature for 3 h. The obtained precipitate was filtered, washed with chloroform (100 mL), and dried to provide an off-white solid (4.723 g, 67%): mp 180-181° C. IR (KBr) 3437, 2957, 1740, 1622, 1598, 1573, 1514, 1479, 1258, and 1173 cm$^{-1}$; $^1$H NMR (CD$_3$OD) δ 8.10 (dd, J=7.6 Hz and 1.4 Hz, 1H), 7.63 (d, J=7.6 Hz, 1H), 7.55 (dt, J=7.4 Hz and 1.5 Hz, 1H), 7.50 (m, 1H), 6.97 (m, 2H), 6.75 (m, 2H), 5.13 (d, J=6.3 Hz, 1H), 4.76 (d, J=6.2 Hz, 1H), 3.98 (m, 1H), 3.70 (s, 3H), 3.61 (m, 2H), 3.22 (m, 1H), 2.13-2.01 (m, 2H); ESIMS m/z (rel intensity) 374/376 (MH$^+$, 100/33). Anal. (C$_{20}$H$_{20}$ClNO$_4$) C, H, N.

Benzylidene-(3-bromo-1-propylamine) (7b). The hydrobromide salt of 3-bromopropylamine (5.364 g, 24.50 mmol) was treated with triethylamine (4 mL) in CHCl$_3$ (100 mL) and allowed to stir at room temperature for 5 min. Benzaldehyde (2.000 g, 18.85 mmol) and magnesium sulfate (6.000 g) were added and the reaction mixture was allowed to stir at room temperature for 16 h. The reaction mixture was filtered and the filter pad was washed with CHCl$_3$ (50 mL). The filtrate was washed with water (3×50 mL), sat NaCl (50 mL), dried over sodium sulfate, and concentrated to provide a yellow oil (4.262 g, 100%). IR (film) 1645, 754, and 693 cm$^{-1}$; $^1$H NMR (CDCl$_3$) δ 8.34 (s, 1H), 7.76 (m, 2H), 7.44 (m, 3H), 3.78 (dt, J=6.3 Hz and 1.3 Hz, 2H), 3.52 (t, J=6.5 Hz, 2H), 2.31 (pent, J=6.4 Hz, 2H); ESIMS m/z (rel intensity) 226/228 (MH$^+$, 100/91). Anal. (C$_{10}$H$_{12}$BrN) C, H, N.

cis-4-Carboxy-3,4-dihydro-N-(3-bromopropyl)-3-phenyl-7-nitro-1(2H)isoquinolone (8b). 4-Nitrohomophthalic anhydride (6b) (3.664 g, 17.69 mmol) was added to a chloroform (125 mL) solution of benzylidene-(3-bromo-1-propylamine) (7b) (4.000 g, 17.69 mmol), and the reaction mixture was allowed to stir at room temperature for 1.25 h. The obtained precipitate was filtered, washed with chloroform (150 mL), and dried to provide a yellow solid (6.278 g, 82%): mp 158-160° C. IR (KBr) 3435, 3061, 1743, 1638, 1520, 1349, and 1191 cm$^{-1}$; $^1$H NMR (CD$_3$OD) δ 8.90 (d, J=2.5 Hz, 1H), 8.38 (dd, J=8.7 Hz and 2.6 Hz, 1H), 7.98 (m, 1H), 7.25-7.19 (m, 3H), 7.07-7.03 (m, 2H), 5.32 (d, J=6.2 Hz, 1H), 4.96 (d, J=6.2 Hz, 1H), 3.99 (m, 1H), 3.52 (m, 2H), 3.26 (m, 1H), 2.26-2.12 (m, 2H); negative ion ESIMS m/z (rel intensity) 431/433 [(M-H$^+$)$^-$, 12/9]. Anal. (C$_{19}$H$_{17}$BrN$_2$O$_5$·1.0H$_2$O) C, H, N.

6-(3-Chloropropyl)-5,6-dihydro-9-methoxy-5,11-dioxo-1H-indeno[1,2-c]isoquinoline (5bc). Thionyl chloride (2 mL) was added to a solution of cis-4-carboxy-N-(3-chloropropyl)-3,4-dihydro-3-(4-methoxyphenyl)-1(2H)isoquinolone (8a) (0.510 g, 1.364 mmol) in benzene (40 mL). The reaction mixture was heated at reflux for 30 min, allowed to cool to room temperature, and concentrated. The residue was diluted with nitrobenzene (20 mL), chilled in an ice bath, and aluminum chloride (0.364 g, 2.728 mmol) was added. The reaction mixture was removed from the bath and heated at 100° C. for 1.5 h. Ice water (100 mL) was added and the solution was extracted with CHCl$_3$ (3×50 mL). The combined organic layer was washed with sat NaHCO$_3$ (3×50 mL), sat NaCl (50 mL), and dried over sodium sulfate. The solution was concentrated, hexanes (250 mL) were added, and liquid was decanted. The obtained solid was washed with hexanes (100 mL) and the liquid was again decanted. The solid was purified by flash column chromatography (SiO$_2$), eluting with chloroform, to provide a purple-red solid (0.082 g, 17%) that was precipitated from EtOAc/hexanes: mp 195-198° C. IR (KBr) 1662, 1611, 1505, 1481, 1432, and 1299 cm$^{-1}$; $^1$H NMR (CDCl$_3$) δ 8.67 (d, J=8.1 Hz, 1H), 8.31 (dd, J=8.2 Hz and 0.7 Hz, 1H), 7.73 (m, 1H), 7.66 (d, J=8.4 Hz, 1H), 7.45 (m, 1H), 7.22 (d, J=2.6 Hz, 1H), 6.86 (dd, J=8.4 Hz and 2.6 Hz, 1H), 4.67 (m, 2H), 3.89 (s, 3H), 3.83 (m, 2H), 2.43 (m, 2H); CIMS m/z (rel intensity) 354/356 (MH$^+$, 100/30). Anal. (C$_{20}$H$_{16}$ClNO$_3$) C, H, N.

6-(3-Bromopropyl)-5,6-dihydro-5,11-dioxo-3-nitro-11H-indeno[1,2-c]isoquinoline (5bb). Thionyl chloride (5 mL) was added to a solution of cis-4-carboxy-3,4-dihydro-N-(3-bromopropyl)-3-phenyl-7-nitro-1(2H)isoquinolone (8b) (1.000 g, 2.308 mmol) in benzene (50 mL). The reaction mixture was heated at reflux for 30 min, allowed to cool to room temperature, and concentrated. The residue was diluted with nitrobenzene (30 mL), chilled in an ice bath, and aluminum chloride (0.616 g, 4.616 mmol) was added. The reaction mixture was removed from the bath and heated at 100° C., for 1 h. Ice water (100 mL) was added and the solution was extracted with CHCl$_3$ (3×100 mL). The combined organic layer was washed with sat NaHCO$_3$ (3×50 mL), sat NaCl (50 mL) and dried over sodium sulfate. The solution was concentrated, hexanes (900 mL) were added, and liquid was decanted. The obtained solid was washed with hexanes (100 mL) and the liquid was again decanted. The crude solid was purified by flash column chromatography (SiO$_2$), eluting with chloroform, to provide an orange solid (0.432 g, 45%): mp 258-260° C. (dec). IR (film) 1672, 1612, 1560, 1503, 1428, and 1337 cm$^{-1}$; $^1$H NMR (CDCl$_3$) δ 9.20 (d, J=2.4 Hz, 1H), 8.89 (d, J=8.9 Hz, 1H), 8.52 (dd, J=9.0 Hz and 2.4 Hz, 1H), 7.92 (m, 1H), 7.75 (m, 1H), 7.57-7.52 (m, 2H), 4.76 (m, 2H), 3.70 (t, J=6.2 Hz, 2H), 2.54 (m, 2H); CIMS m/z (rel intensity) 413/415 (MH$^+$, 100/82). Anal. (C$_{19}$H$_{13}$BrN$_2$O$_4$) C, H, N.

Bis{(5,6-dihydro-5,11-diketo-11H-indeno[1,2-c]isoquinoline)-6-ethyl}amine (12a). 2,2'-Diaminodiethylamine (11a) (0.3 g, 2.91 mmol) was added to a stirred solution of indenobenzopyran 4d (2.17 g, 8.72 mmol) in CHCl$_3$ (200 mL) and the mixture was stirred under reflux for 48 h. The reaction mixture was then cooled and the resultant orange solid was filtered through a sintered glass funnel and washed with chloroform (30 mL) to provide pure bisindenoisoquinoline 12a (0.75 g, 46%) as an orange solid: mp 240-242° C. $^1$H NMR (DMSO-d$_6$) δ 8.51 (d, J=8.9 Hz, 2H), 8.11 (d, J=7.7 Hz, 2H), 7.76 (bs, 4H), 7.47 (bs, 4H), 7.36 (bs, 4H), 4.51 (bs, 4H), 3.03 (bs, 4H); ESIMS m/z (rel intensity) (MH$^+$, 100). Anal. Calcd for C$_{36}$H$_{25}$N$_3$O$_4$: C, 76.72; H, 4.47; N, 7.46. Found: C, 76.35; H, 4.45; N, 7.39.

Bis{(5,6-dihydro-5,11-diketo-11H-indeno[1,2-c]isoquinoline)}-(6-ethyl,6'-propyl)amine (12b). 2-Aminoethyl-3-aminopropylamine (11b) (0.2 g, 1.71 mmol) was added to a stirred solution of indenobenzopyran 4d (1.06 g, 4.27 mmol) in CHCl$_3$ (200 mL) and the reaction mixture was stirred under reflux for 48 h. The reaction mixture was then cooled and the resultant orange solid was filtered through a sintered glass funnel and washed with chloroform-methanol mixture (2:8, 50 mL) to provide pure bisindenoisoquinoline 12b (0.72 g, 73%) as an orange solid: mp 250-252° C. $^1$H NMR (CDCl$_3$) δ 8.69 (d, J=8.5 Hz, 2H), 8.29 (t, J=7.4 Hz, 2H), 7.70 (t, J=7.4 Hz, 2H), 7.62 (m, 2H), 7.46-7.37 (m, 8H), 4.69 (t, J=7.3 Hz, 2H), 4.61 (t, J=7.5 Hz, 2H), 3.16 (t, J=7.3 Hz, 2H), 2.89 (t, J=6.0 Hz, 2H), 2.05 (m, 2H); ESIMS m/z (rel intensity) 578 (MH$^+$, 100); HRESIMS calcd for (C$_{37}$H$_{27}$N$_3$O$_4$)H$^+$: 578.2079. Found: 578.2087.

Bis{(5,6-dihydro-5,11-diketo-1H-indeno[1,2-c]isoquinoline)-6-propyl}amine (12c). 3,3'-Diaminodipropylamine (11c) (0.3 g, 2.29 mmol) was added to a stirred solution of indenobenzopyran 4d (1.7 g, 6.86 mmol) in CHCl$_3$ (200 mL) and the mixture was stirred under reflux for 48 h. The bright orange reaction mixture was purified by flash column chromatography (SiO$_2$/CHCl$_3$ to 3% MeOH in CHCl$_3$) to afford pure bisindenoisoquinoline 12c (0.54 g) in 40% yield as a dark orange solid: mp 223-225° C. $^1$H NMR (CDCl$_3$) δ 8.65 (d, J=8.1 Hz, 2H), 8.27 (d, J=8.1 Hz, 2H), 7.67 (t, J=7.1 Hz, 4H), 7.57 (d, J=7.0 Hz, 2H), 7.41 (t, J=7.1 Hz, 4H), 7.33 (t, J=7.1 Hz, 2H), 4.62 (t, J=7.3 Hz, 4H), 2.84 (t, J=6.4 Hz, 4H), 2.08 (m, 4H); $^1$H NMR (DMSO-d$_6$) δ 8.53 (d, J=7.8 Hz, 2H), 8.18 (d, J=7.9 Hz, 2H), 7.87 (d, J=7.4 Hz, 2H), 7.79 (t, J=7.6 Hz, 2H), 7.54 (t, J=5.8 Hz, 4H), 7.46 (m, 4H), 4.53 (t, J=6.9 Hz, 4H), 2.80 (bs, 4H), 1.99 (m, 4H); ESIMS m/z (rel intensity) 592 (MH$^+$, 100). Anal. Calcd for C$_{38}$H$_{29}$N$_3$O$_4$·1.6H$_2$O: C, 73.56; H, 5.23; N, 6.77. Found: C, 73.18; H, 4.93; N, 6.47.

Bis{(5,6-dihydro-5,11-diketo-11H-indeno[1,2-c]isoquinoline)-6-propyl}methylamine (12d). 3,3'-Diamino-N-methyl dipropylamine (11d) (0.10 g, 0.69 mmol) was added to a stirred solution of indenobenzopyran 4d (0.38 g, 1.52 mmol) in CHCl$_3$ (150 mL) and the reaction mixture was stirred under reflux for 48 h. The reaction mixture was cooled to room temperature and purified by flash column chromatography (SiO$_2$/CHCl$_3$ to 5% MeOH in CHCl$_3$) to provide bisindenoisoquinoline 12d (340 mg, 82%) as a red solid: mp 230-232° C. $^1$H NMR (CDCl$_3$) δ 8.67 (d, J=8.1 Hz, 2H), 8.30 (d, J=7.6 Hz, 2H), 7.72-7.66 (dt, J=8.3 and 2.8 Hz, 4H), 7.59 (d, J=7.1 Hz, 2H), 7.48-7.40 (q, J=7.5 Hz, 4H), 7.33 (t, J=7.3 Hz, 2H), 4.63 (t, J=8.0 Hz, 4H), 2.66 (t, J=6.5 Hz, 4H), 2.37 (s, 3H), 2.13-2.04 (m, 4H); ESIMS m/z (rel intensity) 606 (MH$^+$, 100). Anal. Calcd for C$_{39}$H$_{31}$N$_3$O$_4$·0.4CHCl$_3$: C, 72.42; H, 4.84; N, 6.43. Found: C, 72.67; H, 5.05; N, 6.32.

Bis{(5,6-dihydro-5,11-diketo-11H-indeno[1,2-c]isoquinoline)}-(6-propyl,6'-butyl)amine (12e). 4-Aminobutyl-3-aminopropylamine (11e) (0.2 g, 1.38 mmol) was added to a stirred solution of indenobenzopyran 4d (0.75 g, 3.03 mmol) in CHCl$_2$ (200 mL) and the reaction mixture was stirred under reflux for 48 h. The reaction mixture was then cooled and the resultant orange solid was filtered through a sintered glass funnel and washed with chloroform-methanol mixture (5:1, 50 mL) to provide pure bisindenoisoquinoline 12e (0.63 g, 76%) as an orange solid: mp 228-230° C. $^1$H NMR (CDCl$_3$) δ 8.67 (d, J=8.1 Hz, 2H), 8.28 (d, J=8.1 Hz, 2H), 7.70-7.65 (m, 2H), 7.59 (d, J=6.8 Hz, 2H), 7.52 (d, J=7.4 Hz, 2H), 7.45-7.24 (m, 6H), 4.61 (t, J=7.3 Hz, 2H), 4.55 (t, J=7.9 Hz, 2H), 2.84 (t, J=6.5 Hz, 2H), 2.80 (t, J=6.8 Hz, 2H), 2.15-2.10 (m, 2H), 2.00-1.95 (m, 2H), 1.84-1.77 (m, 2H); ESIMS m/z (rel intensity) 606 (MH$^+$, 100); HRESIMS calcd for (C$_{39}$H$_{31}$N$_3$O$_4$)H$^+$: 606.2393. Found: 606.2402.

Bis-1,3-{(5,6-dihydro-5,11-diketo-11H-indeno[1,2-c]isoquinoline)-(6-ethyl-tert-BOCamino)}propane (13a). N,N'-Bis(2-aminoethyl)-1,3-propanediamine (11g) (0.10 g, 0.62 mmol) was added to a stirred solution of indenobenzopyran 4d (0.34 g, 1.37 mmol) in CHCl$_3$ (150 mL) and the reaction mixture was stirred under reflux for 72 h, providing bisindenoisoquinoline 12 g as a crude intermediate. After allowing the reaction mixture to cool to room temperature, Et$_3$N (0.35 mL, 2.50 mmol) and Boc$_2$O (0.34 g, 1.56 mmol) were added, and the reaction mixture was stirred at room temperature for 8 h. The crude reaction mixture was purified by flash column chromatography (SiO$_2$/20% EtOAc in hexane, then 1-5% MeOH in CHCl$_3$) to provide Boc-protected bisindenoisoquinoline 13a (380 mg, 74%) as an orange solid: mp 238-240° C. $^1$H NMR (CDCl$_3$) δ 8.63 (d, J=8.0 Hz, 2H), 8.16 (d, J=7.4 Hz, 2H), 7.65-7.58 (m, 5H), 7.53-7.45 (m, 2H), 7.38-7.29 (m, 5H), 4.63 (bs, 4H), 3.62 (bs, 4H), 3.32 (bs, 4H), 1.90 (bs, 2H), 1.41 (s, 18H); ESIMS m/z (rel intensity) 821 (MH$^+$, 10), 721 (MH$^+$-Boc, 100). Anal. Calcd for C$_{49}$H$_{48}$N$_4$O$_8$: C, 71.69; H, 5.89; N, 6.82. Found: C, 71.35; H, 5.99; N, 6.68.

Bis-1,2-{(5,6-dihydro-5,11-diketo-11H-indeno[1,2-c]isoquinoline)-(6-propyl-tert-BOCamino)}ethane (13b), N,N'-Bis(3-aminopropyl)-1,2-ethanediamine (11h) (0.16 g, 0.85 mmol) was added to a stirred solution of indenobenzopyran 4d (0.46 g, 1.87 mmol) in CHCl$_3$ (150 mL) and the reaction mixture was stirred under reflux for 72 h, providing bisindenoisoquinoline 12 h as a crude intermediate. Upon allowing the reaction mixture to cool to room temperature, Et$_3$N (0.6 mL, 4.24 mmol) and Boc$_2$O (0.56 g, 2.60 mmol) were added to the reaction mixture and the mixture was allowed to stir at room temperature for 8 h. The crude reaction mixture was purified by flash column chromatography (SiO$_2$/20% EtOAc in hexane, then 1-5% MeOH in CHCl$_3$) to provide Boc-protected bisindenoisoquinoline 13b (550 mg, 76%) as an orange solid: mp 106-108° C. $^1$HNMR (CDCl$_3$) δ 8.60 (bs, 2H), 8.23 (bs, 2H), 7.65 (bs, 2H), 7.55 (d, J=6.7 Hz, 2H), 7.40-7.32 (m, 8H), 4.48 (bs, 4H), 3.45 (bs, 8H), 2.12 (bs, 4H), 1.44 (s, 9H), 1.39 (s, 9H); ESIMS m/z (rel intensity) 835 (MH$^+$, 22), 735 (MH$^+$-Boc, 100). Anal. Calcd for C$_{50}$H$_{50}$N$_4$O$_8$·0.3H$_2$O: C, 71.46; H, 6.07; N, 6.67. Found: C, 71.15; H, 6.19; N, 6.61.

Bis-1,3-{(5,6-dihydro-5,11-diketo-11H-indeno[1,2-c]isoquinoline)-(6-propyl-tert-BOCamino)}propane (13c). N,N'-Bis(3-aminopropyl)-1,3-propanediamine (11j) (0.15 g, 0.74 mmol) was added to a stirred solution of indenobenzopyran 4d (0.40 g, 1.63 mmol) in CHCl$_3$ (150 mL) and the reaction mixture was stirred under reflux for 72 h, providing bisindenoisoquinoline 12j as a crude intermediate. Upon allowing the reaction mixture to cool to room temperature, Et$_3$N (0.53 mL, 3.78 mmol) and Boc$_2$O (0.49 g, 2.27 mmol) were added to the reaction mixture and the mixture was allowed to stir at room temperature for 8 h. The crude reaction mixture was purified by flash column chromatography (SiO$_2$/20% EtOAc in hexane, then 1-5% MeOH in CHCl$_3$) to provide Boc-protected bisindenoisoquinoline 13c (450 mg, 70%) as an orange solid: mp 86-88° C., $^1$H NMR (CDCl$_3$) δ 8.63 (d, J=8.1 Hz, 2H), 8.24 (d, J=7.6 Hz, 2H), 7.65 (t, J=7.3 Hz, 2H), 7.55 (d, J=6.7 Hz, 2H), 7.40-7.31 (m, 8H), 4.49 (bs, 4H), 3.44 (bs, 4H), 3.27 (apparent t, J=6.2 Hz, 4H), 2.08 (bs, 4H), 1.86 (bs, 2H), 1.41 (bs, 18H); ESIMS m/z (relative intensity) 849 (MH$^+$, 3), 749 (MH$^+$-Boc, 37), 649 (MH$^+$-2×Boc, 100). Anal.

Calcd for $C_{51}H_{52}N_4O_8 \cdot 0.5H_2O$: C, 71.39; H, 6.23; N, 6.53. Found: C, 70.99; H, 6.20; N, 6.62.

Bis-1,4-{(5,6-dihydro-5,11-diketo-11H-indeno[1,2-c]isoquinoline)-(6-propyl-tert-BOCamino)}butane (13d). N,N'-Bis(3-aminopropyl)-1,4-butanediamine (11k) (0.10 g, 0.50 mmol)) was added to a stirred solution of indenobenzopyran 4d (0.27 g, 1.09 mmol) in CHCl$_3$ (150 mL) and the reaction mixture was stirred under reflux for 72 h, providing bisindenoisoquinoline 12k as a crude intermediate. Upon allowing the reaction mixture to cool to room temperature, Et$_3$N (0.28 mL, 2.00 mmol) and Boc$_2$O (0.27 g, 1.25 mmol) were added to the reaction mixture and the mixture was allowed to stir at room temperature for 8 h. The crude reaction mixture was purified by flash column chromatography (SiO$_2$/20% EtOAc in hexane, and then 1-5% MeOH in CHCl$_3$) to provide Boc-protected bisindenoisoquinoline 13d (350 mg, 82%) as an orange solid: mp 92-94° C. $^1$H NMR (CDCl$_3$) δ 8.66 (d, J=8.1 Hz, 2H), 8.28 (d, J=8.0 Hz, 2H), 7.68 (t, J=7.7 Hz, 2H), 7.60 (d, J=7.1 Hz, 2H), 7.43-7.34 (m, 8H), 4.51 (t, J=8.3 Hz, 4H), 3.44 (bs, 4H), 3.28 (bs, 4H), 2.11 (m, 4H), 1.50 (bs, 4H), 1.41 (s, 18H); ESIMS m/z (rel intensity) 863 (MH$^+$, 13), 763 (MH$^+$-Boc, 100). Anal. Calcd for $C_{52}H_{54}N_4O_8 \cdot 0.9H_2O$: C, 71.04; H, 6.40; N, 6.37. Found: C, 70.77; H, 6.39; N, 6.26.

Bis{(5,6-dihydro-5,11-diketo-11H-indeno[1,2-c]isoquinoline)}-(6-ethyl,6'-propyl)ammonium Trifluoroacetate (14a). Bisindenoisoquinoline 12b (0.5 g, 0.87 mmol) was dissolved in neat CF$_3$COOH (30 mL) and the reaction mixture was stirred at room temperature for 1 h. The reaction mixture was concentrated, diluted with chloroform (50 mL), and the resultant solid was filtered through a sintered glass funnel and further washed with methanol (50 mL) to give bisindenoisoquinoline 14a (0.48 g, 80%) as a red solid: mp 240-242° C. $^1$H NMR (DMSO-d$_6$) δ 8.71 (bs, 1H, —NH—), 8.56 (d, J=7.8 Hz, 2H), 8.17 (d, J=8.6 Hz, 2H), 7.83-7.75 (m, 4H), 7.57-7.50 (m, 8H), 4.79 (bs, 2H), 4.57 (bs, 2H), 3.46 (bs, 2H), 3.17 (bs, 2H), 2.18 (bs, 2H); ESIMS m/z (rel intensity) 578 (MH$^+$-CF$_3$COOH, 100). Anal. Calcd for $C_{39}H_{28}N_3O_6F_3 \cdot 0.3H_2O$: C, 67.20; H, 4.14; N, 6.03. Found: C, 66.85; H, 4.12; N, 5.93.

Bis{(5,6-dihydro-5,11-diketo-11H-indeno[1,2-c]isoquinoline)}-(6-propyl,6'-butyl)amine Hydrochloride (14b). 2 M HCl in ether (6.2 mL, 2.4 mmol) was added to a stirred solution of bisindenoisoquinoline 12e (0.5 g, 0.83 mmol) in chloroform (100 mL) and the reaction mixture was stirred at room temperature for 2 h. The reaction mixture was filtered through a sintered glass funnel and the solid was washed with chloroform (50 mL) and methanol (50 mL) to give bisindenoisoquinoline hydrochloride 14b (0.44 g, 83%) as an orange solid: mp 280-282° C. (dec). $^1$H NMR (DMSO-d$_6$) δ 8.66 (bs, 1H), 8.54 (d, J=7.9 Hz, 2H), 8.18 (d, J=8.6 Hz, 2H), 7.53-7.7 d 0 (m, 4H), 7.58-7.40 (m, 8H), 4.54-4.42 (m, 4H), 3.06 (bs, 2H), 2.96 (bs, 2H), 2.16 (bs, 2H), 1.84 (bs, 2H), 1.76 (bs, 2H); ESIMS m/z (rel intensity) 606 (MH$^+$, 100). Anal. Calcd for $C_{39}H_{32}N_3O_4Cl \cdot 1.1H_2O$: C, 70.76; H, 5.21; N, 6.35. Found: C, 70.48; H, 5.12; N, 6.23.

Bis-1,2-{(5,6-dihydro-5,11-diketo-11H-indeno[1,2-c]isoquinoline)-6-ethylamino}ethane Bis(trifluoroacetate) (14c). N,N'-Bis(2-aminoethyl)-1,2-ethanediamine (11f) (0.4 g, 2.74 mmol) was added to a stirred solution of indenobenzopyran 4d (1.49 g, 6.02 mmol) in CHCl$_3$ (200 mL) and the reaction mixture was stirred under reflux for 48 h. The reaction mixture was then cooled and the resultant orange solid was filtered through a sintered glass funnel and washed with chloroform (50 mL) to provide bisindenoisoquinoline 12f (0.57 g, 69%) as an insoluble orange solid. Intermediate 12f (0.5 g, 0.83 mmol) was dissolved in neat CF$_3$COOH (30 mL) and stirred at room temperature for 30 min. The reaction mixture was concentrated, diluted with chloroform (50 mL), and filtered through a sintered glass funnel to provide bisindenoisoquinoline 14c (0.57 g, 83%) as an orange solid: mp 230-232° C. $^1$H NMR (DMSO-d$_6$) δ 8.97 (bs, 2H), 8.59 (d, J=8.1 Hz, 2H), 8.23 (d, J=8.0 Hz, 2H), 7.89-7.83 (td, J=1.2 and 8.3 Hz, 2H), 7.76 (d, J=6.8 Hz, 2H), 7.63-7.50 (m, 8H), 4.83 (bs, 4H), 3.52 (bs, 4H), 3.32 (bs, 4H); ESIMS m/z (rel intensity) 607 (MH$^+$, 100). Anal. Calcd for $C_{42}H_{12}N_4O_8F_6 \cdot 0.4H_2O$: C, 59.92; H, 3.93; N, 6.66. Found: C, 59.56; H, 4.04; N, 6.62.

Bis-1,3-{(5,6-dihydro-5,11-diketo-11H-indeno[1,2-c]isoquinoline)-6-ethylamino}propane Bis(trifluoroacetate) (14d). Boc-protected bisindenoisoquinoline 13a (0.3 g, 0.36 mmol) was dissolved in neat CF$_3$COOH (30 mL) and the mixture was stirred at room temperature for 1 h. The reaction mixture was concentrated and the resultant solid was diluted with chloroform (50 mL) and filtered through a sintered glass funnel to provide bisindenoisoquinoline 14d (0.28 g, 92%) as an orange solid: mp 244-246° C. $^1$H NMR (DMSO-d$_6$) δ 8.93 (bs, 2H), 8.60 (d, J=8.4 Hz, 2H), 8.23 (d, J=7.9 Hz, 2H), 7.87 (t, J=7.5 Hz, 2H), 7.79 (d, J=7.8 Hz, 2H), 7.60-7.52 (m, 8H), 4.82 (bs, 4H), 3.47 (bs, 4H), 3.07 (bs, 4H), 1.95 (bs, 2H); ESIMS m/z (rel intensity) 621 (MH$^+$, 100), 274 (7). Anal. Calcd for $C_{43}H_{34}F_6N_4O_8 \cdot 1.7H_2O$: C, 58.73; H, 4.29; N, 6.37. Found: C, 58.38; H, 4.32; N, 6.26.

Bis-1,2-{(5,6-dihydro-5,11-diketo-11H-indeno[1,2-c]isoquinoline)-6-propylamino}ethane Bis(trifluoroacetate) (14e). Boc-protected bisindenoisoquinoline 13b (0.5 g, 0.79 mmol) was dissolved in neat CF$_3$COOH (30 mL) and the mixture was stirred at room temperature for 30 min. The reaction mixture was concentrated, diluted with chloroform (50 mL), and the resultant solid was filtered through a sintered glass funnel to afford bisindenoisoquinoline 14e (0.61 g, 90%) as a pale red solid: mp 220-222° C. $^1$H NMR (DMSO-d$_6$) δ 8.84 (bs, 2H), 8.57 (d, J=8.1 Hz, 2H), 8.20 (d, J=7.8 Hz, 2H), 7.85-7.77 (m, 4H), 7.60-7.48 (m, 8H), 4.57 (t, J=6.6 Hz, 4H), 3.23 (bs, 4H), 3.18 (bs, 4H), 2.16 (m, 4H); ESIMS m/z (rel intensity) 635 (MH$^+$, 61). Anal. Calcd for $C_{44}H_{36}N_4O_8F_6 \cdot 1.4H_2O$: C, 59.51; H, 4.40; N, 6.31. Found: C, 59.15; H, 4.06; N, 6.06.

Bis-1,4-{(5,6-dihydro-5,11-diketo-11H-indeno[1,2-c]isoquinoline)-6-propyl}piperazine Bis(trifluoroacetate) (14f). 1,4-Bis(3-aminopropyl)piperazine 11i (0.10 g, 0.50 mmol) was added to a stirred solution indenobenzopyran 4d (0.27 g, 1.10 mmol) in CHCl$_3$ (150 mL) and the reaction mixture was stirred under reflux for 60 h. The reaction mixture was then cooled and the resultant red solid was filtered off through a sintered glass funnel, washed with chloroform (50 mL) and dried to provide intermediate 12i. This compound was further treated with CF$_3$COOH (40 mL) and the mixture was stirred at room temperature for 2 h. The reaction mixture was concentrated, diluted with chloroform (50 mL), and the resultant solid was filtered and washed with methanol-chloroform (1:9) to provide bisindenoisoquinoline 14f (430 mg, 86%) as red solid: mp 256-258° C. $^1$H NMR (CDCl$_3$) δ 8.57 (d, J=8.0 Hz, 2H), 8.21 (d, J=8.1 Hz, 2H), 7.85-7.77 (m, 4H), 7.58-7.48 (m, 8H), 4.55 (bs, 4H), 3.34 (bs, 4H), 3.02 (bs, 4H), 2.72 (bs, 2H), 2.47 (bs, 2H, merged with DMSO-d$_6$ protons), 2.09 (bs, 4H); ESIMS m/z (rel intensity) 661 (MH$^+$, 100). Anal. Calcd for $C_{46}H_{38}F_6N_4O_8 \cdot 0.4H_2O$: C, 61.66; H, 4.37; N, 6.25. Found: C, 61.27; H, 4.61; N, 6.18.

Bis-1,3-{(5,6-dihydro-5,11-diketo-11H-indeno[1,2-c]isoquinoline)-6-propylamino}propane Bis(trifluoroacetate) (14g). Boc-protected bisindenoisoquinoline 13c (0.3 g, 0.35 mmol) was dissolved in neat CF$_3$COOH (30 mL) and the mixture was stirred at room temperature for 1 h. The reaction mixture was concentrated and the resultant solid was diluted with chloroform (50 mL) and filtered through a sintered glass funnel to provide bisindenoisoquinoline 14g (0.27 g, 89%) as an orange solid: mp 225-227° C., $^1$H NMR (DMSO-d$_6$) δ 8.66 (bs, 2H), 8.56 (d, J=8.1 Hz, 2H), 8.19 (d, J=7.9 Hz, 2H), 7.79 (t, J=7.9 Hz, 4H), 7.59-7.48 (m, 8H), 4.57 (bs, 4H), 3.09 (bs, 4H), 2.96 (bs, 4H), 2.15 (bs, 4H), 1.87 (bs, 2H); ESIMS m/z (relative intensity) 649 (MH$^+$, 100). Anal. Calcd for C$_{45}$H$_{38}$F$_6$N$_4$O$_8$·1.3H$_2$O: C, 60.04; H, 4.55; N, 6.22. Found: C, 59.71; H, 4.41; N, 6.03.

Bis-1,4-{(5,6-dihydro-5,11-diketo-11H-indeno[1,2-c]isoquinoline)-6-propylamino}butane Bis(trifluoroacetate) (14h). Boc-protected bisindenoisoquinoline 13d (0.3 g, 0.35 mmol) was dissolved in neat CF$_3$COOH (20 mL) and the mixture was stirred at room temperature for 1 h. The reaction mixture was concentrated and the resultant solid was diluted with chloroform (50 mL) and filtered through a sintered glass funnel to provide bisindenoisoquinoline 14h (0.28 g, 90%) as an orange solid: mp 236-238° C. $^1$H NMR (DMSO-d$_6$) δ 8.58 (d, J=8.0 Hz, 2H), 8.52 (bs, 2H), 8.20 (d, J=8.1 Hz, 2H), 7.84-7.78 (m, 4H), 7.60-7.49 (m, 8H), 4.57 (t, J=6.6 Hz, 4H), 3.08 (bs, 4H), 2.92 (bs, 4H), 2.16 (m, 4H), 1.59 (bs, 4H); ESIMS m/z (rel intensity) 663 (MH$^+$, 100). Anal. Calcd for C$_{46}$H$_{40}$F$_6$N$_4$O$_8$·0.4H$_2$O: C, 61.52; H, 4.58; N, 6.24. Found: C, 61.22; H, 4.62; N, 6.09.

Bis{(5,6-dihydro-5,11-diketo-11H-indeno[1,2-c]isoquinoline)-6-ethylamino-ethyl}amine Tris(trifluoroacetate) (14i). N-(2-aminoethyl)-N'-[(2-aminoethyl)aminoethyl)]-1, 2-ethanediamine (11l) (0.20 g, 1.06 mmol) was added to a stirred solution of indenobenzopyran 4d (0.58 g, 2.32 mmol) in CHCl$_3$ (150 mL) and the reaction mixture was stirred under reflux for 4 days, providing bisindenoisoquinoline 12l as a crude intermediate. Upon allowing the reaction mixture to cool to room temperature, Et$_3$N (0.86 mL, 6.13 mmol) and Boc$_2$O (0.89 g, 4.09 mmol) were added and the mixture was allowed to stir at room temperature for 12 h. The crude reaction mixture was purified by flash column chromatography (SiO$_2$/20% EtOAc in hexane, then 1-3% MeOH in CHCl$_3$) to provide Boc-protected bisindenoisoquinoline 13e (0.61 g, 61%), which was further treated with neat CF$_3$COOH (30 mL) and stirred at room temperature for 3 h. The reaction mixture was concentrated and the resultant solid was diluted with chloroform (50 mL) and filtered through a sintered glass funnel to provide bisindenoisoquinoline 14i (0.42 g, 66%) as red solid: mp 198-200° C. (dec). $^1$H NMR (DMSO-d$_6$) δ 8.55 (d, J=8.1 Hz, 2H), 8.20 (d, J=7.6 Hz, 2H), 7.85-7.76 (m, 4H), 7.59-7.48 (m, 8H), 4.81 (bs, 4H), 3.54 (bs, 4H), 3.32 (bs, 8H); ESIMS m/z (rel intensity) 650 (MH$^+$, 100). Anal. Calcd for C$_{46}$H$_{38}$N$_5$O$_{10}$F$_9$·0.6CH$_2$Cl$_2$NH$_3$: C, 53.15; H, 3.93; N, 7.45. Found; C, 53.16; H, 4.27; N, 7.81.

Bis-1,2-{(5,6-dihydro-5,11-diketo-11H-indeno[1,2-c]isoquinoline)-6-ethylamino-ethylamino}ethane Tetra(trifluoroacetate) (14j). N,N'-Bis[(2-aminoethyl)aminoethyl)]-1,2-ethanediamine (11m) (0.20 g, 0.86 mmol) was added to a stirred solution of indenobenzopyran 4d (0.47 g, 1.89 mmol) in CHCl$_3$ (150 mL) and the reaction mixture was stirred under reflux for 4 days, providing bisindenoisoquinoline 12m as a crude intermediate. Upon allowing the reaction mixture to cool to room temperature, Et$_3$N (1.21 mL, 8.67 mmol) and Boc$_2$O (0.95 g, 4.34 mmol) were added to the reaction mixture and the mixture was allowed to stir at room temperature for 12 h. The crude reaction mixture was purified by flash column chromatography (SiO$_2$/20% EtOAc in hexane, then 1-3% MeOH in CHCl$_3$) to provide Boc-protected bisindenoisoquinoline 13f (0.62 g, 66%), which was further treated with neat CF$_3$COOH (30 mL) and stirred at room temperature for 3 h. The reaction mixture was concentrated and the resultant solid was diluted with chloroform (50 mL) and filtered through a sintered glass funnel to provide bisindenoisoquinoline 14j (0.48 g, 49%) as red solid: mp 206-208° C. (dec). $^1$H NMR (DMSO-d$_6$) δ 8.55 (t, J=8.4 Hz, 2H), 8.19 (t, J=8.0 Hz, 2H), 7.82-7.61 (m, 4H), 7.59-7.51 (m, 8H), 4.81 (bs, 4H), 3.52 (bs, 4H), 3.27 (bs, 4H), 3.19-3.13 (bs, 8H); ESIMS m/z (rel intensity) 693 (MH$^+$, 100). Anal. Calcd for C$_{50}$H$_{44}$N$_6$O$_{12}$F$_{12}$·0.6H$_2$O: C, 51.78; H, 3.93; N, 7.25. Found: C, 51.41; H, 4.17; N, 7.53.

Bis-1,3-{(5,6-dihydro-5,11-diketo-2,3-dimethoxy-11H-indeno[1,2-c]isoquinoline)-6-ethylamino}propane Bis{trifluoroacetate) (14k). N,N'-Bis(2-aminoethyl)-1,3-propanediamine (11g) (01050 g, 0.309 mmol) was added to a solution of 2,3-dimethoxybenz[d]indeno[1,2-b]pyran-5,11-dione (4a) (0.200 g, 0.649 mmol) in CHCl$_3$ (50 mL). The solution was heated at reflux for 72 h and cooled to room temperature. Triethylamine (0.17 mL) and Boc$_2$O (0.270 g, 1.236 mmol) were added to the solution and stirring was continued at room temperature for 16 h. The solution was washed with water (2×25 mL) and sat NaCl (25 mL), dried over sodium sulfate, and concentrated. The crude red solid was purified by flash column chromatography (SiO$_2$/CHCl$_3$ to 3% MeOH in CHCl$_3$) followed by precipitation from CH$_2$Cl$_2$-hexanes to provide a pink solid. The obtained pink solid was diluted with trifluoroacetic acid (30 mL) and the mixture was stirred at room temperature for 16 h. The solution was concentrated, diluted with CHCl$_3$ (50 mL) and filtered to provide a red solid (0.257 g, 86%): mp 225-228° C. IR (KBr) 3437, 1652, 1553, 1513, 1429, 1268, 1204, and 1021 cm$^{-1}$; $^1$H NMR (DMSO-d$_6$) δ 7.96 (s, 2H), 7.72-7.69 (bs, 2H), 7.52-7.43 (m, 8H), 4.71 (bs, 4H), 3.92 (s, 6H), 3.81 (s, 6H), 3.06 (bs, 4H), 1.99 (bs, 2H); ESIMS m/z (rel intensity) 741 (MH$^+$, 100). Anal. Calcd for C$_{47}$H$_{42}$F$_6$N$_4$O$_{12}$·4H$_2$O: C, 54.23; H, 54.83: N, 5.38. Found: C, 54.63; H, 4.49; N, 5.47.

Bis-1,3-{(5,6-dihydro-5,11-diketo-2,3-dimethoxy-11H-indeno[1,2-c]isoquinoline)-6-propylamino}propane Bis{trifluoroacetate) (14l). N,N'-Bis(3-aminopropyl)-1,3-propanediamine (11j) (0.058 g, 0.309 mmol) was added to a solution of indenobenzopyran 4a (0.200 g, 0.649 mmol) in CHCl$_3$ (50 mL). The solution was heated at reflux for 72 h and cooled to room temperature. Triethylamine (0.17 mL) and Boc$_2$O (0.270 g, 1.236 mmol) were added to the solution and stirring was continued at room temperature for 16 h. The solution was washed with water (2×25 mL) and sat NaCl (25 mL), dried over sodium sulfate, and concentrated. The crude orange solid was purified by flash column chromatography (SiO$_2$/CHCl$_3$ to 3% MeOH in CHCl$_3$) followed by precipitation from EtOAc to provide an orange solid. The obtained orange solid was diluted with trifluoroacetic acid (30 mL) and the mixture was stirred at room temperature for 16 h. The solution was concentrated, diluted with CHCl$_3$ (50 mL) and filtered to provide a red solid (0.221 g, 72%): mp 273-276° C. (dec). IR (KBr) 3436, 1639, 1553, 1512, 1478, 1429, 1267, 1184, and 1022 cm$^{-1}$; $^1$H NMR (DMSO-d$_6$) δ 8.43 (bs, 4H), 8.00 (s, 2H), 7.76 (d, J=7.58 Hz, 2H), 7.59-7.45 (m, 8H), 4.56 (bs, 4H), 3.93 (s, 6H), 3.85 (s, 6H), 3.09 (bs, 4H), 2.98 (bs, 4H), 2.15 (bs, 4H), 1.86 (bs, 2H); ESIMS m/z (rel intensity) 769 (MH$^+$, 100). Anal. Calcd for C$_{49}$H$_{46}$F$_6$N$_4$O$_{12}$·6H$_2$O: C, 53.26; H, 5.29; N, 5.07. Found: C, 52.88; H, 4.96; N, 5.21.

Bis-1,3-{(5,6-dihydro-5,11-diketo-3-nitro-11H-indeno[1, 2-c]isoquinoline)-6-ethylamino}propane Bis{trifluoroacetate) (14m). N,N'-Bis(2-aminoethyl)-1,3-propanediamine (11g) (0.056 g, 0.349 mmol) was added to a solution of indenobenzopyran 4c (0.225 g, 0.767 mmol) in CHCl$_3$ (50 mL). The solution was heated at reflux for 72 h and cooled to room temperature. Triethylamine (0.19 mL) and Boc$_2$O (0.305 g, 1.396 mmol) were added to the solution and stirring was continued at room temperature for 16 h. The solution was washed with water (2×30 mL) and sat NaCl (30 mL), dried over sodium sulfate, and concentrated. The crude orange solid was purified by flash column chromatography (SiO$_2$/CHCl$_3$ to 3% MeOH CHCl$_3$) to provide an orange solid. The orange solid was diluted with trifluoroacetic acid (40 mL) and the mixture was stirred at room temperature for 24 h. The solution was concentrated, diluted with CHCl$_3$ (50 mL) and filtered to provide an orange solid (0.221 g, 67%): mp 227-230° C. (dec). IR (KBr) 3433, 3087, 3022, 2819, 1679, 1615, 1560, 1505, 1429, 1138, and 1200 cm$^{-1}$; $^1$H NMR (CDCl$_3$) δ 8.90 (bs, 4H), 8.79 (d, J=9.14 Hz, 2H), 8.66 (d, J=9.07 Hz, 2H), 7.93 (d, J=6.54 Hz, 2H), 7.74 (d, J=7.17 Hz, 2H), 7.67 (m, 4H), 4.87 (bs, 4H), 3.49 (bs, 4H), 3.09 (bs, 4H), 1.91 (bs, 2H); ESIMS m/z (rel intensity) 711 (MH$^+$, 100). Anal. Calcd for C$_{43}$H$_{32}$F$_6$N$_6$O$_{12}$.0.5H$_2$O: C, 54.49; H, 3.51; N, 8.87. Found: C, 54.24; H, 3.80; N, 8.86.

Bis-1,3-{(5,6-dihydro-5,11-diketo-3-nitro-11H-indeno[1,2-c]isoquinoline)-6-propylamino}propane Bis{trifluoroacetate} (14n). N,N'-Bis(3-aminopropyl)-1,3-propanediamine (11j) (0.064 g, 0.341 mmol) was added to a solution of indenobenzopyran 4c (0.200 g, 0.682 mmol) in CHCl$_3$ (75 mL). The solution was heated at reflux for 72 h and cooled to room temperature. Triethylamine (0.19 mL) and Boc$_2$O (0.298 g, 1.364 mmol) were added to the solution and stirring was continued at room temperature for 16 h. The solution was washed with water (2×30 mL) and sat NaCl (30 mL), dried over sodium sulfate, and concentrated. The crude orange solid was purified by flash column chromatography (SiO$_2$/CHCl$_3$ to 3% MeOH in CHCl$_3$) to provide an orange solid. The obtained orange solid was diluted with trifluoroacetic acid (40 mL) and stirred at room temperature for 2 h. The solution was concentrated, diluted with CHCl$_3$ (50 mL) and filtered to provide an orange solid (0.206 g, 62%): mp 220-223° C. IR (KBr) 1678, 1614, 1505, 1339, 1203, and 1132 cm$^{-1}$; $^1$H NMR (CDCl$_3$) δ 8.88 (d, J=2.5 Hz, 2H), 8.75 (d, J=9.0 Hz, 2H), 8.63 (bs, 2H), 8.60 (dd, J=9.0 Hz and 2.5 Hz, 2H), 7.92 (d, J=6.5 Hz, 2H), 7.70-7.61 (m, 6H), 4.64 (t, J=5.9 Hz, 4H), 3.15 (bs, 4H), 2.98 (bs, 4H), 2.19 (bs, 2H); ESIMS m/z (rel intensity) 739 (MH$^+$, 100). Anal. Calcd for C$_{45}$H$_{36}$F$_6$N$_6$O$_{12}$.3H$_2$O: C, 52.95; H, 4.15; N, 8.23. Found: C, 53.33; H, 4.32; N, 8.60.

1,3-{6-(3-tert-Butyloxycarbonylamino-1-propyl)-5,6-dihydro-2,3-dimethoxy-8,9-methylenedioxy-5,11-dioxo-11H-indeno[2-c]isoquinoline}-{5',6'-dihydro-6'-[(3'-tert-butyloxycarbonylamino)-1'-propyl]-5',11'-dioxo-11'H-indeno[1,2-c]isoquinoline}propane (16a). 5 M NaOH (aq) was added slowly to a solution of indenoisoquinoline hydrochloride A (1.0 g, 1.58 mmol) in a water-chloroform solution (2:1, 250 mL), which was prepared according to Nagarajan, M.; Xiao, X.; Antony, S.; Kohlhagen, G.; Pommier, Y.; Cushman, M., Design, Synthesis, and Biological Evaluation of Indenoisoquinoline Topoisomerase I Inhibitors Featuring Polyamine Side Chains on the Lactam Nitrogen, *J. Med. Chem.* 2003, 46, 5712-5724, the disclosure of which is hereby incorporated by reference. At a pH of 7-8, the organic layer was separated and the aqueous layer was extracted with chloroform (3×100 mL). The combined organic layers were washed with water (100 mL), sat NaCl (100 mL), dried over Na$_2$SO$_4$, and concentrated. Indenobenzopyran 4d (0.43 g, 1.74 mmol) was added to a solution of the crude indenoisoquinoline triamine A (0.70 g, 1.34 mmol) in chloroform (200 mL) and the reaction mixture was heated at reflux for 4 days. The reaction mixture containing crude, unsymmetrical bisindenoisoquinoline 15a was cooled to room temperature, Et$_3$N (0.93 mL, 6.64 mmol) and Boc$_2$O (0.87 g, 3.98 mmol) were added, and the solution was allowed to stir at room temperature for 12 h. The crude reaction mixture was purified by flash column chromatography (SiO$_2$/20% EtOAc in hexane, then 1-3% MeOH in CHCl$_3$) to provide Boc-protected bisindenoisoquinoline 16a (0.72 g, 48%) as purple solid: mp 120-122° C. $^1$H NMR (CDCl$_3$) δ 8.64 (d, J=8.3 Hz, 1H), 8.24 (d, J=5.7 Hz, 1H), 7.94 (s, 1H), 7.67 (t, J=7.4 Hz, 1H), 7.58 (s, 1H), 7.56 (s, 1H), 7.42-7.34 (m, 5H), 6.99 (s, 1H), 6.05 (s, 2H), 4.49 (bs, 2H), 4.40 (bs, 2H), 4.01 (s, 3H), 3.92 (s, 3H), 3.45 (bs, 4H), 3.29 (bs, 4H), 2.10 (bs, 4H), 1.87 (m, 2H), 1.42 (s, 18H); ESIMS m/z (rel intensity) 953 (MH$^+$, 30), 853 (MH$^+$-Boc, 100). Anal. Calcd for C$_{54}$H$_{56}$N$_4$O$_{12}$.0.9CHCl$_3$: C, 62.18; H, 5.41; N, 5.28. Found: C, 62.08; H, 5.36; N, 5.15.

1,3-{6-(3-Amino-1-propyl)-5,6-dihydro-2,3-dimethoxy-8,9-methylenedioxy-5,11-dioxo-11H-indeno[1,2-c]isoquinoline}-{5',6'-Dihydro-6'-(3'-amino-1'-propyl)-5',11'-dioxo-11'H-indeno[1,2-c]isoquinoline}propane Bis (trifluoroacetate) (17a). Boc-protected bisindenoisoquinoline 16a (0.55 g, 0.58 mmol) was dissolved in neat CF$_3$COOH (30 mL) and the mixture was stirred at room temperature for 3 h. The reaction mixture was concentrated and the resultant solid was diluted with chloroform (50 mL) and filtered through a sintered glass funnel to provide bisindenoisoquinoline 17a (0.43 g, 76%) as purple solid: mp 218-220° C. $^1$H NMR (DMSO-d$_6$) δ 8.65 (bs, 2H), 8.53 (d, J=8.0 Hz, 1H), 8.17 (d, J=7.2 Hz, 1H), 7.80-7.75 (m, 3H), 7.55-7.50 (m, 4H), 7.39 (s, 1H), 7.32 (s, 1H), 7.02 (s, 1H), 6.18 (s, 2H), 4.55 (bs, 2H), 4.45 (bs, 2H), 3.86 (s, 3H), 3.81 (s, 3H), 3.07-2.98 (bs, 8H), 2.14 (bs, 4H), 1.89 (bs, 2H); ESIMS m/z (rel intensity) 753 (MH$^+$, 100). Anal. Calcd for C$_{48}$H$_{42}$N$_4$O$_{12}$F$_6$.3.1H$_2$O: C, 55.61; H, 4.69; N, 5.40. Found: C, 55.24; H, 4.36; N, 5.36.

General Procedure for the Preparation of Compounds 18-31

General. Solvents and reagents were purchased from commercial vendors and were used without any further purification. Melting points were determined using capillary tubes with a Mel-Temp apparatus and are uncorrected. Infrared spectra are obtained using KBr pellets. IR spectra were recorded using a Perkin-Elmer 1600 series or Spectrum One FTIR spectrometer. $^1$H NMR spectra were recorded at 300 MHz using a Broker ARX300 spectrometer with a QNP probe. Mass spectral analyses were performed at the Purdue University Campus-Wide Mass Spectrometry Center. ESI-MS studies were performed using a FinniganMAT LCQ Classic mass spectrometer. EI/CI-MS studies were performed using a Hewlett-Packard Engine or GCQ FinniganMAT mass spectrometer. APCI-MS studies were carried out using an Agilent 6320 Ion Trap mass spectrometer. Analytical thin layer chromatography was carried out on Baker-flex silica gel IB2-F plates, and compounds were visualized with short wavelength UV light and ninhydrin staining. Silica gel flash chromatography was performed using 230-400 mesh silica gel. HPLC analyses were performed on a Waters 1525 binary HPLC pump/Waters 2487 dual λ absorbance detector system using a 5 μM C$_{18}$ reverse phase column. Compound purities were estimated by reversed phase C$_{18}$ HPLC, with UV detector at 254 nm, and the major peak area of each tested compound was ≥95% of the combined total peak area. All yields refer to isolated compounds.

2-(3-Bromopropoxy)-3-methoxy-6-(3-morpholinopropyl)-5H-[1,3]dioxolo[4',5':5,6]indeno[1,2-c]isoquinoline-5,12(6H)-dione (19). A solution of compound 18 (0.100 g, 0.216 mmol) in DMF (6 mL) (Nagarajan, et al. *J. Med. Chem.* 2003, 46, 5712-5724) was treated with sodium hydride (0.011 g, 2.16 mmol). After 10 min, 1,3-dibromopropane was added. The mixture was stirred at room temperature for 3 h. The mixture was diluted to a volume of 200 mL with CHCl$_3$, washed with H$_2$O (2×50 mL) and saturated aq NaCl (50 mL), dried over anhydrous sodium sulfate, and concentrated. The residue was purified by flash column chromatography (SiO$_2$, ~40 g), eluting with a gradient of 1% MeOH in CHCl₃, to yield compound 19 as a solid (0.071 g, 56%): mp 197-199° C. IR (film) 3434, 2102, 1638, 1498, 1304, 1115, 1032 cm⁻¹; ¹H NMR (CDCl₃) δ 8.02 (s, 1H), 7.62 (s, 1H), 7.38 (s, 1H), 7.04 (s, 1H), 6.15 (s, 2H), 5.58-5.37 (m, 2H), 4.79-4.77 (d, J=5.1 Hz, 2H), 4.69-4.52 (t, J=8.4 Hz, 2H), 3.97 (s, 3H), 3.77 (s, 4H), 2.55 (s, 6H), 2.02 (s, 2H), 1.33 (s, 2H); ESIMS m/z 585/587 (MH⁺), 505 (MH⁺—HBr); HRESIMS m/z 585.1236 (MH⁺), calcd for $C_{28}H_{30}BrN_2O_7$ 585.1243.

2-(Allyloxy)-3-methoxy-6-(3-morpholinopropyl)-5H-[1,3]dioxolo[4',5':5,6]indeno[1,2-c]isoquinoline-5,12(6H)-dione (20). Column chromatography of the mixture described above also yielded the side product 20 as a solid (0.013 g, 10%): mp 199-200° C. (dec). IR (film) 2936, 1749, 1698, 1651, 1304, 1034, 786 cm⁻¹; ¹H NMR (CDCl₃) δ 8.01 (s, 1H), 7.61 (s, 1H), 7.37 (s, 1H), 7.03 (s, 1H), 6.08 (s, 3H), 5.53-5.40 (m, 2H), 4.79-4.77 (d, J=5.7 Hz, 2H), 4.51-4.45 (t, J=7.5 Hz, 2H), 3.97 (s, 3H), 3.77 (s, 4H), 2.54 (s, 6H), 2.01 (s, 2H); ESIMS m/z 505 (MH⁺); HRESIMS m/z 505.1967 (MH⁺), calcd for $C_{28}H_{29}N_2O_7$ 505.1975. HPLC purity: 97.57% (C-18 reverse phase, MeOH—H₂O, 90:10).

2-(3-Azidopropoxy)-3-methoxy-6-(3-morpholinopropyl)-5H-[1,3]dioxolo[4',5':5,6]indeno[1,2-c]isoquinoline-5,12(6H)-dione (21). Sodium azide (0.021 g, 0.22 mmol) and compound 19 (0.128 g, 0.22 mmol) were diluted with DMSO (4 mL), and the mixture was heated at 100° C. for 2 h. The mixture was diluted to a volume of 200 mL with CHCl₃, washed with H₂O (2×60 mL) and saturated aq NaCl (50 mL), dried over anhydrous sodium sulfate, and concentrated. The resulting residue was purified by flash column chromatography (SiO₂, ~40 g), eluting with a gradient of 0.5% MeOH in CHCl₂, to yield the product 21 as a solid (0.036 g, 60%). The solid was used for next step without further purification. ESIMS m/z 548 (MH⁺); HRESIMS m/z 548.2141 (MH⁺), calcd for $C_{28}H_{30}N_5O_7$ 548.2145.

2-(3-Aminopropoxy)-3-methoxy-6-(3-morpholinopropyl)-5H-[1,3]dioxolo[4',5':5,6]indeno[1,2-c]isoquinoline-5,12(6H)-dione (22). Triethyl phosphite (0.022 mL, 0.183 mmol) was added to a solution of the compound 21 (0.040 g, 0.073 mmol) in benzene (4 mL), and the mixture was heated at reflux for 24 h. The mixture was diluted to a volume of 200 mL with CHCl₃, washed with H₂O (2×50 mL) and saturated aq NaCl (50 mL), dried over anhydrous sodium sulfate, and concentrated. The resulting residue was purified by flash column chromatography (SiO₂, ~40 g), eluting with a gradient of 0.5% MeOH in CHCl₃, to yield the title compound as a solid. The solid (0.015 g, 0.023 mmol) was diluted with benzene (4 mL), and 2 M HCl in methanol (6 mL) was added to the solution. The mixture was heated at reflux for 3 h. The reaction mixture was allowed to cool to room temperature and the precipitate was filtered to provide the desired compound 22 as a solid (0.007 g, 58%): mp>350° C. IR (film) 3413, 2346, 1751, 1651, 1559, 1437, 1309, 737 cm⁻¹; ¹H NMR (D₂O) δ 6.77 (s, 1H), 6.62 (s, 1H), 6.56 (s, 1H), 6.16 (s, 1H), 5.96 (s, 2H), 4.86-4.82 (m, 2H), 4.01 (s, 6H), 3.78 (s, 2H), 3.67 (s, 3H), 3.32 (s, 4H), 3.24-3.19 (t, J=7.5 Hz, 2H), 2.19-2.17 (m, 4H); ESIMS m/z 522 (MH⁺); HRESIMS m/z 522.2249 (MH⁺), called for $C_{28}H_{32}N_3O_7$ 522.2246; HPLC purity: 95.23% (C-18 reverse phase, MeOH—H₂O, 85:15).

2-(3-(Dimethylamino)propoxy)-3-methoxy-6-(3-morpholinopropyl)-5H-[1,3]dioxolo[4',5':5,6]indeno[1,2-c]isoquinoline-5,12(6H)-dione (23). Sodium iodide (0.061 g, 0.408 mmol) and compound 19 (0.020 g, 0.034 mmol) were diluted with dioxane (10 mL), and dimethylamine (0.023 mL, 0.408 mmol) was added dropwise. The mixture was stirred at reflux for 52 h. The mixture was diluted to a volume of 250 mL with CHCl₃, washed with H₂O (2×50 mL) and saturated aq NaCl (50 mL), dried over anhydrous sodium sulfate, and concentrated. The residue was purified by flash column chromatography (SiO₂, ~40 g), eluting first with a gradient of 0.5% MeOH in CHCl₃, and then with 1% MeOH in CHCl₃, to yield the product 23 as a solid (0.009 g, 47%): mp 176-178° C. (dec). IR (film) 2922, 1698, 1650, 1483, 1306, 1032, 786 cm⁻¹; ¹H NMR (CDCl₃) δ 8.02 (s, 1H), 7.63 (s, 1H), 7.43 (s, 1H), 7.08 (s, 1H), 6.09 (s, 2H), 4.54-4.48 (t, 8.4 Hz, 2H), 4.29-4.25 (t, J=6.3 Hz, 2H), 3.95 (s, 3H), 3.78-3.74 (t, J=4.8 Hz, 2H), 2.57-2.53 (m, 14H), 2.27 (s, 2H), 2.03-2.02 (m, 2H); ESIMS m/550 (MH⁺); HRESIMS m/z 550.2558 (MH⁺), calcd for $C_{30}H_{36}N_3O_7$ 550.2553; HPLC purity: 97.57% (C-18 reverse phase. MeOH—H₂O, 85:15).

2-(3-(Ethylamino)propoxy)-3-methoxy-6-(3-morpholinopropyl)-5H-[1,3]dioxolo[4',5':5,6]indeno[1,2-c]isoquinoline-5,12(6H)-dione (24). Sodium iodide (0.060 g, 0.408 mmol) and compound 19 (0.020 g, 0.034 mmol) were diluted with dioxane (8 mL), and ethylamine (0.020 mL, 0.408 mmol, 70 wt. % solution in water) was added dropwise. The mixture was stirred at reflux for 26 h. The mixture was diluted to a volume of 200 mL with CHCl₃, washed with H₂O (2×50 mL) and saturated aq NaCl (50 mL), dried over anhydrous sodium sulfate, and concentrated. The residue was purified by flash column chromatography (SiO₂, ~40 g), eluting with a gradient of 0.5% MeOH in CHCl₃, to yield the product 24 as a solid (0.009 g, 46%): mp 187-188° C. (dec). IR (film) 1648, 1553, 1392, 1254, 1116, 1033, 785 cm⁻¹; ¹H NMR (CDCl₃) δ 7.53 (s, 1H), 7.24 (s, 1H), 6.90 (s, 1H), 6.60 (s, 1H), 5.89 (s, 2H), 4.06 (s, 2H), 3.85 (s, 6H), 3.72 (s, 3H), 3.49-3.38 (m, 4H), 3.19-3.12 (m, 9H), 2.25-2.19 (m, 4H); ESIMS m/z 550 (MH⁺); HRESIMS m/z 550.2553 (MH⁺), calcd for $C_{30}H_{36}N_3O_7$ 550.2553; HPLC purity: 98.36% (C-18 reverse phase, MeOH—H₂O, 80:20).

3-Methoxy-2-(3-morpholinopropoxy)-6-(3-morpholinopropyl)-5H-[1,3]dioxolo[4',5':5,6]indeno[1,2-c]isoquinoline-5,12(6H)-diene (25). Sodium iodide (0.139 g, 0.924 mmol) and compound 19 (0.045 g, 0.077 mmol) were diluted with dioxane (10 mL), and morpholine (0.08 mL, 0.924 mmol) was added dropwise. The mixture was stirred at reflux for 24 h. The mixture was diluted to a volume of 200 mL with CHCl₃, washed with H₂O (2×60 mL) and saturated aq NaCl (50 mL), dried over anhydrous sodium sulfate, and concentrated. The residue was purified by flash column chromatography (SiO₂, ~40 g), eluting first with a gradient of 0.5% MeOH in CHCl₃, and then with 1% MeOH in CHCl₃, to yield the product 25 as a solid (0.018 g, 41%): mp 188-189° C. (dec). IR (film) 2956, 1869, 1749, 1650, 1508, 1307, 1032, 865 cm⁻¹; ¹H NMR (CDCl₃) δ 7.99 (s, 1H), 7.61 (s, 1H), 7.39 (s, 1H), 7.04 (s, 1H), 6.08 (s, 2H), 4.64-4.51 (t, J=7.5 Hz, 2H), 4.28-4.24 (t, J=6.6 Hz, 2H), 3.95 (s, 3H), 3.76 (s, 8H), 2.53 (s, 12H), 2.15-2.11 (t, J=6.3 Hz, 2H), 2.01 (s, 2H); ESIMS m/z 592 (MH⁺); HRESIMS m/z 592.2664 (MH⁺), calcd for $C_{32}H_{38}N_3O_8$ 592.2659; HPLC purity: 95.38% (C-18 reverse phase, MeOH—H₂O, 85:15).

3-Methoxy-2-(3-(4-methylpiperazin-1-yl)propoxy)-6-(3-morpholinopropyl)-5H-[1,3]dioxolo[4',5':5,6]indeno[1,2-c]isoquinoline-5,12(6H)-diene (26). Sodium iodide (0.061 g, 0.408 mmol) and compound 14 (0.020 g, 0.034 mmol) were diluted with dioxane (5 mL), and N-methyl piperazine (0.041 mL, 0.408 mmol) was added dropwise. The mixture was stirred at reflux for 24 h. The mixture was diluted to a volume of 200 mL with CHCl₃, washed with H₂O (2×50 mL) and saturated aq NaCl (50 mL), dried over anhydrous sodium sulfate, and concentrated. The residue was purified by flash column chromatography (SiO₂, ~40 g), eluting first with a gradient of 0.5% MeOH in CHCl₃, and then with 3% MeOH in CHCl₃, to yield the product 26 as a solid (0.010 g, 49%):

mp 181-183° C. (dec). IR (film) 2924, 1870, 1650, 1508, 1307, 1032, 868 cm$^{-1}$; $^1$H NMR (CDCl$_3$) δ 8.01 (s, 1H), 7.62 (s, 1H), 7.42 (s, 1H), 7.06 (s, 1H), 6.09 (s, 2H), 4.53-4.47 (t, J=8.4 Hz, 2H), 4.28-4.23 (t, J=6.6 Hz, 2H), 3.95 (s, 3H), 3.77-3.74 (t, J=4.5 Hz, 2H), 2.62-2.53 (m, 16H), 2.35 (s, 3H), 2.13-2.06 (m, 2H), 2.05-2.00 (m, 2H); ESIMS m/z 605 (MH$^+$); HRESIMS m/z 605.2986 (MH$^+$), calcd for C$_{33}$H$_{41}$N$_4$O$_7$ 605.2975; HPLC purity: 100% (C-18 reverse phase, MeOH—H$_2$O, 90:10).

3-Methoxy-6-(3-morpholinopropyl)-2-(3-(piperidin-1-yl) propoxy)-5H-[1,3]dioxolo[4',5':5,6]indeno[1,2-c]isoquinoline-5,12(6H)-dione (27). 1-(3-chloropropyl)piperidine hydrochloride (214 mg, 1.08 mmol) and K$_2$CO$_3$ (298 mg, 2.16 mmol) were added to a DMF (5 mL) solution of compound 18 (0.100 g, 0.216 mmol). The mixture was heated at 90° C. for 23 h. The mixture was diluted to a volume of 300 mL with CHCl$_3$, washed with H$_2$O (2×80 mL) and saturated aq NaCl (80 mL), dried over anhydrous sodium sulfate, and concentrated. The residue was purified by flash column chromatography (SiO$_2$, ~40 g), eluting with a gradient of 0.25% MeOH in CHCl$_3$, to yield the product 27 as a solid (0.072 g, 58%): mp 156-157° C. (dec). IR (film) 3399, 2091, 1645, 1392, 1305 cm$^{-1}$; $^1$H NMR (CDCl$_3$) δ 7.99 (s, 1H), 7.60 (s, 1H), 7.39 (s, 1H), 7.04 (s, 1H), 6.08 (s, 2H), 4.51-4.46 (t, J=7.8 Hz, 2H), 4.25-4.21 (t, J=6.6 Hz, 2H), 3.95 (s, 3H), 3.77-3.74 (m, 4H), 2.58-2.46 (m, 12H), 2.18-2.09 (m, 2H), 2.04-1.95 (m, 2H), 1.61-1.58 (m, 4H), 1.46-1.44 (m, 2H); ESIMS m/z 590 (MH$^+$); HRESIMS m/z 590.2859 (MH$^+$), calcd for C$_{33}$H$_{40}$N$_3$O$_7$ 590.2866; HPLC purity: 95.88% (C-18 reverse phase, MeOH—H$_2$O, 95:05).

3-Methoxy-6-(3-morpholinopropyl)-2-(3-(pyrrolidin-1-yl)propoxy)-5H-[1,3]dioxolo[4',5':5,6]indeno[1,2-c]isoquinoline-5,12(6H)-dione (28). 1-(3-chloropropyl)piperidine hydrochloride (158 mg, 0.86 mmol) and K$_2$CO$_3$ (237 mg, 1.72 mmol) were added to a DMF (5 mL) solution of compound 18 (0.80 g, 0.172 mmol). The mixture was heated at 90° C. for 19 h. The mixture was diluted to a volume of 300 mL with CHCl$_3$, washed with H$_2$O (2×80 mL) and saturated aq NaCl (80 mL), dried over anhydrous sodium sulfate, and concentrated. The residue was purified by flash column chromatography (SiO$_2$, ~40 g), eluting with a gradient of 0.25% MeOH in CHCl$_3$, to yield the product 28 as a solid (0.051 g, 55%): mp 151-152° C. (dec). IR (film) 3418, 2936, 2119, 1660, 1392, 1225, 1105, 1063 cm$^{-1}$; δ 8.02 (s, 1H), 7.63 (s, 1H), 7.42 (s, 1H), 7.07 (s, 1H), 6.09 (s, 2H), 4.52-4.48 (t, J=8.1 Hz, 2H), 4.29-4.24 (t, J=6.6 Hz, 2H), 3.95 (s, 3H), 3.77-3.74 (t, J=4.5 Hz, 2H), 2.80-2.77 (m, 2H), 2.70 (s, 2H), 2.57-2.53 (m, 6H), 2.25-2.20 (m, 2H), 2.03-1.98 (m, 2H), 1.87 (s, 6H); ESIMS m/z 576 (MH$^+$); HRESIMS m/z 576.2705 (MH$^+$), calcd for C$_{32}$H$_{38}$N$_3$O$_7$ 576.2710; HPLC purity: 96.29% (C-18 reverse phase, MeOH—H$_2$O, 80:20).

Methyl 2-((3-Methoxy-6-(3-morpholinopropyl)-5,12-dioxo-6,12-dihydro-5H-[1,3]dioxolo[4',5':5,6]indeno[1,2-c]isoquinolin-2-yl)oxy)acetate (29). Sodium hydride (0.067 g, 2.8 mmol) and compound 18 (0.130 g, 0.28 mmol) were diluted with DMF (8 mL), and methyl bromoacetate (0.106 ml, 1.12 mmol) was added dropwise. The mixture was stirred at room temperature for 7 h. The mixture was diluted to a volume of 250 mL with CHCl$_3$, washed with H$_2$O (2×60 mL) and saturated aq NaCl (50 mL), dried over anhydrous sodium sulfate, and concentrated. The residue was purified by flash column chromatography (SiO$_2$, ~40 g), eluting with a gradient of 0.5% MeOH in CHCl$_3$, to yield the product 29 as a solid (0.077 g, 51%): mp 226-227° C. IR (film) 2345, 1869, 1749, 1650, 1508, 1031, 737 cm$^{-1}$; $^1$H NMR (CDCl$_3$) δ 7.91 (s, 1H), 7.65 (s, 1H), 7.40 (s, 1H), 7.04 (s, 1H), 6.09 (s, 2H), 4.87 (s, 2H), 4.52-4.47 (t, J=7.2 Hz, 2H), 3.98 (s, 3H), 3.86 (s, 3H), 3.78 (s, 4H), 2.54 (s, 6H), 2.01 (s, 2H); ESIMS m/z 537 (MH$^+$); HRESIMS m/z 537.1875 (MH$^+$), calcd for C$_{28}$H$_{29}$N$_2$O$_9$ 537.1873; HPLC purity: 96.60% (C-18 reverse phase, MeOH—H$_2$O, 90:10).

2-((12-Hydroxy-3-methoxy-6-(3-morpholinopropyl)-5-oxo-6,12-dihydro-5H-[1,3]dioxolo[4',5':5,6]indeno[1,2-c]isoquinolin-2-yl)oxy)acetohydrazide (31). Hydrazine (0.028 ml, 0.056 mmol) and compound 18 (0.015 g, 0.028 mmol) were diluted with EtOH (10 mL), and the mixture was heated at reflux for 16 h. The precipitate obtained was washed with hexane (10 mL) and ether (10 mL) to yield the product 31 as a light yellow solid (0.006 g, 40%): 266-268° C. IR (film) 2365, 1869, 1773, 1648, 1508, 1032, 738 cm$^{-1}$; $^1$H NMR (CDCl$_3$) δ 9.30 (s, 1H), 7.62 (s, 1H), 7.45 (s, 1H), 7.36 (s, 1H), 7.21 (s, 1H), 6.10 (s, 2H), 5.34 (s, 2H), 4.61 (s, 2H), 4.48 (s, 2H), 3.88 (s, 3H), 3.61 (s, 4H), 2.49 (m, 6H), 1.96 (m, 2H); ESIMS m/z 539 (MH$^+$); HRESIMS m/z 539.2146 (MH$^+$), calcd for C$_{27}$H$_{30}$N$_4$O$_8$ 539.2142; HPLC purity: 95.19% (C-18 reverse phase, MeOH—H$_2$O, 85:15).

Method Examples

COMPARE screening. The compounds described herein were examined for antiproliferative activity against the human cancer cell lines in the National Cancer Institute screen (COMPARE screening), in which the activity of each compound was evaluated with approximately 55 different cancer cell lines of diverse tumor origins. The GI50 values (i.e., the concentration causing 50% growth inhibition) obtained with selected cell lines, along with the mean graph midpoint (MGM) values, are summarized in Table 1 and Table 2, and provide a means of comparison of the antiproliferative activity of the compounds described herein with that of other compounds, including camptothecin (S-1), oracin (S-2), and/or 5,6-dihyro-6-(3-amino-1-propyl)-5,11-dioxo-11H-indeno[1,2,c]isoquinoline (S-3). The MGM is based on a calculation of the average GI50 for all of the cell lines tested (approximately 55) in which GI50 values below and above the test range (10$^{-8}$ to 10$^{-4}$ molar) are taken as the minimum (10$^{-8}$ molar) and maximum (10$^{-4}$ molar) drug concentrations used in the screening test. Therefore, the MGM value represents an overall assessment of toxicity of the compound across numerous cell lines. The results of topoisomerase I DNA cleavage experiments are expressed semi-quantitatively and provide a means of comparison with the biological activity of other compounds, including camptothecin (S-1) (++++), oracin (S-2) and/or 5,6-dihyro-6-(3-amino-1-propyl)-5,11-dioxo-11H-indeno[1,2,c]isoquinoline (S-3).

Hollow Fiber Activity. Several of the more active indenoisoquinoline analogs (5p, 5q, 5s, 5v, and 5w) and several of the most active bisindenoisoquinoline analogs (14d, 14g, 14h, and 14i) were evaluated as anticancer agents in an in vivo animal model in which polyvinylidene fluoride (PVDF) "hollow fibers" containing various cancer cell cultures were implanted intraperitoneally (IP) and subcutaneously (SC) into athymic nude mice and compounds were administered by the IP route. The effects of the compounds on the reduction of viable cancer cell mass compared to those of controls were determined. Each compound was tested in the hollow fiber assay against a panel of twelve human tumor cell lines as described previously; see, Hollingshead, M.; Plowman, J.; Alley, M.; Mayo, J.; Sausville, E., The Hollow Fiber Assay. *Contrib. Oncol.* 1999, 54, 109-120; and Plowman, J.; Camalier, R.; Alley, M.; Sausville, E.; Schepartz, S. *Contrib. Oncol.* 1999, 54, 121-135, the disclosures of which are hereby incorporated by reference. The compounds were solubilized in 10% DMSO in saline/Tween-80® and administered intraperitoneally once daily for a total of four doses at each of two dose levels. The two doses were selected based on single dose toxicity studies for each derivative. A score of 2 was assigned each time the compound produced a 50% or greater reduction in viable cell mass compared to vehicle-treated controls. The score for each compound was summed for the intraperitoneal fibers and the subcutaneous fibers to provide the total score for each derivative as shown in Table 3 and Table 4. For comparative purposes, the score for the clinically used anticancer drug paclitaxel is provided.

Induction of DNA cleavage. The compounds described herein may be examined for induction of DNA cleavage in the 3'-end-labeled PvuII/HindIII fragment of pBluescript SK(-) phagemid DNA in the presence of top1 (see, Kohlhagen et al. "Protein-Linked DNA Strand Breaks Induced by NSC 314622, a Novel Noncamptothecin Topoisomerase I Poison," *Mol. Pharmacol.* 1998, 54, 50-58). The cleavage patterns for the compounds described herein can be determined, along with those of comparative compounds NSC 314622 (A) (see, Kohlhagen et al., "Protein-Linked DNA Strand Breaks Induced by NSC 314622, a Novel Noncamptothecin Topoisomerase I Poison," *Mol. Pharmacol.* 1998, 54, 50-58), camptothecin (B, CPT), and NSC 706744 (C, MJ-III-65) (see, Cushman et al., "Synthesis of New Indeno[1,2-c]isoquinolines: Cytotoxic Non-Camptothecin Topoisomerase I Inhibitors," *J. Med. Chem.* 2000, 43, 3688-3698 and Antony et al., "Differential Induction of Topoisomerase I-DNA Cleavage Complexes by the Indenoisoquinoline MJ-III-65 (NSC 706744) and Camptothecin: Base Sequence Analysis and Activity against Camptothecin-Resistant Topoisomerase I," *Cancer Res.* 2003, 63, 7428-7435).

Topoisomerase I-Mediated DNA Cleavage Reactions (A). Using 3'-End-labeled 161 BP Plasmid DNA. The 161 bp fragment from pBluescript SK(-) phagemid DNA (Stratagene, La Jolla, Calif.) is cleaved with the restriction endonuclease Pvu II and Hind III (New England Biolabs, Beverly, Mass.) in supplied NE buffer 2 (10 µL reactions) for 1 h at 37° C., separated by electrophoresis in a 1% agarose gel made in 1× TBE buffer. The 161 bp fragment is eluted from the gel slice (centrilutor by Amicon) and concentrated in a centricon 50 centrifugal concentrator (Amicon, Beverly, Mass.). Approximately 200 ng of the fragment is 3'-end-labeled at the Hind III site by fill-in reaction with [alpha-$^{32}$P]-dCTP and 0.5 mM dATP, dGTP, and dTTP, in React 2 buffer (50 mM Tris-HCl, pH 8.0, 100 mM MgCl, 50 mM NaCl) with 0.5 units of DNA polymerase I (Klenow fragment). Labeling reactions are followed by phenol-chloroform extraction and ethanol precipitation. The resulting 161 bp 3'-endlabeled DNA fragment is resuspended in water. Aliquots (approximately 50,000 dpm/reaction) are incubated with topoisomerase I at 30° C. for 15 mM in the presence the compounds described herein. Reactions are terminated by adding 0.5% SDS. After ethanol precipitation, the samples are resuspended in loading buffer (80% formamide, 10 mM sodium hydroxide, 1 mM sodium EDTA, 0.1% xylene cyanol, and 0.1% bromophenol blue, pH 8.0), and separated in a denaturing gel (16% polyacrylamide, 7 M urea) run at 51° C. The gel is dried and visualized by using a Phosphoimager and ImageQuant software (Molecular Dynamics, Sunnyvale, Calif.).

Topoisomerase II-Mediated DNA Cleavage Assays. Using 5'-End-labeled Human C-myc DNA. A 403-base pair DNA fragment of the human c-myc gene from the junction between the first intron and the first exon is prepared by PCR between positions 2671 and 3073 using the a sense primer oligonucleotide and an antisense primer oligonucleotide, as described by Cushman et al., in U.S. Pat. No. 6,509,344. Single-end labeling of these DNA fragments is obtained by 5'-end labeling of the adequate primer oligonucleotide. Approximately 0.1 µg of the human c-myc DNA that had been restricted by XhoI and XbaI is used as template for PCR. The 5'-end-labeled DNA fragments are equilibrated with or without a drug in 1% dimethyl sulfoxide, 10 mM Tris-HCl, pH 7.5, 50 mM KCl, 5 mM MgCl$_2$, 2 mM dithiothreitol, 0.1 mM Na$_2$EDTA, 1 mM ATP, and 15 µg/mL bovine serum albumin for 5 min before addition of purified human topoisomerase II (40-70 ng) in a 10 µL final reaction volume. The reactions are performed at 37° C. for 30 min and thereafter stopped by adding 1% sodium dodecyl sulfate (SDS) and 0.4 mg/mL proteinase K (final concentrations) followed by an additional incubation at 50° C. for 30 min. Samples are ethanol-precipitated before separation of the topoisomerase II-cleaved fragments on denaturing polyacrylamide gels. The sequencing gels are made of 7% polyacrylamide in 1× TBE buffer (90 mM Tris borate, 2 mM EDTA, pH 8.3). Electrophoresis is performed at 2500 V (60 W) for 2-5 h. The gels were dried and visualized using a Phosphoimager and ImageQuant software.

DNA Cleavage Semiquantitative Analysis. One of the most abundant cleavage products (see, Antony et al., "Differential Induction of Topoisomerase I-DNA Cleavage Complexes by the indenoisoquinoline MJ-III-65 (NSC 706744) and Camptothecin: Base Sequence Analysis and Activity against Camptothecin-Resistant Topoisomerase I," *Cancer Res.* 2003, 63, 7428-7435) is chosen for semiquantitation using ImageQuant TL v2003.3. The rubberband baseline correction is applied with hand detection sensitivity set at 90. In the case of the compounds described herein, the absolute density value for the band corresponding to the above product is compared to the value for the NSC 314622 (A). The ratio of the band density observed for the compounds described herein to the NSC 314622 band is multiplied by 100 to obtain percentages. Assignments are performed as follows: 0-25%, 0; 25-75%, +; 75-175%, ++; 175-325%, +++; camptothecin ++++.

SV40 DNA Unwinding Assay. Reaction mixtures (10 µL final volume) contain 0.3 µg supercoiled SV40 DNA in reaction buffer (10 mM Tris-HCl, pH 7.5, 50 mM KCl, 5 mM MgCl$_2$, 0.1 mM EDTA, 15 µg/mL bovine serum albumin) and 10 units of purified calf thymus topoisomerase I. Reactions are performed at 37° C. for 30 min and terminated by the addition of 0.5% SDS, and then 1.1 µL of 10× loading buffer (20% Ficol 400, 0.1 M Na$_2$EDTA pH 8, 1.0% SDS, 0.25% Bromophenol Blue) is then added and reaction mixtures are loaded onto a 1% agarose gel made in 1× TBE buffer. After electrophoresis, DNA bands are stained in 10 µg/mL of ethidium bromide and visualized by transillumination with UV light (300 nm).

Additional details regarding the biological evaluation of the compounds described herein may be found in co-pending PCT/US2005/008491, the disclosure of which is incorporated herein by reference.

TABLE 1

Cytotoxicities and Topoisomerase I Inhibitory Activities of Indenoisoquinoline Analogs.

| Cmpd | lung HOP-62 | colon HCT-116 | CNS SF-539 | melanoma UACC-62 | ovarian OVCAR-3 | renal SN12C | prostate DU-145 | breast MDA-MB-435 | MGM[b] | Top 1 Cleavage[c] |
|---|---|---|---|---|---|---|---|---|---|---|
| S-1 | 0.01 | 0.03 | 0.01 | 0.01 | 0.22 | 0.02 | 0.01 | 0.04 | .0405 ± 0.0187 | ++++ |
| S-2 | 1.62 | 1.12 | 1.65 | 1.42 | 3.85 | 0.95 | 1.28 | 2.56 | 1.90 ± 80 | + |
| 4a | NT | 100 | 100 | 100 | 100 | 100 | 100 | 100 | 100 | ++ |
| 4b | 53.7 | >100 | >100 | >100 | >100 | >100 | >100 | >100 | 57.5 | ++ |
| 4c | 18.20 | 47.9 | >100 | 25.1 | >100 | >100 | >100 | >100 | 64.6 | 0/+ |
| 4d | >100 | >100 | >100 | >100 | >100 | >100 | >100 | >100 | >100 | 0 |
| 5a | NT | 2.45 | 6.17 | 6.61 | 5.89 | 11.0 | 4.47 | 7.08 | 6.17 | ++ |
| 5b | <0.010 | <0.010 | 2.69 | 0.30 | 2.63 | 0.023 | 2.04 | 3.02 | 0.525 | 0/+ |
| 5c | 5.62 | 6.46 | NT | 7.08 | 25.7 | 4.17 | 5.62 | >100 | 977 | +++ |
| 5d | 1.74 | 0.58 | 1.86 | 0.51 | 1.70 | 0.91 | 1.32 | 2.82 | 1.86 | +++ |
| 5h | 89.1 | 60.3 | >100 | 56.2 | >100 | >100 | >100 | >100 | 741 | +++ |
| 5i | 52.50 | >100 | NT | 83.2 | >100 | 58.9 | 61.7 | >100 | 74.1 | ++++ |
| 5j | >100 | 36.3 | 85.1 | 29.5 | 81.3 | 93.3 | >100 | >100 | 67.6 | ++++ |
| 5e | <0.010 | <0.010 | <0.010 | <0.010 | <0.010 | <0.010 | <0.010 | 0.014 | 0.033 | +++ |
| 5f | 0.19 | 0.274 | 0.016 | 0.012 | 0.864 | 0.015 | 0.017 | 2.17 | 0.370 ± 0.28 | ++++ |
| 5g | 2.69 | 1.41 | 2.34 | 0.79 | 1.66 | 1.66 | 1.41 | 2.75 | 1.86 | +++++ |
| 5l | <0.010 | <0.010 | 0.037 | <0.010 | 0.085 | <0.010 | <0.010 | 0.020 | 0.079 ± 0.023 | ++++ |
| 5m | 0.447 | 1.99 | 0.398 | 0.269 | 56.2 | 0.316 | 0.363 | 7.08 | 2.16 ± 0.24 | ++ |
| 5n | 0.079 | 1.91 | 0.288 | <0.010 | 61.7 | 0.085 | 0.085 | >100 | 3.55 | +++ |
| 5o | <0.010 | <0.010 | <0.010 | 0.014 | 0.041 | <0.010 | <0.010 | <0.010 | 0.112 ± 0.066 | ++++ |
| 5p | <0.005 | 0.575 | <0.005 | 1.20 | 2.04 | 0.091 | 0.015 | 4.57 | 0.382 ± 0.119 | ++ |
| 5q | 1.78 | 1.15 | 0.040 | 0.030 | 74.1 | 0.813 | 0.155 | 67.6 | 4.64 ± 1.25 | ++++ |
| 5r | 26.3 | 72.4 | 18.2 | 37.2 | 34.7 | NT | >100 | >100 | 50.1 | ++ |
| 5s | <0.005 | <0.005 | <0.005 | 5.01 | 5.75 | 0.126 | <0.005 | 0.977 | 0.243 ± 0.088 | +++ |
| 5t | 18.2 | 1.48 | 17.8 | 15.1 | 15.1 | 11.5 | 10.7 | >100 | 12.0 | + |
| 5u | 0.427 | 0.120 | 0.100 | 1.29 | 0.832 | 0.257 | 0.182 | 1.74 | 0.766 ± 0.254 | + |
| 5v | <0.005 | 0.214 | 0.145 | 0.457 | 5.01 | 0.145 | 0.081 | 2.63 | 0.715 ± 0.335 | +++ |
| 5w | 9.77 | 2.34 | 1.44 | 1.23 | 15.1 | >100 | 0.275 | >100 | 7.86 ± 0.27 | ++ |
| 5x | <0.005 | <0.005 | 0.550 | 0.162 | 0.525 | 1.48 | 0.603 | 1.95 | 1.27 ± 0.84 | +++ |
| 5z | 24.5 | >50.1 | 28.2 | >50.1 | >50.1 | >50.1 | >50.1 | >50.1 | 39.8 | 0 |
| 5af | NT | 17.4 | 20.9 | 20.0 | 33.9 | 74.1 | 31.6 | 81.3 | 30.9 | 0 |
| 5ag | 10.7 | 25.7 | 8.71 | 15.5 | — | >50.1 | >50.1 | >50.1 | 19.9 | 0 |
| 5ah | 24.5 | NT | 17.8 | 17.4 | 28.8 | 77.6 | >100 | >100 | 50.1 | — |
| 5ai | 28.8 | 60.3 | 42.7 | 43.6 | >100 | >100 | 97.7 | >100 | 52.5 | 0 |
| 5aj | 20.9 | 35.5 | 29.5 | 24.0 | 70.8 | >100 | 91.2 | >100 | 42.6 ± 5.35 | — |
| 5ak | 32.4 | >100 | 20.4 | 27.5 | >100 | >100 | 91.2 | >100 | 51.3 | — |
| 5al | 0.620 | 0.270 | 0.210 | 0.920 | 0.710 | 0.490 | 0.760 | 0.920 | 0.530 ± 0.320 | +++ |
| 5am | 0.200 | 0.180 | 0.25 | 0.26 | 1.38 | 0.160 | 0.22 | 0.78 | 0.32 ± 0.23 | +++ |
| 5an | 0.08 | 0.10 | 0.10 | 0.05 | 0.52 | 0.04 | 0.01 | 0.84 | 0.16 ± 0.01 | +++ |
| 5ao | 0.288 | 0.200 | 0.871 | 1.35 | 0.708 | 0.398 | 0.347 | 1.35 | 0.471 ± 0.054 | 0 |
| 5ap | 1.29 | 0.912 | 1.23 | 1.62 | 2.00 | 1.32 | 0.603 | 2.04 | 1.32 | ++ |
| 5aq | 1.20 | 1.26 | 1.78 | 2.00 | 1.70 | 1.66 | 0.832 | 2.24 | 1.66 ± 0.155 | 0 |
| 5ar | 2.14 | 1.66 | 2.82 | 3.80 | 3.47 | 3.47 | 3.39 | 5.62 | 3.71 | + |
| 5as | 6.76 | 6.46 | 9.77 | 9.33 | 9.55 | 8.51 | 6.03 | 9.55 | 8.13 | 0 |
| 5at | 4.79 | 2.75 | 1.82 | 13.8 | 10.7 | 3.31 | 3.47 | 11.7 | 5.50 | 0 |
| 5au | 2.19 | 1.91 | 2.04 | 1.70 | 2.00 | 2.00 | 4.57 | 11.0 | 5.13 | + |
| 5av | 17.0 | NT | 18.2 | 14.8 | 17.8 | 13.5 | 19.1 | 19.5 | 18.2 | 0/+ |
| 5aw | 11.2 | NT | 12.3 | 10.7 | 13.8 | 28.2 | 13.5 | 3.09 | 15.1 | 0 |
| 5ax | 7.59 | NT | 6.76 | 8.71 | 13.8 | 13.8 | 13.8 | 42.7 | 11.5 | +++ |
| 5ay | 21.4 | NT | 17.4 | 27.5 | >100 | 77.6 | 74.1 | 5.13 | 53.7 | 0 |
| 5az | 28.8 | NT | 27.5 | 89.1 | >100 | >100 | 81.3 | 4.57 | 44.7 | 0 |
| 5ba | 0.295 | 0.794 | 0.027 | <0.010 | 3.39 | <0.010 | 0.036 | 3.24 | 0.178 ± 0.012 | ++++ |
| 5bb | NT | 3.47 | >100 | >100 | >100 | >100 | >100 | >100 | 40.0 | 0 |
| 5bc | NT | NT | NT | NT | NT | NT | NT | NT | NT | +++ |
| 5bd | NT | 0.046 | 0.058 | 0.148 | 3.02 | 0.309 | 0.034 | 1.48 | 0.328 ± 0.046 | ++++ |
| 5bf | 33.9 | 26.9 | 44.7 | 75.9 | 52.5 | >100 | 61.7 | 64.6 | 38.9 | +++ |
| 5bg | <0.010 | <0.010 | 0.038 | NT | 0.028 | <0.010 | 0.014 | 0.059 | 0.048 ± 0.024 | + |
| 5bh | 7.59 | 4.90 | NT | 19.5 | 7.94 | 25.1 | 29.5 | 7.76 | 12.3 | 0 |
| 5bi | 0.021 | 0.038 | 0.095 | 0.380 | NT | 0.309 | 0.085 | 1.23 | 0.632 ± 0.029 | +++ |
| 5bj | <0.010 | <0.010 | NT | <0.010 | <0.010 | <0.010 | NT | <0.010 | 0.014 ± 0.001 | NA |
| 5bk | 1.41 | 1.26 | 1.95 | 1.58 | 2.69 | 4.07 | 2.29 | 4.68 | 2.70 ± 0.125 | + |
| 5bl | 0.031 | 0.027 | >100 | 0.200 | 1.35 | 0.229 | >100 | 1.07 | 0.296 ± 0.067 | NA |
| 5bm | <0.010 | NT | <0.010 | <0.010 | <0.010 | 0.012 | <0.010 | <0.010 | 0.016 | ++++ |
| 5bn | 0.026 | 0.044 | 0.112 | 0.550 | 0.417 | 0.158 | 0.055 | 0.389 | 0.124 ± 0.014 | 0 |
| 5bo | 0.195 | NT | 0.550 | 0.178 | 0.550 | 0.269 | 0.174 | 0.490 | 0.339 | NA |
| 5bp | <0.010 | <0.010 | <0.010 | <0.010 | 0.028 | <0.010 | <0.010 | <0.010 | 0.020 ± 0.001 | NA |
| 5bq | 0.078 | 0.102 | 0.240 | 1.00 | 0.427 | 0.245 | 0.257 | 0.617 | 0.300 ± 0.072 | 0 |

TABLE 1-continued

Cytotoxicities and Topoisomerase I Inhibitory Activities of Indenoisoquinoline Analogs.

| | cytotoxicity (GI50 in μM)[a] | | | | | | | | | |
|---|---|---|---|---|---|---|---|---|---|---|
| Cmpd | lung HOP-62 | colon HCT-116 | CNS SF-539 | melanoma UACC-62 | ovarian OVCAR-3 | renal SN12C | prostate DU-145 | breast MDA-MB-435 | MGM[b] | Top 1 Cleavage[c] |
| 5br | <0.010 | <0.010 | <0.010 | <0.010 | 0.020 | <0.010 | <0.010 | <0.010 | 0.019 ± 0.004 | NA |
| 5bs | 0.056 | 0.110 | 0.178 | 0.071 | 1.66 | 0.676 | 0.204 | 0.646 | 0.416 ± 0.134 | +++ |

[a]The cytotoxicity GI50 values are the concentrations corresponding to 50% growth inhibition.
[b]Mean graph midpoint for growth inhibition of all human cancer cell lines successfully tested.
[c]The compounds were tested at concentrations ranging up to 10 μM.
The activity of the compounds to produce top 1-mediated DNA cleavage was expressed semiquantitatively as follows:
+: weak activity;
++ and +++: modest activity;
++++: similar activity as 1 μM camptothecin;
+++++: greater activity than 1 μM camptothecin.
NT: Not Tested;
NA: Not Available
S-1 = camptothecin
S-2 = oracin

TABLE 2

Cytotoxicities and Topoisomerase I Inhibitory Activities of Bis-Indenoisoquinoline Analogs.

| | cytotoxicity (GI50 in μM)[a] | | | | | | | | | |
|---|---|---|---|---|---|---|---|---|---|---|
| Cmpd | lung HOP-62 | colon HCT-116 | CNS SF-539 | melanoma UACC-62 | ovarian OVCAR-3 | renal SN12C | prostate DU-145 | breast MDA-MB-435 | MGM[b] | Top 1 Cleavage[c] |
| S-3 | 0.20 | 0.18 | 0.25 | 0.26 | 1.38 | 0.16 | 0.22 | 0.78 | 0.32 ± 0.23 | +++ |
| S-1 | 0.01 | 0.03 | 0.01 | 0.01 | 0.22 | 0.02 | 0.01 | 0.04 | .0405 ± 0.0187 | ++++ |
| 12a | >25.1 | >25.1 | >25.1 | >25.1 | >25.1 | >25.1 | >25.1 | >25.1 | 18.2 | + |
| 12c | 0.794 | 0.550 | 3.63 | 6.61 | 2.95 | 1.55 | 1.00 | 8.91 | 4.28 ± 1.89 | + |
| 12d | NT | NT | 1.12 | 2.00 | 1.20 | 0.589 | NT | 1.55 | 0.934 ± 0.476 | ++ |
| 13a | 22.4 | 22.9 | >50.1 | >50.1 | 21.4 | >50.1 | >50.1 | >50.1 | 33.9 | 0 |
| 13b | 20.0 | 14.1 | >50.1 | 45.7 | 13.2 | 39.8 | >50.1 | >50.1 | 28.2 | 0 |
| 13d | 11.0 | 1.91 | 8.13 | 93.3 | 69.2 | 36.3 | 47.9 | 69.2 | 35.5 | ++ |
| 14a | 0.977 | 1.05 | 14.5 | 5.01 | 8.91 | 11.0 | 1.91 | 2.24 | 5.25 | + |
| 14b | 0.028 | 0.056 | NT | 0.513 | 0.372 | 0.132 | 0.288 | 0.562 | 0.357 ± 0.087 | + |
| 14c | 0.032 | 0.029 | NT | 0.331 | 1.66 | 0.178 | 0.182 | 1.66 | 0.427 ± 0.01 | + |
| 14d | 0.339 | <0.005 | 0.155 | 0.182 | 0.093 | <0.005 | 0.079 | 0.024 | 0.122 ± 0.064 | ++++ |
| 14e | <0.010 | <0.010 | NT | 0.052 | 1.02 | <0.010 | <0.010 | 0.933 | 0.152 ± 0.062 | ++++ |
| 14f | 12.9 | 35.5 | >100 | >100 | >100 | 15.5 | 24.0 | >100 | 44.8 ± 2.05 | 0 |
| 14g | <0.010 | <0.010 | 0.011 | 0.042 | 0.074 | <0.010 | NT | 0.107 | 0.394 ± 0.33 | ++++ |
| 14h | 0.525 | <0.005 | 0.251 | 0.562 | 0.135 | <0.005 | 0.234 | 0.676 | 0.225 ± 0.084 | +++ |
| 14i | 0.048 | 0.112 | 0.275 | 0.269 | 1.15 | 0.017 | 0.331 | 1.00 | 0.474 ± 0.143 | +++ |
| 14j | 0.977 | 0.200 | 0.012 | NT | 0.032 | NT | 0.085 | 0.126 | 0.262 ± 0.100 | ++ |
| 14k | 0.068 | 0.045 | 0.170 | 1.23 | 0.269 | 0.028 | 0.209 | 0.813 | 0.562 | ++ |
| 14l | 1.51 | 0.331 | 4.17 | 4.27 | 9.55 | 0.240 | 19.5 | 3.98 | 6.03 | ++ |
| 14m | 0.631 | 0.044 | 0.324 | 0.603 | 0.245 | 0.123 | 0.813 | 0.437 | 0.354 ± 0.184 | ++ |
| 14n | 3.02 | 1.45 | 1.17 | 1.78 | 2.29 | 1.17 | 0.912 | 3.89 | 1.50 ± 0.24 | 0 |
| A[d] | NT | 43 | >100 | 44 | 0.88 | 33 | >100 | 68 | 58.9 | ++ |
| 16a | >100 | >100 | NT | >100 | NT | >100 | NT | >100 | 68.0 | 0 |
| 17a | 0.191 | 0.022 | <0.010 | NT | <0.010 | NT | <0.010 | 0.155 | 0.046 ± 0.010 | + |

[a]The cytotoxicity GI50 values are the concentrations corresponding to 50% growth inhibition.
[b]Mean graph midpoint for growth inhibition of all human cancer cell lines successfully tested.
[c]The compounds were tested at concentrations ranging up to 10 μM.
The activity of the compounds to produce top1-mediated DNA cleavage was expressed semi-quantitatively as follows:
+ & ++: weak activity;
+++: similar activity as compound S-3;
++++: similar activity as 1 μM camptothecin;
NT: Not Tested.
S-1 = camptothecin;
S-3 = 5,6-dihydro-6-(3-amino-1-propyl)-5,11-dioxo-11 H-indeno[1,2,c]isoquinoline (NSC 725671).
[d]A = 5,6-dihydro-2,3-dimethoxy-8,9-methylenedioxy-6-(3-aminopropylaminopropylamino-1-propyl)-5,11-dioxo-11H-indeno[1,2-c]isoquinoline

TABLE 3

Hollow Fiber Activities of Indenoisoquinoline Analogs.

| Compound | IP Score[a] | SC score[a] | Total score | Cell kill[b] | Compound | IP Score[a] | SC score[a] | Total score | Cell kill[b] |
|---|---|---|---|---|---|---|---|---|---|
| 5p | 16 | 2 | 18 | N | 5s | 6 | 0 | 6 | N |
| 5q | 4 | 2 | 6 | N | 5v | 12 | 2 | 14 | N |

TABLE 3-continued

Hollow Fiber Activities of Indenoisoquinoline Analogs.

| Compound | IP Score[a] | SC score[a] | Total score | Cell kill[b] |
|---|---|---|---|---|
| 5w | 8 | 0 | 8 | N |
| Paclitaxel | 24 | 8 | 32 | Y |

[a]The IP and SC scores listed are the sums of all the IP and SC scores for each compound.
[b]A net cell kill at one or more implant sites is indicated with a Y.

TABLE 4

Hollow Fiber Activities of Bis-Indenoisoquinoline Analogs.

| Compound | IP Score[a] | SC score[a] | Total score | Cell kill[b] |
|---|---|---|---|---|
| 14d | 2 | 4 | 6 | N |
| 14g | 26 | 6 | 32 | N |
| 14h | 12 | 4 | 16 | N |
| 14i | 10 | 6 | 16 | N |
| Paclitaxel | 24 | 8 | 32 | Y |

[a]The IP and SC scores listed are the sums of all the IP and SC scores for each compound.
[b]A net cell kill at one or more implant sites is indicated with a Y.

Topoisomerase I-Mediated DNA Cleavage Reactions (B).

Human recombinant Top1 was purified from baculovirus as described in Bailly, C. *Curr. Med. Chem.* 2000, 7, 39-58. DNA cleavage reactions were prepared as previously reported with the exception of the DNA substrate in Saltz, et al. *Oncologist* 1997, 2, 402-409. Briefly, a 117-bp DNA oligonucleotide (Integrated DNA Technologies) encompassing the previously identified Top1 cleavage sites in the 161-bp fragment from pBluescript SK(−) phagemid DNA was employed. This 117-bp oligonucleotide contains a single 5'-cytosine overhang, which was 3'-end-labeled by fill-in reaction with [α-$^{32}$P]dGTP in React 2 buffer (50 mM Tris-HCl, pH 8.0, 100 mM $MgCl_2$, 50 mM NaCl) and 0.5 unit of DNA polymerase I (Klenow fragment, New England BioLabs). Unincorporated [$^{32}$P]dGTP was removed using mini Quick Spin DNA columns (Roche, Indianapolis, Ind.), and the eluate containing the 3'-end-labeled DNA substrate was collected. Approximately 2 nM radiolabeled DNA substrate was incubated with recombinant Top1 in 20 µL of reaction buffer [10 mM Tris-HCl (pH 7.5), 50 mM KCl, 5 mM $MgCl_2$, 0.1 mM EDTA, and 15 µg/mL BSA] at 25° C. for 20 min in the presence of various concentrations of compounds. The reactions were terminated by adding SDS (0.5% final concentration) followed by the addition of two volumes of loading dye (80% formamide, 10 mM sodium hydroxide, 1 mM sodium EDTA, 0.1% xylene cyanol, and 0.1% bromphenol blue). Aliquots of each reaction mixture were subjected to 20% denaturing PAGE. Gels were dried and visualized using a phosphoimager and ImageQuant software (Molecular Dynamics). For simplicity, cleavage sites were numbered as previously described in the 161-bp fragment.

Gel-Based Assay Measuring the Inhibition of Recombinant TDP1.

A 5'-[$^{32}$P]-labeled single-stranded DNA oligonucleotide containing a 3'-phosphotyrosine (N14Y) was generated as described by Dexheimer et al. (*J. Med. Chem.* 2009, 52, 7122-7131). The DNA substrate was then incubated with 5 pM recombinant TDP1 in the absence or presence of inhibitor for 15 min at room temperature in a buffer containing 50 mM Tris HCl, pH 7.5, 80 mM KCl, 2 mM EDTA, 1 mM DTT, 40 µg/ml BSA and 0.01% Tween-20. Reactions were terminated by the addition of 1 volume of gel loading buffer [99.5% (v/v) formamide, 5 mM EDTA, 0.01% (w/v) xylene cyanol, and 0.01% (w/v) bromophenol blue]. Samples were subjected to a 16% denaturing PAGE and gels were exposed after drying to a PhosphorImager screen (GE Healthcare). Gel images were scanned using a Typhoon 8600 (GE Healthcare) and densitometric analyses were performed using the ImageQuant software (GE Healthcare).

Molecular Modeling.

The Top1 crystal structure for docking was prepared, and the docking protocol was validated as previously described (Nagarajan, M. et al. *J. Med. Chem.* 2003, 46, 5712-5724). The ternary complex ligand centroid coordinates for docking were defined using the ligand in the Top1-DNA-MJ238 crystal structure (PDB code 1SC7) as the center of the binding pocket (x=21.3419, y=−3.9888, z=28.2163). The ligand was then deleted. Indenoisoquinolines to be modeled were constructed in SYBYL. Atom types were assigned using SYBYL atom typing. Hydrogens were added, and the ligands were minimized by conjugate gradient method using the MMFF94s force field with MMFF94 charges, a distance dependent dielectric function, and a 0.01 kcal mol$^{-1}$ Å$^{-1}$ energy gradient convergence criterion. Each ligand was docked into the mutant crystal structure using GOLD 3.2 with default parameters, and the coordinates were defined by the crystal structure as described above. The top four poses for each ligand were examined. The highest-ranked poses for these ligands were merged into the crystal structure, and the entire complex was subsequently subjected to minimization using a standard Powell method, the MMFF94s force field and MMFF94 charges, a distance-dependent dielectric function, and a 0.05 kcal mol$^{-1}$ Å$^{-1}$ energy gradient convergence criterion. During the energy minimization, the ligand and a 7 Å sphere surrounding the ligands were allowed to move while the structures outside this sphere were frozen in an aggregate.

The TDP1 crystal structure (PDB: 1REF) was prepared by removing one of the monomers along with all crystallized waters, the polydeoxyribonucleotide 5'-D-(*AP*GP*TP*T)-3', the Top1-derived peptide residues 720-727 (mutation L724Y), and all metal ions. The Lys265, Lys495, and His493 residues were protonated. Missing hydrogens were added as needed. GOLD docking was performed using the centroid x=7.194, y=52.407, z=0.704. The hydrogen bond length was set to 4 Å, while the van der Waals parameter was set to 10 Å. The top ligand-binding pose (highest GOLD score) was selected and merged with the prepared protein. The ligand was surrounded by a sphere with a 12 Å radius and energy minimized by the conjugate gradient method using the MMFF94s force field and MMFF94 charges with Sybyl software. The calculation was terminated when the gradient reached a value of 0.05 kcal/(mol·Å).

Molecular Docking Study Example

A molecular docking study was performed to guide the structural modification of the indenoisoquinolines and to help understand the Top1 inhibition results. The energy-minimized structure of the morpholine derivative 18 (Scheme 8) was docked into the crystal structure (PDB 1SC7) of a Top1-DNA cleavage site with GOLD using the centroid coordinates of the indenoisoquinoline ligand. The energy-minimized, top-ranked GOLD pose of compound 18 in ternary complex with DNA and Top1 is displayed in FIG. 1. Compound 18 intercalates readily at the DNA cleavage site, between the +1 and −1 base pairs. Rings A and B stack with the scissile strand bases, while rings C and D stack with the noncleaved strand bases. The carbonyl group on the C-ring forms a hydrogen bond to a nitrogen of the Arg364 side chain with an N—O distance of 2.5 Å, which is an essential contact for the Top1 inhibitory activity. It is worth mentioning that Asp533 is also an important residue known to be required for enzyme sensitivity to camptothecin. The X-ray crystal structure of the ternary campthothecin-Top1-DNA complex indicates that camptothecin intercalates at the site of DNA cleavage and forms two hydrogen bonds with the active site. One hydrogen bond in the camptothecin ternary complex is from a nitrogen atom of Arg364 to a free electron pair of the B-ring N1 of camptothecin (N—N distance 2.9 Å); the other interaction is a hydrogen bond between C20 hydroxyl and the oxygen atom of Asp533 (O—O distance 3.4 Å). In the present molecular docking study (FIG. 1), the calculated distance between the 2-position oxygen atom of compound 18 and the carbonyl group of Asp533 is 4.7 Å. The docking pose suggests that aminoalkyl substituents attached to O-2, next to the cleaved DNA strand, could be used to target the carboxylate of Asp533. Therefore, a series of O-2 indenoisoquinoline derivatives were designed and synthesized with 2-OH indenoisoquinoline 18 as the starting material.

Top1-Mediated DNA Cleavage Assays Examples

All of the new indenoisoquinoline derivatives with C-2 side chains were tested in Top1-mediated DNA cleavage assays. For this purpose, a $^{32}$P 3'-end labeled 117-bp DNA fragment was incubated with Top1 and four 10-fold dilutions starting from 100 μM of a tested compound. The DNA fragments were separated on 20% PAGE denaturing gels. The Top1 inhibitory activities were assigned on the basis of the visual inspection of the number and intensities of the gel bands corresponding to Top1-mediated DNA cleavage fragments. The results of this assay are designated relative to the Top1 inhibitory activity of compounds 32 and 33, and expressed in semiquantitative fashion: 0, no detectable activity; +, weak activity; ++, similar activity to compound 33; +++, greater activity than 33; ++++, equipotent to 32. Ambiguous scores (e.g., between two values) are designated with parentheses (e.g., ++(+) would be between ++ and +++).

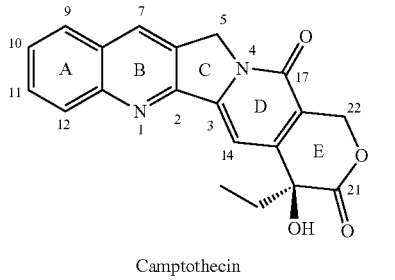

Camptothecin

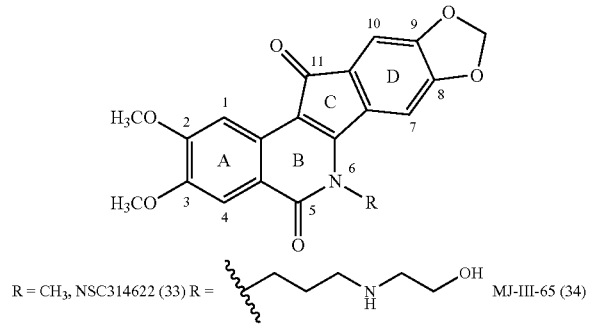

Figure 2:
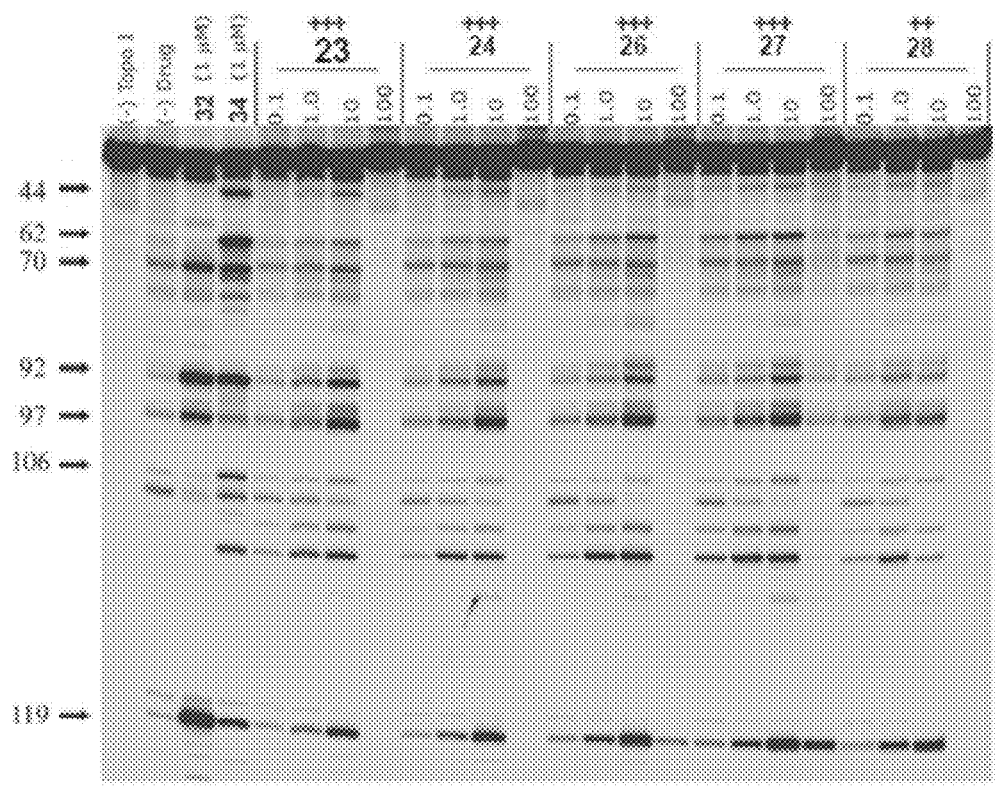
FIG. 2 depicts a Top1-mediated DNA cleavage induced by indenoisoquinolines 23, 24 and 26-28: lane 1, DNA alone; lane 2, Top1+DNA; lane 3, 32, 1 µM; lane 4, 34, 1 µM; lanes 5-24, 23, 24, 26, 27, and 28 at 0.1, 1, 10, and 100 µM, respectively, from left to right. Numbers and arrows on the left indicate cleavage site positions.

As shown in Table 5, compound 22, which has an aminopropyl side chain, expressed low Top1 inhibitory activity at the 0/+ level. Interestingly, after conversion of the primary amine to a dimethyamine, the observed Top1 inhibitory activity increased from 0/+ for 22 to +++ for 23. A similar change was observed with the ethylaminopropyl compound 24, which displayed improved Top1 inhibitory activity relative to 22 at the +++ level. Introduction of a morpholine at the end of the propyl chain yielded compound 25, which was also found to be a promising Top1 inhibitor with activity at the +++ level. Subsequently, N-methylpiperazine, piperidine, and pyrrolidine were also introduced to the end of the propyl chain, and the corresponding compounds 26, 27 and 28 displayed good Top1 inhibitory activity at the +++, +++, and ++ levels, respectively. Compounds 20, 29, and 31, which lack aminopropyl side chain structures, were in general found to be more moderate Top1 inhibitors with + or ++ activity. The Top1 inhibitory activity of the primary amine 22 is low, but the activity was improved after conversion of the primary amine to a dimethylamine or to other cyclic amines. The extra steric bulk around the nitrogen may help position the protonated nitrogen for binding to the Asp533 carboxylate. The Top1-mediated DNA fragmentation patterns produced by camptothecin, indenoisoquinoline 34, and compounds 23-28 are presented in FIG. 2. The sequence preferences for trapping the Top1-DNA cleavage complexes by these indenoisoquinolines are similar to each other, but the pattern is different from camptothecin, indicating that the indenoisoquinolines target the genome differently from camptothecin. Interestingly, as is evident from the gel, these indenoisoquinolines suppress DNA cleavage at a high concentration of 100 μM.

Figure 3:
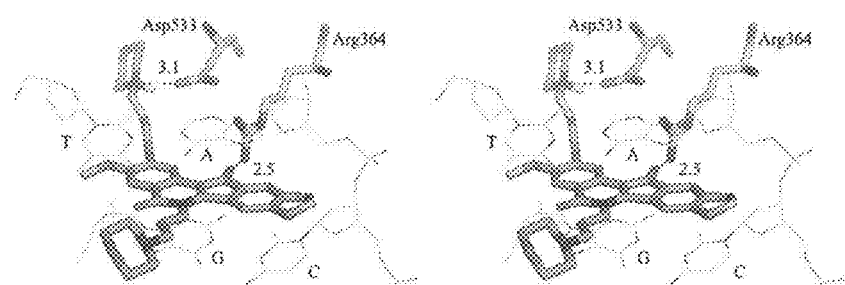
FIG. 3 depicts a hypothetical binding mode of compound 25 in ternary complex with DNA and Top1. All distances are measured from heavy atom to heavy atom. The diagram is programmed for wall-eyed (relaxed) viewing. Compound 25 is shown in sticks, and the base pairs are displayed in lines.

According to the DNA unwinding studies (Kiselev, et al. *J. Med. Chem.* 2011, 54, 6106-6116), this result can be attributed to the ability of these indenoisoquinolines to intercalate into free DNA at high drug concentrations, thus suppressing DNA cleavage by Top1 by making the DNA a poorer Top1 substrate. To rationalize the effect of the introduction of aminopropyl side chains on the O-2 position of indenoisoquinolines on their ability to improve the Top1 inhibitory activity, compound 25 was selected for a molecular docking study. As shown in FIG. 3, compound 25 hypothetically intercalates at the site of DNA cleavage, between the +1 and −1 base pairs. Rings A and B stack with the scissile strand bases, while rings C and D stack with the noncleaved strand bases, which is consistent with the calculated binding mode of compound 18. The carbonyl group on the C-ring the minor DNA groove forms a hydrogen bond with a nitrogen of the Arg364 side chain with an O—N distance of 2.5 Å, and as expected, there is also a hydrogen bond between the N atom in the morpholine ring in the major DNA groove and the Asp533 side chain with a distance of 3.1 Å, which may contribute to the slightly improved Top1 inhibitory activity of these O-2-modified indenoisoquinolines relative to the phenol 18.

TABLE 5

Top1 and TDP1 Activity of O-2-Modified Indenoisoquinolines

| Compd | Top1[a] | TDP1[b] |
|---|---|---|
| 18 | ++(+) | NT |
| 20 | + | 0 |
| 22 | 0/+ | + |
| 23 | +++ | ++ |
| 24 | +++ | ++ |
| 25 | +++ | 0 |
| 26 | +++ | 0 |
| 27 | +++ | ++ |
| 28 | ++ | ++(+) |

TABLE 5-continued

Top1 and TDP1 Activity of O-2-Modified Indenoisoquinolines

| Compd | Top1[a] | TDP1[b] |
|---|---|---|
| 29 | ++ | 0 |
| 31 | + | 0 |

[a]Compound-induced DNA cleavage due to Top1 inhibition is graded by the following semiquantitative scale relative to 1 μM camptothecin (32) or MJ-III-65 (34): 0, no detectable activity; +, weak activity; ++, similar activity to compound 5; +++, greater activity than 34; ++++, equipotent to 32. The (+) ranking indicates the activity lies between two given values. NT: not tested.
[b]TDP1 IC$_{50}$ was determined in duplicate using a semiquantitative scale: 0, IC$_{50}$>111 μM; +, IC$_{50}$ between 37 and 111 μM; ++, IC$_{50}$ between 12 and 37 μM; +++, IC$_{50}$ between 1 and 12 μM; ++++, IC$_{50}$<1 μM.

TDP1 Inhibitory Activities.

Figure 4:
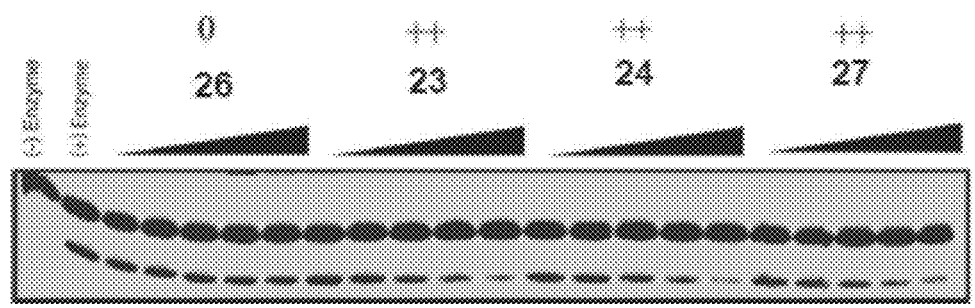
FIG. 4 depicts representative gels showing concentration-dependent TDP1 inhibition by O-2 modified indenoisoquinolines 26, 23, 24, and 27: lane 1, DNA alone; lane 2, TDP1+ DNA; lanes 3-22, 21, 23, 24, and 27 at 1.4, 4.1, 12.3, 37, and 111 µM, respectively, from left to right.

The TDP1 inhibitory activities of the O-2-substituented indenoisoquinolines were measured by determining their abilities to inhibit the hydrolysis of the phosphodiester linkage between tyrosine and the 3'-end of a DNA oligonucleotide substrate and thus prevent the generation of an oligonucleotide with a free 3'-phosphate (N14P, Scheme 12). Therefore, the disappearance of the gel band for N14P indicates TDP1 inhibition. The TDP1 inhibitory activities of O-2-modified indenoisoquinolines are displayed in Table 5, and a representative gel demonstrating dose-dependent TDP1 inhibition is depicted in FIG. 4. TDP1 IC$_{50}$ was determined in duplicate using a semiquantitative scale: 0, IC$_{50}$>111 μM; +, IC$_{50}$ between 37 and 111 μM; ++, IC$_{50}$ between 12 and 37 μM; +++, IC$_{50}$ between 1 and 12 μM, ++++; IC$_{50}$<1 μM.

From Table 5 and FIG. 4, it is clear that compounds 23 and 24, which have dimethyamine or ethylamine at the end of the propyl side chain, display good TDP1 inhibitory activity with ++ potency. Compounds 27 and 28, with six- or five-membered rings on the end of the propyl side chain, also exhibit good inhibition of TDP1 with ++ and ++(+) activity, respectively. However, when the 4-position of the six-membered ring was substituted with heteroatom (oxygen for compound 25, nitrogen for compound 26), no TDP1 inhibitory activity was observed. The structure-activity relationships correlate well with the molecular docking studies. According to the previous report on TDP1 (Dexheimer, et al. *Anti-Cancer Agents Med. Chem.* 2008, 8, 381-389), two specific regions of the enzyme are important for substrate binding, which have been termed the catalytic region and the hydrophobic region. The TDP1 catalytic region possesses two lysine (265 and 495) and two histidine (263 and 493) residues, which are responsible for the stabilization of the negatively charged phosphate backbone of the DNA, while the hydrophobic region consists of several residues (Ala520, Ala456, Phe259, Met491, Gly260, Tyr261, etc.) located at the top of the substrate channel. Compound 27, which has a propyl side chain attached at the terminal end to a piperidine, was docked into the active site of the TDP1 crystal structure (PDB ID: 1RFF) using GOLD.

Figure 5:
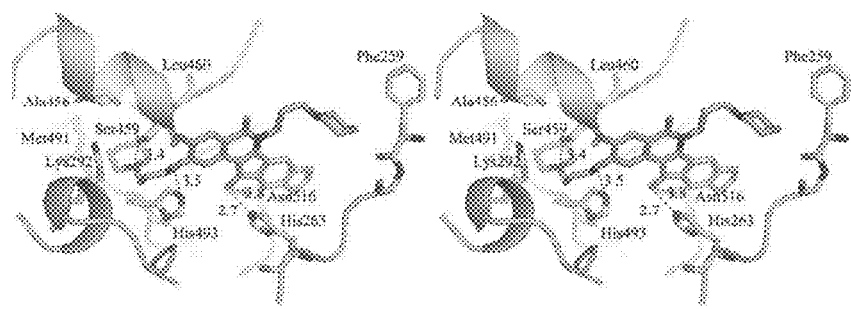
FIG. 5 depicts a hypothetical binding mode of compound 27 in the active site of TDP1 (PDB ID: 1RFF). All distances are measured from heavy atom to heavy atom. The diagram is programmed for wall-eyed (relaxed) viewing. Compound 27 is shown in sticks.

The energy-minimized, top-ranked GOLD pose of compound 27 in the TDP1 active site is displayed in FIG. 5. Compound 27 fits well in the catalytic and hydrophobic regions with four hydrogen bonds. The 2-ether oxygen on the A ring and the 11-carbonyl group on the C ring of compound 27 are calculated to form hydrogen bonds with the catalytic histidine residues 493 and 263, respectively. There are also hypothetical hydrogen bonds calculated between the 11-carbonyl group on the C ring and Asn516, as well as between N atom of the piperidine in the side chain and Ser459. The propyl side chain ending with piperidine in compound 27 occupies the hydrophobic region as expected, which provides a reason for the greater TDP1 activity of compounds with three-carbon side chains connected to amines with more hydrophobic substituents. For example, compounds 23 and 24, which have dimethyamino and ethylamino groups on the end of the propyl side chain, exhibit excellent TDP1 activity, and compounds 27 and 28, with piperidine and pyrrolidine on the end of the propyl side chain, also show promising TDP1 activity. In contrast, compounds 25 and 26, which have the less hydrophobic amines N-methylpiperazine and morpholine, display no TDP1 inhibitory activity.

Accordingly, molecular docking studies indicate that the indenoisoquinoline platform present in Top1 inhibitors could be accommodated within the catalytic region in the TDP1 active site, and a three-carbon side chain at O-2 containing terminal amines bearing hydrophobic substituents could bind in a hydrophobic region of TDP1. This approach was validated by enzyme inhibition assays that demonstrated significant inhibition of both enzymes by compounds 23, 24, 27, and 28.

Scheme 12. Schematic representation of the TDP1 gel-based assays using recombinant TDP1

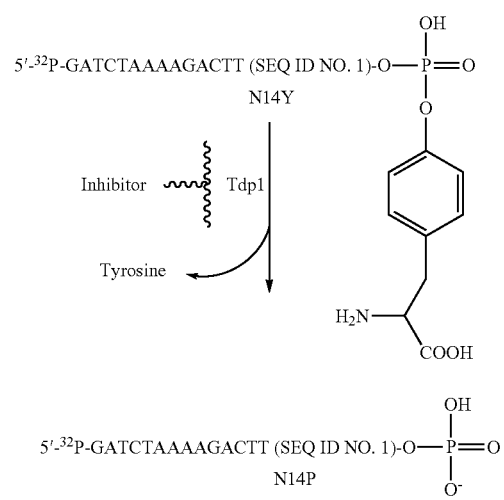

Antiproliferative Activity Tests.

Selected compounds were tested for antiproliferative activity in the National Cancer Institute's developmental therapeutics assay 60 cell line screen (NCI60). The cells were incubated with the tested compounds at 100, 10, 1, 0.1, and 0.01 μM concentrations for 48 h before treatment with sulforhodamine B dye. Optical densities were recorded, and their ratios relative to that of the control were plotted as percentage growth against the log 10 of the tested compound concentrations. The concentration that corresponds to 50% growth inhibition (GI$_{50}$) is calculated by interpolation between the points located above and below the 50% percentage growth. The results are listed in Table 6.

Many of the new O-2-modified indenoisoquinolines display significant potencies against various cell lines with $GI_{50}$'s in the low micromolar (compounds 27 and 29) or submicromolar range (compounds 20, 22, and 25). Compounds 25, 27 and 28, which have potent inhibitory against Top1, also have cytotoxicities with mean graph midpoint (MGM) values ranging from $1.575\pm0.233$ to $0.24\pm0.028$ μM. Although the MGM values for compounds 20, 22, 25, 27, 28 and 29 do not differ greatly, in general there is an intriguing lack of correlation between the rank order of observed cytotoxicities and inhibition of the two enzymes studied. For example, the indenoisoquinoline 20 is the most cytotoxic compound, but it has low Top1 inhibitory activity and no detectable TDP1 inhibitory activity. On the other hand, the cytotoxicity of 27 is comparatively low, but it has relatively high activity vs. both enzymes. The $GI_{50}$ values in individual cell lines vary more widely than the MGM values and more significant differences are observed. For example, compound 29 is the most cytotoxic of the indenoisoquinolines vs. the lung HOP-62 cell line, but it has the lowest overall cytotoxicity as indicated by the MGM value. Therefore, the lack of a strong correlation between enzyme inhibition and cytotoxicity is a complicated matter that may be influenced by the particular cell line under investigation, as well as differences in cellular penetration, distribution within the cell, metabolism, ejection from the cell, and possible off-target effects.

TABLE 6

Antiproliferative Potencies of Selected O-2-Modified Indenolsoquinolines.

| | Cytotoxicity ($GI_{50}$ in μM)[a] | | | | | | | | |
|---|---|---|---|---|---|---|---|---|---|
| Compd | lung HOP-62 | Colon HCT-116 | CNS SF-539 | melanoma UACC-62 | Ovarian OVCAR-3 | renal SN12C | prostate DU-145 | breast MCF-7 | MGM[b] |
| 32 | 0.01 | 0.03 | 0.01 | 0.01 | 0.22 | 0.02 | 0.01 | 0.01 | $0.04 \pm 0.018$[c] |
| 33 | 1.3 | 35 | 41 | 4.2 | 73 | 68 | 37 | 1.58 | $20.0 \pm 14$ |
| 34 | 0.02 | 0.10 | 0.04 | 0.03 | 0.5 | <0.01 | <0.01 | <0.01 | $0.2 \pm 0.19$ |
| 18 | 0.3 | 0.39 | 0.3 | 0.3 | 0.9 | 0.2 | 0.3 | 0.1 | $0.4 \pm 0.005$ |
| 20 | <0.01 | 0.01 | 0.01 | <0.01 | 0.3 | <0.01 | <0.01 | <0.01 | $0.1 \pm 0.035$ |
| 22 | 0.3 | 0.2 | 0.2 | 0.3 | 0.4 | 0.3 | 0.3 | 0.2 | $0.5 \pm 0.092$ |
| 25 | 0.03 | 0.1 | 0.1 | 0.2 | 0.7 | 0.1 | 0.02 | 0.02 | $0.2 \pm 0.028$ |
| 27 | 0.3 | 1.1 | 0.03 | 9.6 | 5.4 | 0.4 | 0.2 | 0.04 | $1.6 \pm 0.23$ |
| 28 | 0.2 | 0.2 | 0.2 | 0.3 | 1.2 | 0.2 | 0.04 | 0.1 | $0.6 \pm 0.37$ |
| 29 | 0.1 | 1.1 | 0.1 | 1.0 | 5.8 | 0.8 | 0.9 | 0.4 | $3.1 \pm 1.2$ |

[a]The cytotoxicity $GI_{50}$ values are the concentrations corresponding to 50% growth inhibition.
[b]Mean graph midpoint for growth inhibition of all human cancer cell lines successfully tested, ranging from $10^{-8}$ to $10^{-4}$ molar.
[c]For MGM $GI_{50}$ values in which a standard error appears, the $GI_{50}$ values for individual cell lines are the average of two determinations.

The invention claimed is:
1. A compound of the formula

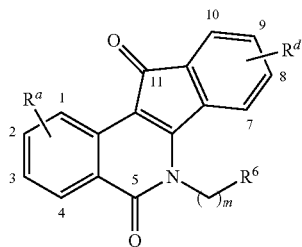

(I)

or a pharmaceutically acceptable salt, hydrate or solvate thereof,
wherein:
m is an integer from 0 to about 6;
$R^6$ is selected from the group consisting of haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, hydroxyalkylamino, bis(hydroxyalkyl)amino, hydroxyalkylaminoalkylamino, heteroarylalkylaminoalkylamino, acylamino, hydroxylamino, alkoxylamino, acyloxylamino, cycloalkyl, heterocyclyl, heterocyclylamino, alkynyl, acyl, urethanyl, cyano, nitro, thio, alkylsulfonyl, sulfonic acid, carboxylic acid, and phosphonic acid; provided that when $R^6$ is hydroxy, alkylamino, or hydroxyalkylamino, m is the integer 0;
$R^a$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid; or $R^a$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid;
$R^d$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid; or $R^d$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid, and
wherein at least one of $R^a$ or $R^d$ is not hydrogen.
2. The compound of claim 1, wherein $R^6$ is selected from the group consisting of amino, alkyl and dialkylamino, trialkylammonium, hydroxyalkylamino, bis(hydroxyalkyl)amino, and hydroxyalkylaminoalkylamino.
3. The compound of claim 1, wherein $R^6$ is selected from the group consisting of heteroaryl, heteroaryloxy, and heteroarylamino, heteroarylalkylaminoalkylamino, heterocyclyl, heterocyclylamino, each of which is optionally substituted.
4. The compound of claim 1, wherein $R^6$ is optionally substituted heterocyclyl or optionally substituted heterocyclylamino.
5. The compound of claim 1, wherein $R^6$ is morpholin-4-yl.
6. The compound of claim 1, wherein $R^6$ is optionally substituted heteroaryl or optionally substituted heteroarylamino.
7. The compound of claim 1, wherein $R^6$ is imidazole-1-yl.
8. The compound of claim 1, wherein $R^d$ includes an alkylenedioxy group.
9. The compound of claim 1, wherein $R^d$ includes one or more optionally substituted alkoxy.
10. The compound of claim 1, wherein $R^a$ includes one or more alkoxy optionally substituted with alkenyl, alkynyl, halo, nitro, cyano, azido, amino, alkylamino, dialkylamino, hydroxyalkylamino, bis(hydroxyalkyl)amino, cycloalkyl, aryl, hetereocyclyl, heteroaryl, alkylcarbonyl, alkoxycarbonyl, or hydrazinecarbonyl.
11. The compound of claim 10, wherein said alkoxy is optionally substituted with amino, alkylamino, or dialkylamino.
12. The compound of claim 10, wherein said alkoxy is optionally substituted with heterocyclyl.
13. The compound of claim 12, wherein said heterocyclyl is morpholino, 4-methylpiperazinyl, piperidinyl, or pyrrodinyl.
14. The compound of claim 10, wherein said alkoxy is optionally substituted with alkylcarbonyl, alkoxycarbonyl, or hydrazinecarbonyl.
15. The compound of claim 10, wherein $R^a$ includes one methoxy and one alkoxy substituted with alkenyl, alkynyl, halo, nitro, cyano, azido, amino, alkylamino, dialkylamino, cycloalkyl, aryl, hetereocyclyl, heteroaryl, alkylcarbonyl, alkoxycarbonyl, or hydrazinecarbonyl.
16. The compound of claim 10, wherein $R^a$ includes one optionally substituted alkoxy and one hydroxy.
17. The compound of claim 1, wherein m is 3.
18. The compound of claim 1, wherein the compound is
2-(3-bromopropoxy)-3-methoxy-6-(3-morpholinopropyl)-5H-[1,3]dioxolo[4',5':5,6]indeno[1,2-c]isoquinoline-5,12(6H)-dione;
2-(allyloxy)-3-methoxy-6-(3-morpholinopropyl)-5H-[1,3]dioxolo[4',5':5,6]indeno[1,2-c]isoquinoline-5,12(6H)-dione;
2-(3-azidopropoxy)-3-methoxy-6-(3-morpholinopropyl)-5H-[1,3]dioxolo[4',5':5,6]indeno[1,2-c]isoquinoline-5,12(6H)-dione;
2-(3-Aminopropoxy)-3-methoxy-6-(3-morpholinopropyl)-5H-[1,3]dioxolo[4',5':5,6]indeno[1,2-c]isoquinoline-5,12(6H)-dione;
2-(3-(dimethylamino)propoxy)-3-methoxy-6-(3-morpholinopropyl)-5H-[1,3]dioxolo[4',5':5,6]indeno[1,2-c]isoquinoline-5,12(6H)-dione;
2-(3-(ethylamino)propoxy)-3-methoxy-6-(3-morpholinopropyl)-5H-[1,3]dioxolo[4',5':5,6]indeno[1,2-c]isoquinoline-5,12(6H)-dione;
3-Methoxy-2-(3-morpholinopropoxy)-6-(3-morpholinopropyl)-5H-[1,3]dioxolo[4',5':5,6]indeno[1,2-c]isoquinoline-5,12(6H)-dione;

3-methoxy-2-(3-(4-methylpiperazin-1-yl)propoxy)-6-(3-morpholinopropyl)-5H-[1,3]dioxolo[4',5':5,6]indeno[1,2-c]isoquinoline-5,12(6H)-dione;

3-methoxy-6-(3-morpholinopropyl)-2-(3-(piperidin-1-yl)propoxy)-5H-[1,3]dioxolo[4',5':5,6]indeno[1,2-c]isoquinoline-5,12(6H)-dione;

3-methoxy-6-(3-morpholinopropyl)-2-(3-(pyrrolidin-1-yl)propoxy)-5H-[1,3]dioxolo[4',5':5,6]indeno[1,2-c]isoquinoline-5,12(6H)-dione;

Methyl 2-((3-Methoxy-6-(3-morpholinopropyl)-5,12-dioxo-6,12-dihydro-5H-[1,3]dioxolo[4',5':5,6]indeno[1,2-c]isoquinolin-2-yl)oxy)acetate; or 2-((12-hydroxy-3-methoxy-6-(3-morpholinopropyl)-5-oxo-6,12-dihydro-5H-[1,3]dioxolo[4',5':5,6]indeno[1,2-c]isoquinolin-2-yl)oxy)acetohydrazide.

19. A pharmaceutical composition comprising a compound of claim 1, or a pharmaceutically acceptable salt, hydrate, or solvate thereof, and one or more pharmaceutically acceptable carriers, diluents, and excipients.

20. A method for treating cancer, the method comprising the step of administering to a patient in need of relief from said cancer a therapeutically effective amount of a compound of the formula

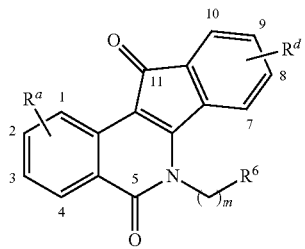

(I)

or a pharmaceutically acceptable salt, hydrate, or solvate thereof,
wherein:
m is an integer from 0 to about 6;
$R^6$ is selected from the group consisting of haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, hydroxyalkylamino, bis(hydroxyalkyl)amino, hydroxyalkylaminoalkylamino, heteroarylalkylaminoalkylamino, acylamino, hydroxylamino, alkoxylamino, acyloxylamino, cycloalkyl, heterocyclyl, heterocyclylamino, alkynyl, acyl, urethanyl, cyano, nitro, thio, alkylsulfonyl, sulfonic acid, carboxylic acid, and phosphonic acid; provided that when $R^6$ is hydroxy, alkylamino, or hydroxyalkylamino, m is the integer 0;

$R^a$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid; or $R^a$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid;

$R^d$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid; or $R^d$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid, and wherein at least one of $R^a$ or $R^d$ is not hydrogen.

* * * * *

SEQUENCE LISTING

```
<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<223> OTHER INFORMATION: topoisomerase substrate
<220> FEATURE:
<221> NAME/KEY: misc_feature
<222> LOCATION: (14)..(14)
<223> OTHER INFORMATION: Tryosine attached via phosphate linkage to the
      hydroxyl group of the tyrosine.

<400> SEQUENCE: 1
gatctaaaag actt                                                        14

<210> SEQ ID NO 2
<211> LENGTH: 14
<212> TYPE: DNA
<213> ORGANISM: artificial
<220> FEATURE:
<223> OTHER INFORMATION: product from enzymatic cleavage of SEQ ID NO. 1

<400> SEQUENCE: 2
gatctaaaag actt                                                        14
```